(12) United States Patent
Cho et al.

(10) Patent No.: US 7,973,013 B2
(45) Date of Patent: Jul. 5, 2011

(54) 2'-FLUORO SUBSTITUTED CARBA-NUCLEOSIDE ANALOGS FOR ANTIVIRAL TREATMENT

(75) Inventors: Aesop Cho, Mountain View, CA (US); Choung U. Kim, San Carlos, CA (US); Samuel E. Metobo, Newark, CA (US); Adrian S. Ray, Redwood City, CA (US); Jie Xu, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 12/885,917

(22) Filed: Sep. 20, 2010

(65) Prior Publication Data

US 2011/0070194 A1 Mar. 24, 2011

Related U.S. Application Data

(60) Provisional application No. 61/244,297, filed on Sep. 21, 2009.

(51) Int. Cl.
*A01N 43/04* (2006.01)
*A61K 31/70* (2006.01)
*C07H 5/04* (2006.01)
*C07H 7/06* (2006.01)

(52) U.S. Cl. ........... 514/23; 536/18.7; 536/29.2; 536/55

(58) Field of Classification Search ...................... None
See application file for complete search history.

(56) References Cited

U.S. PATENT DOCUMENTS

2010/0298257 A1* 11/2010 Ross et al. ...................... 514/51

FOREIGN PATENT DOCUMENTS

| WO | WO-00/56734 A1 | 9/2000 |
| WO | WO-01/32153 A2 | 5/2001 |
| WO | WO-01/60315 A2 | 8/2001 |
| WO | WO-01/90121 A2 | 11/2001 |
| WO | WO-02/18404 A2 | 3/2002 |
| WO | WO-02/32920 A2 | 4/2002 |
| WO | WO-02/057287 A2 | 7/2002 |
| WO | WO-02/057425 A2 | 7/2002 |
| WO | WO-2004/046331 A2 | 6/2004 |
| WO | WO-2006/065335 A2 | 6/2006 |
| WO | WO2008/005542 * | 1/2008 |
| WO | WO-2008/005542 A2 | 1/2008 |
| WO | WO-2008085508 A2 | 7/2008 |
| WO | WO-2008089105 A2 | 7/2008 |
| WO | WO2008/141079 * | 11/2008 |
| WO | WO-2008/141079 A1 | 11/2008 |
| WO | WO-2009/132123 A1 | 10/2009 |
| WO | WO-2009/132135 A1 | 10/2009 |
| WO | WO-2010/002877 A2 | 1/2010 |

OTHER PUBLICATIONS

Bojack, G et al. (2001) "Design and Synthesis of Inhibitors of Adenosine and AMP Deaminases," *Organic Letters* 3(6):839-842.
Dudfield, P. et al. (1999) "Synthesis of C-ribosyl imidazo [2,1-f][1,2,4]triazines as inhibitors of adenosine and AMP deaminases," *J. Chem. Soc. Perkin Trans.1* 2929-2936.
Dudfield, P. et al. (1999) "Synthesis of C-ribosyl 1,2,4-triazolo[3,4-f][1,2,4]triazines as inhibitors of adebosine and AMP deaminasses," *J. Chem. Soc. Perkin Trans I* 2937-2942.
Hayashi, M. (1992) "C-Nucleosides. 17.[1] A Synthesis of 2-Substituted 7-(β-D-Ribofuranosyl)-Pyrrolo[2,1-f]-1,2,4-Traizines. A New Type of "PURINE LIKE" C-Nucleoside" *Heterocycles* 34(3):569-574.
Knutsen, L. (1984) "Synthesis of Imidazo-fused Bridgehead-nitrogen C—Nucleosides via Dehydrative Coupling Reactions of 2.5-Anhydro-3,4,6-tri-O-benzoyl-$_D$-allonic Acid," *J. Chem. Soc. Perkin Trans I* pp. 229-238.
Knutsen, L. (1985) "Synthesis of Imidazo-fused Bridgehead-nitrogen 2'-Deoxyribo-C-nucleosides: Coupling-Elimination Reactions of 2.5-Anhydro-3,4,6-tri-O-benzoyl-o-allonic Acid," *J. Chem. Soc. Perkin Trans. 1* pp. 621-630.
Nishimura, N. (2001) "Synthesis of pyrrolo[2,1-f][1,2,4]triazine C-nucleosides, Isosteres of sangivamycin, tubercidin, and toyocamycin," *Carbohydrate Research* 331:77-82.
Otter, B. (1996) "Conformational Properties of Purine-Like C-Nucleosides," *Nucleosides & Nucleotides* 15(1-3):793-807.
Patil, S. (1994) "4-Aza-7,9-Dideazadenosine, A New Cytotoxic Synthetic C-Nucleoside Analogue of Adenosine," *Tetrahedron Letters* 35(30):5339-5342.
Patil, S. (1994) "Synthesis of Pyrrolo[2, 1-f][1,2,4]triazine Congeners of Nucleic Acid Purines via the N-Amination of 2-Substituted Pyrroles," *J. Heterocyclic Chem..* 31:781-786.
Ramasamy, K. (1986) "Synthesis and Antitumor Activity of Certain 3-βD-Ribofuranosyl-1,2,4-triazolo[3,4-f]-1,2,4-triazines Related to formycin Prepared via Ring Closure of a 1,2,4-Triazine Precursor," *J. Med, Chem.* 29:2231-2235.
International Search Report for PCT/US2010/049471, mailed Nov. 18, 2010.
Written Opinion for PCT/US2010/049471, mailed Nov. 18, 2010.

* cited by examiner

*Primary Examiner* — Traviss C McIntosh, III

(57) ABSTRACT

Provided are pyrrolo[1,2-f][1,2,4]triazinyl, imidazo[1,5-f][1,2,4]triazinyl, imidazo[1,2-f][1,2,4]triazinyl, and [1,2,4]triazolo[4,3-f][1,2,4]triazinyl nucleosides, nucleoside phosphates and prodrugs thereof, wherein the 2' position of the nucleoside sugar is substituted with halogen and carbon substitutents. The compounds, compositions, and methods provided are useful for the treatment of Flaviviridae virus infections, particularly hepatitis C infections caused by both wild type and mutant strains of HCV.

20 Claims, No Drawings

2'-FLUORO SUBSTITUTED CARBA-NUCLEOSIDE ANALOGS FOR ANTIVIRAL TREATMENT

This application is filed under 35 U.S.C. 111(a) claiming the benefit under 35 U.S.C. 119(e) of U.S. provisional application 61/244,297 filed Sep. 21, 2009 which is herein incorporated by reference in its entirety for all purposes.

FIELD OF THE INVENTION

The invention relates generally to compounds with antiviral activity, more particularly nucleosides active against Flaviviridae infections and most particularly to inhibitors of hepatitis C virus RNA-dependent RNA polymerase.

BACKGROUND OF THE INVENTION

Viruses comprising the Flaviviridae family comprise at least three distinguishable genera including pestiviruses, flaviviruses, and hepaciviruses (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). Flaviviruses are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Bescegelie, A. M. and Bacon, B. R., Scientific American, Oct.: 80-85, (1999); Gordon, C. P., et al., J. Med. Chem. 2005, 48, 1-20; Maradpour, D.; et al., Nat. Rev. Micro. 2007, 5(6), 453-463). A number of HCV treatments are reviewed by Bymock et al. in Antiviral Chemistry & Chemotherapy, 11:2; 79-95 (2000).

RNA-dependent RNA polymerase (RdRp) is one of the best studied targets for the development of novel HCV therapeutic agents. The NS5B polymerase is a target for inhibitors in early human clinical trials (Sommadossi, J., WO 01/90121 A2, US 2004/0006002 A1). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Virol. 22:73-89). Biochemical targets such as NS5B are important in developing HCV therapies since HCV does not replicate in the laboratory and there are difficulties in developing cell-based assays and preclinical animal systems.

Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. Drugs 2002, 62, 507-556) but less than half the patients infected with some genotypes show a persistent benefit when given this treatment. Other patent applications disclosing the use of nucleoside analogs to treat hepatitis C virus include WO 01/32153, WO 01/60315, WO 02/057425, WO 02/057287, WO 02/032920, WO 02/18404, WO 04/046331, WO2008/089105 and WO2008/141079 but additional treatments for HCV infections have not yet become available for patients.

Virologic cures of patients with chronic HCV infection are difficult to achieve because of the prodigous amount of daily virus production in chronically infected patients and the high spontaneous mutability of HCV virus (Neumann, et al., Science 1998, 282, 103-7; Fukimoto, et al., Hepatology, 1996, 24, 1351-4; Domingo, et al., Gene, 1985, 40, 1-8; Martell, et al., J. Viral. 1992, 66, 3225-9. Experimental anti-viral nucleoside analogs have been shown to induce vialable mutations in the HCV virus both in vivo and in vitro (Migliaccio, et al., J. Biol. Chem. 2003, 926; Carroll, et al., Antimicrobial Agents Chemotherapy 2009, 926; Brown, A. B., Expert Opin. Investig. Drugs 2009, 18, 709-725). Therefore, drugs having improved antiviral properties, particularly enhanced activity against resistant strains of virus; improved oral bioavailability; fewer undesirable side effects and extended effective half-life in vivo (De Francesco, R. et al. (2003) Antiviral Research 58:1-16) are urgently needed.

Certain ribosides of the nucleobases pyrrolo[1,2-f][1,2,4]triazine, imidazo[1,5-f][1,2,4]triazine, imidazo[1,2-f][1,2,4]triazine, and [1,2,4]triazolo[4,3-f][1,2,4]triazine have been disclosed in Carbohydrate Research 2001, 331(1), 77-82; Nucleosides & Nucleotides (1996), 15(1-3), 793-807; Tetrahedron Letters (1994), 35(30), 5339-42; Heterocycles (1992), 34(3), 569-74; J. Chem. Soc. Perkin Trans. 1 1985, 3, 621-30; J. Chem. Soc. Perkin Trans, 1 1984, 2, 229-38; WO 2000056734; Organic Letters (2001), 3(6), 839-842; J. Chem. Soc. Perkin Trans. 1 1999, 20, 2929-2936; and J. Med. Chem. 1986, 29(11), 2231-5. However, these compounds have not been disclosed as useful for the treatment of HCV.

Ribosides of pyrrolo[1,2-f][1,2,4]triazinyl, imidazo[1,5-f] [1,2,4]triazinyl, imidazo[1,2-f][1,2,4]triazinyl, and [1,2,4]triazolo[4,3-f][1,2,4]triazinyl nucleobases with antiviral, anti-HCV, and anti-RdRp activity have been disclosed by Babu, Y. S., WO2008/089105 and WO2008/141079; Cho, et al., WO2009/132123 and Francom, et al. WO2010/002877. Butler, et al., WO2009/132135, has disclosed anti-viral pyrrolo[1,2-f][1,2,4]triazinyl, imidazo[1,5-f][1,2,4]triazinyl, imidazo[1,2-f][1,2,4]triazinyl, and [1,2,4]triazolo[4,3-f][1,2, 4]triazinyl nucleosides wherein the 1' position of the nucleoside sugar is substituted.

SUMMARY OF THE INVENTION

Provided are compounds that inhibit viruses of the Flaviviridae family. The invention also comprises compounds of Formula I that inhibit viral nucleic acid polymerases, particularly HCV RNA-dependent RNA polymerase (RdRp), rather than cellular nucleic acid polymerases. The compounds of Formula I have been discovered to be efficacious against both wild type and S282T mutant strains of HCV virus. Therefore, a compound of Formula I is useful for treating Flaviviridae infections in humans and other animals.

In one embodiment, provided are compounds of Formula I:

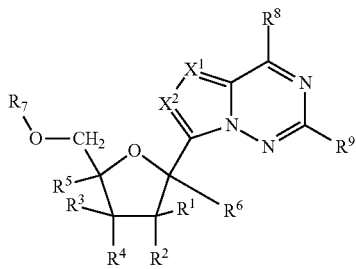

Formula I or a pharmaceutically acceptable salt, thereof;
wherein:
$R^1$ is $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

$R^2$ is halogen;

each $R^3$, $R^4$, or $R^5$ is independently H, $OR^a$, $N(R^a)_2$, $N_3$, CN, $NO_2$, $S(O)_nR^a$, halogen, $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

or any two of $R^3$, $R^4$ or $R^5$ on adjacent carbon atoms when taken together are —O(CO)O— or when taken together with the ring carbon atoms to which they are attached form a double bond;

$R^6$ is H, $OR^a$, $N(R^a)_2$, $N_3$, CN, $NO_2$, $S(O)_nR^a$, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2(OR^{11})$, —SO$_2NR^{11}R^{12}$, halogen, $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

each n is independently 0, 1, or 2;

each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$carbocyclylalkyl, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2(OR^{11})$, or —SO$_2NR^{11}R^{12}$;

$R^7$ is H, —C(=O)$R^{11}$, —C(=O)$OR^{11}$, —C(=O)$NR^{11}R^{12}$, —C(=O)$SR^{11}$, —S(O)$R^{11}$, —S(O)$_2R^{11}$, —S(O)($OR^{11}$), —S(O)$_2(OR^{11})$, —SO$_2NR^{11}R^{12}$, or

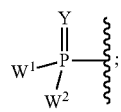

each Y or $Y^1$ is, independently, O, S, NR, $^+N(O)(R)$, N(OR), $^+N(O)(OR)$, or N—$NR_2$;

$W^1$ and $W^2$, when taken together, are —$Y^3(C(R^y)_2)_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of the Formula Ia:

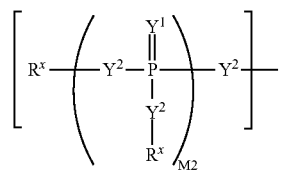

Formula Ia wherein:
each $Y^2$ is independently a bond, O, $CR_2$, NR, $^+N(O)(R)$, N(OR), $^+N(O)(OR)$, N—$NR_2$, S, S—S, S(O), or S(O)$_2$;
each $Y^3$ is independently O, S, or NR;
M2 is 0, 1 or 2;
each $R^x$ is independently $R^y$ or the formula:

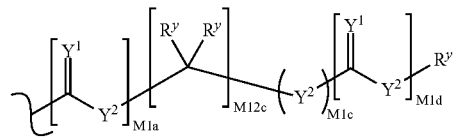

wherein:
each M1a, M1c, and M1d is independently 0 or 1;
M12c is 0, 1, 2, 3, 4, 5, 6, 7, 8, 9, 10, 11 or 12;
each $R^y$ is independently H, F, Cl, Br, I, OH, R, —C(=$Y^1$)R, —C(=$Y^1$)OR, —C(=$Y^1$)$N(R)_2$, —$N(R)_2$, —$^+N(R)_3$, —SR, —S(O)R, —S(O)$_2$R, —S(O)(OR), —S(O)$_2$(OR), —OC(=$Y^1$)R, —OC(=$Y^1$)OR, —OC(=$Y^1$)$(N(R)_2)$, —SC(=$Y^1$)R, —SC(=$Y^1$)OR, —SC(=$Y^1$)$(N(R)_2)$, —N(R)C(=$Y^1$)R, —N(R)C(=$Y^1$)OR, —N(R)C(=$Y^1$)$N(R)_2$, —SO$_2NR_2$, —CN, —$N_3$, —$NO_2$, —OR, or $W^3$; or when taken together, two $R^y$ on the same carbon atom form a carbocyclic ring of 3 to 7 carbon atoms;

each R is independently H, $(C_1-C_8)$ alkyl, $(C_1-C_8)$ substituted alkyl, $(C_2-C_8)$alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, arylalkyl or substituted arylalkyl;

$W^3$ is $W^4$ or $W^5$; $W^4$ is R, —C($Y^1$)$R^y$, —C($Y^1$)$W^5$, —SO$_2R^y$, or —SO$_2W^5$; and $W^5$ is a carbocycle or a heterocycle wherein $W^5$ is independently substituted with 0 to 3 $R^y$ groups;

each $X^1$ or $X^2$ is independently C—$R^{10}$ or N;

each $R^8$ is halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NNHR^{11}$, —CH=$N(OR^{11})$, —CH$(OR^{11})_2$, —C(=O)$NR^{11}R^{12}$, —C(=S)$NR^{11}R^{12}$, —C(=O)$OR^{11}$, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)$(C_1-C_8)$alkyl, —S(O)$_n(C_1-C_8)$alkyl, aryl$(C_1-C_8)$alkyl, $OR^{11}$ or $SR^{11}$;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, —CH(=$NR^{11}$), —CH=$NHNR^{11}$, —CH=$N(OR^{11})$, —CH$(OR^{11})_2$, —C(=O)$NR^{11}R^{12}$, —C(=S)$NR^{11}R^{12}$, —C(=O)$OR^{11}$, $R^{11}$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)$(C_1-C_8)$alkyl, —S(O)$_n(C_1-C_8)$alkyl or aryl$(C_1-C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —NR$^a$—;

wherein each $(C_1-C_8)$alkyl, $(C_2-C_8)$alkenyl, $(C_2-C_8)$alkynyl or aryl$(C_1-C_8)$alkyl of each $R^1$, $R^3$, $R^4$, $R^5$, $R^6$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1-C_8)$ alkyl may be optionally replaced with —O—, —S— or —NR$^a$—.

In another embodiment, provided are compounds of Formula I and pharmaceutically acceptable salts thereof and all racemates, enantiomers, diastereomers, tautomers, polymorphs, pseudopolymorphs and amorphous forms thereof.

In another embodiment, provided are novel compounds of Formula I with activity against infectious Flaviviridae viruses. Without wishing to be bound by theory, the compounds of the invention may inhibit viral RNA-dependent RNA polymerase and thus inhibit the replication of the virus. They are useful for treating human patients infected with a human virus such as hepatitis C.

In another embodiment, provided are pharmaceutical compositions comprising an effective amount of a Formula I compound, or a pharmaceutically acceptable salt thereof, in combination with a pharmaceutically acceptable diluent or carrier.

In another embodiment, the present application provides for combination pharmaceutical agent comprising:

a) a first pharmaceutical composition comprising a compound of Formula I; or a pharmaceutically acceptable salt, solvate, or ester thereof; and b) a second pharmaceutical composition comprising at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

In another embodiment, the present application provides for a method of inhibiting HCV polymerase, comprising contacting a cell infected with HCV with an effective amount of a compound of Formula I; or a pharmaceutically acceptable salts, solvate, and/or ester thereof.

In another embodiment, the present application provides for a method of inhibiting HCV polymerase, comprising contacting a cell infected with HCV with an effective amount of a compound of Formula I; or a pharmaceutically acceptable salts, solvate, and/or ester thereof; and at least one additional therapeutic agent.

In another embodiment, the present application provides for a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral diarrhea virus, Zika virus and Hepatitis C virus; by administering to a subject in need thereof a therapeutically effective amount of a compound of Formula I, or a pharmaceutically acceptable salt thereof.

In another embodiment, the present application provides for a method of treating HCV in a patient, comprising administering to said patient a therapeutically effective amount of a compound of Formula I; or a pharmaceutically acceptable salt, solvate, and/or ester thereof.

In another embodiment, the present application provides for a method of treating HCV in a patient, comprising administering to said patient a therapeutically effective amount of a compound of Formula I; or a pharmaceutically acceptable salt, solvate, and/or ester thereof; and at least one additional therapeutic agent.

Another aspect of the invention provides a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another aspect, the invention also provides a method of inhibiting HCV, comprising administering to a mammal infected with HCV an amount of a Formula I compound, effective to inhibit the replication of HCV in infected cells in said mammal.

In another aspect, provided is the use of a compound of Formula I for the manufacture of a medicament for the treatment of Flaviviridae viral infections. In another aspect, provided is a compound of Formula I for use in treating a Flaviviridae viral infection. In one embodiment, the Flaviviridae viral infection is acute or chronic HCV infection. In one embodiment of each aspect of use and compound, the treatment results in the reduction of one or more of the viral loads or clearance of RNA in the patient.

In another aspect, the invention also provides processes and novel intermediates disclosed herein which are useful for preparing Formula I compounds of the invention.

In other aspects, novel methods for synthesis, analysis, separation, isolation, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

In another aspect, compounds of Formula I are represented by Formula II:

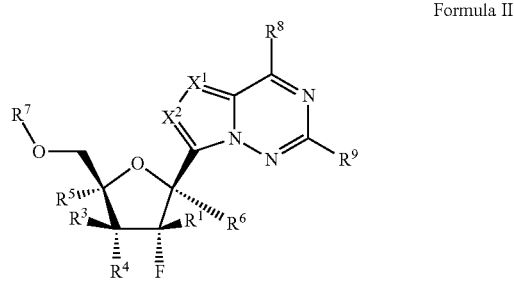

Formula II or a pharmaceutically acceptable salt, thereof;

wherein:

$R^1$ is $(C_1-C_8)$alkyl, $(C_4-C_8)$carbocyclylalkyl, $(C_1-C_8)$ substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

each $R^3$, $R^4$, or $R^5$ is independently H, $OR^a$, $N(R^a)_2$, $N_3$, CN, $NO_2$, $S(O)_nR^a$, halogen, $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

or any two of $R^3$, $R^4$ or $R^5$ on adjacent carbon atoms when taken together are —O(CO)O— or when taken together with the ring carbon atoms to which they are attached form a double bond;

$R^6$ is H, $OR^a$, $N(R^a)_2$, $N_3$, CN, $NO_2$, $S(O)_nR^a$, —C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), —SO$_2$N$R^{11}R^{12}$, halogen, $(C_1-C_8)$alkyl, $(C_4-C_8)$carbocyclylalkyl, $(C_1-C_8)$substituted alkyl, $(C_2-C_8)$alkenyl, $(C_2-C_8)$substituted alkenyl, $(C_2-C_8)$alkynyl, $(C_2-C_8)$substituted alkynyl, or aryl$(C_1-C_8)$alkyl;

each n is independently 0, 1, or 2;

each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$carbocyclylalkyl, —C(=O)$R^{11}$, —C(=O)O$R^{11}$, —C(=O)N$R^{11}R^{12}$, —C(=O)S$R^{11}$, S(O)$R^{11}$, —S(O)$_2R^{11}$, —S(O)($R^{11}$), —S(O)$_2$(O$R^{11}$), or —SO$_2$N$R^{11}R^{12}$;

$R^7$ is H, C(=O)$R^{11}$, —C(=O)O$R^{11}$, —C(=O)N$R^{11}R^{12}$, —C(=O)S$R^{11}$, —S(O)$R^{11}$, —S(O)$_2R^{11}$, —S(O)(O$R^{11}$), —S(O)$_2$(O$R^{11}$), —SO$_2$N$R^{11}R^{12}$, or

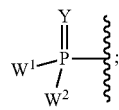

each Y or $Y^1$ is, independently, O, S, NR, $^+$N(O)(R), N(OR), $^+$N(O)(OR), or N—NR$_2$;

$W^1$ and $W^2$, when taken together, are —$Y^3$(C(R$^y$)$_2$)$_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of the Formula Ia:

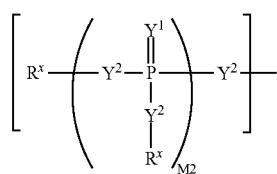

Formula Ia wherein:

each $Y^2$ is independently a bond, O, CR$_2$, NR, $^+$N(O)(R), N(OR), $^+$N(O)(OR), N—NR$_2$, S, S—S, S(O), or S(O)$_2$;

each $Y^3$ is independently O, S, or NR;

M2 is 0, 1 or 2;

each $R^x$ is independently $R^y$ or the formula:

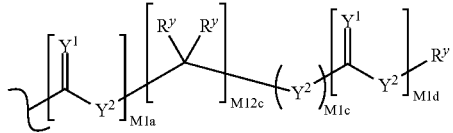

wherein:

each M1a, M1c, and M1d is independently 0 or 1;
M12c is 0, 1, 2, 3, 4, 5, 6, 7, 8, 9, 10, 11 or 12;
each $R^y$ is independently H, F, Cl, Br, I, OH, R, —C(=$Y^1$)R, —C(=$Y^1$)OR, —C(=$Y^1$)N(R)$_2$, —N(R)$_2$, —$^+$N(R)$_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, —N(R)C(=$Y^1$)N(R)$_2$, —SO$_2$NR$_2$, —CN, —N$_3$, —NO$_2$, —OR, or $W^3$; or when taken together, two $R^y$ on the same carbon atom form a carbocyclic ring of 3 to 7 carbon atoms;

each R is independently H, $(C_1-C_8)$ alkyl, $(C_1-C_8)$ substituted alkyl, $(C_2-C_8)$alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, arylalkyl or substituted arylalkyl;

$W^3$ is $W^4$ or $W^5$; $W^4$ is R, —C($Y^1$)$R^y$, —C($Y^1$)$W^5$, —SO$_2R^y$, or —SO$_2W^5$; and $W^5$ is a carbocycle or a heterocycle wherein $W^5$ is independently substituted with 0 to 3 $R^y$ groups;

each $X^1$ or $X^2$ is independently C—$R^{10}$ or N;

each $R^8$ is halogen, N$R^{11}R^{12}$, N($R^{11}$)O$R^{11}$, N$R^{11}$N$R^{11}R^{12}$, $N_3$, NO, $NO_2$, CHO, CN, —CH(=N$R^{11}$), —CH=NNHR$^{11}$, —CH=N(O$R^{11}$), —CH(O$R^{11}$)$_2$, —C(=O)N$R^{11}R^{12}$, —C(=S)N$R^{11}R^{12}$, —C(=O)O$R^{11}$, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)$(C_1-C_8)$alkyl, —S(O)$_n(C_1-C_8)$alkyl, aryl$(C_1-C_8)$alkyl, O$R^{11}$ or S$R^{11}$;

each $R^9$ or $R^{10}$ is independently H, halogen, N$R^{11}R^{12}$, N($R^{11}$)O$R^{11}$, N$R^{11}$N$R^{11}R^{12}$, $N_3$, NO, $NO_2$, CHO, CN, —CH(=N$R^{11}$), —CH=NHN$R^{11}$, —CH=N(O$R^{11}$), —CH(O$R^{11}$)$_2$, —C(=O)N$R^{11}R^{12}$, —C(=S)N$R^{11}R^{12}$, —C(=O)O$R^{11}R^{12}$, —C(=O)O$R^{11}$, $R^{11}$, O$R^{11}$ or S$R^{11}$;

each $R^{11}$ or $R^{12}$ is independently H, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)$(C_1-C_8)$alkyl, —S(O)$_n(C_1-C_8)$alkyl or aryl$(C_1-C_8)$alkyl; or $R^{11}$ and $R^{12}$ taken together with a nitrogen to which they are both attached form a 3 to 7 membered heterocyclic ring wherein any one carbon atom of said heterocyclic ring can optionally be replaced with —O—, —S— or —N$R^a$—;

wherein each $(C_1-C_8)$alkyl, $(C_2-C_8)$alkenyl, $(C_2-C_8)$alkynyl or aryl$(C_1-C_8)$alkyl of each $R^1$, $R^3$, $R^4$, $R^5$, $R^6$, $R^{11}$ or $R^{12}$ is, independently, optionally substituted with one or more halo, hydroxy, CN, $N_3$, N($R^a$)$_2$ or O$R^a$; and wherein one or more of the non-terminal carbon atoms of each said $(C_1-C_8)$ alkyl may be optionally replaced with —O—, —S— or —N$R^a$—.

In one embodiment of the invention of Formula II, $R^1$ is $(C_1-C_8)$alkyl, $(C_2-C_8)$ alkenyl or $(C_2-C_8)$alkynyl. In another aspect of this embodiment, $R^1$ is $(C_1-C_8)$alkyl. In another aspect of this embodiment, $R^1$ is methyl, CH$_2$F, or ethynyl. In another aspect of this embodiment, $R^1$ is methyl. In another aspect of this embodiment, $R^1$ is $(C_1-C_8)$alkyl and $R^6$ is H. In another aspect of this embodiment, $R^1$ is $(C_1-C_8)$alkyl and at least one of $X^1$ or $X^2$ is N. In another aspect of this embodiment, $R^1$ is $(C_1-C_8)$alkyl and $R^6$ is CN, OH, or $CH_3$.

In one embodiment of Formula II, $R^3$ is H, $OR^a$, $N(R^a)_2$, $N_3$, CN, $SR^a$, halogen, $(C_1-C_8)$alkyl, $(C_2-C_8)$alkenyl or $(C_2-C_8)$alkynyl. In one aspect of this embodiment, $R^3$ is H. In another aspect of this embodiment, $R^3$ is H and $R^1$ is $(C_1-C_8)$alkyl, $(C_2-C_8)$ alkenyl or $(C_2-C_8)$alkynyl. In another aspect of this embodiment, $R^3$ is H and $R^1$ is $(C_1-C_8)$alkyl. In another aspect of this embodiment, $R^3$ is H and $R^1$ methyl, $CH_2F$, or ethynyl. In another aspect of this embodiment, $R^3$ is H and $R^1$ is methyl. In another aspect of this embodiment, $R^3$ is H, $R^1$ is $(C_1-C_8)$alkyl and at least one of $X^1$ or $X^2$ is N. In another aspect of this embodiment, $R^3$ is H, $R^1$ is methyl and at least one of $X^1$ or $X^2$ is N. In another aspect of this embodiment, $R^3$ is H, $R^1$ is $(C_1-C_8)$alkyl and $R^6$ is CN, OH, or $CH_3$. In another aspect of this embodiment, $R^3$ is H, $R^1$ is methyl and $R^6$ is CN, OH, or $CH_3$. In another aspect of this embodiment, $R^3$ is H, $R^1$ is methyl and $R^6$ is H.

In one embodiment of Formula II, $R^4$ is H, $OR^a$, $N(R^a)_2$, $N_3$, CN, $SR^a$, halogen, $(C_1-C_8)$alkyl, $(C_2-C_8)$alkenyl or $(C_2-C_8)$alkyl. In another aspect of this embodiment, $R^4$ is H or $OR^a$. In another aspect of this embodiment, $R^4$ is $OR^a$. In another aspect of this embodiment, $R^4$ is $OR^a$ and $R^1$ is $(C_1-C_8)$alkyl, $(C_2-C_8)$ alkenyl or $(C_2-C_8)$alkynyl. In another aspect of this embodiment, $R^4$ is $OR^a$ and $R^1$ is $(C_1-C_8)$alkyl, $(C_2-C_8)$ alkenyl or $(C_2-C_8)$alkynyl. In another aspect of this embodiment, $R^4$ is $OR^a$ and $R^1$ is $(C_1-C_8)$alkyl. In another aspect of this embodiment, $R^4$ is $OR^a$ and $R^1$ is methyl. In another aspect of this embodiment, $R^4$ is $OR^a$, $R^1$ is $(C_1-C_8)$alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is $(C_1-C_8)$alkyl and $R^6$ is CN, OH, or $CH_3$. In another aspect of this embodiment, $R^4$ is $OR^a$, $R^1$ is methyl and $R^6$ is CN, OH, or $CH_3$. In another aspect of this embodiment, $R^4$ is $OR^a$, is methyl and $R^6$ is H. In another aspect of this embodiment, $R^4$ is OH and $R^1$ is methyl. In another aspect of this embodiment, $R^4$ is OH, $R^1$ is $(C_1-C_8)$alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is $(C_1-C_8)$alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In one embodiment of Formula II, $R^5$ is H, $OR^a$, $N(R^a)_2$, $N_3$, CN, $SR^a$, halogen, $(C_1-C_8)$alkyl, $(C_2-C_8)$alkenyl or $(C_2-C_8)$alkynyl. In another aspect of this embodiment, $R^4$ is H or $OR^a$. In another aspect of this embodiment, $R^4$ is $OR^a$. In another aspect of this embodiment, $R^4$ is $OR^a$ and $R^1$ is $(C_1-C_8)$alkyl, $(C_2-C_8)$ alkenyl or $(C_2-C_8)$alkynyl. In another aspect of this embodiment, $R^4$ is $OR^a$ and $R^1$ is $(C_1-C_8)$alkyl, $(C_r—C_8)$ alkenyl or $(C_2-C_8)$alkynyl. In another aspect of this embodiment, $R^4$ is $OR^a$ and $R^1$ is $(C_1-C_5)$alkyl. In another aspect of this embodiment, $R^4$ is $OR^a$ and $R^1$ is methyl. In another aspect of this embodiment, $R^4$ is $OR^a$, $R^1$ is $(C_1-C_8)$alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is $(C_1-C_8)$alkyl and $R^6$ is CN, OH, or $CH_3$. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is $(C_1-C_8)$alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is $(C_1-C_8)$alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H. In another aspect of this embodiment, $R^5$ is $N_3$.

In another embodiment of Formula II, $R^5$ is H. In another aspect of this embodiment, $R^4$ is H or $OR^a$. In another aspect of this embodiment, $R^4$ is $OR^a$. In another aspect of this embodiment, $R^4$ is $OR^a$ and $R^1$ is $(C_1-C_8)$alkyl, $(C_1-C_8)$ alkenyl or $(C_2-C_8)$alkynyl. In another aspect of this embodiment, $R^4$ is $OR^a$ and $R^1$ is $(C_1-C_8)$alkyl, $(C_2-C_8)$ alkenyl or $(C_2-C_8)$ alkynyl. In another aspect of this embodiment, $R^4$ is $OR^a$ and $R^1$ is $(C_1-C_8)$alkyl. In another aspect of this embodiment, $R^4$ is $OR^a$ and $R^1$ is methyl. In another aspect of this embodiment, $R^4$ is $OR^a$, $R^1$ is $(C_1-C_8)$alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is $(C_1-C_8)$alkyl and $R^6$ is CN, OH, or $CH_3$. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is $(C_1-C_3)$alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is $(C_1-C_8)$alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula II, $R^6$ is H, CN, $OR^a$ or $CH_3$. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^E$. In another aspect of this embodiment, $R^4$ is $OR^a$ and $R^1$ is $(C_1-C_8)$alkyl, $(C_2-C_8)$ alkenyl or $(C_2-C_8)$alkynyl. In another aspect of this embodiment, $R^4$ is $OR^a$ and $R^1$ is $(C_1-C_8)$alkyl, $(C_2-C_8)$ alkenyl or $(C_2-C_8)$alkynyl. In another aspect of this embodiment, $R^4$ is $OR^a$ and $R^1$ is $(C_1-C_8)$alkyl. In another aspect of this embodiment, $R^4$ is $OR^a$ and $R^1$ is methyl. In another aspect of this embodiment, $R^4$ is $OR^a$, $R^1$ is $(C_1-C_8)$alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is $(C_1-C_8)$alkyl and $R^6$ is CN, OH, or $CH_3$. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is $(C_1-C_8)$alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is $(C_1-C_8)$alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula II, $R^6$ is CN, $OR^a$ or $CH_3$. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is $(C_1-C_8)$alkyl, $(C_2-C_8)$ alkenyl or $(C_2-C_8)$alkynyl. In another aspect of this embodiment, $R^4$ is $OR^a$ and $R^1$ is $(C_1-$ $C_8$)alkyl, ($C_2$-$C_8$) alkenyl or ($C_2$-$C_8$)alkynyl. In another aspect of this embodiment, $R^4$ is $OR^a$ and $R^1$ is ($C_1$-$C_8$)alkyl. In another aspect of this embodiment, $R^4$ is $OR^a$ and $R^1$ is methyl. In another aspect of this embodiment, $R^4$ is $OR^a R^1$ is ($C_1$-$C_8$)alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is ($C_1$-$C_8$)alkyl and $R^6$ is CN, OH, or $CH_3$ In another aspect of this embodiment, $R^4$ is $OR^a$, $R^1$ is methyl and $R^6$ is CN, OH, or $CH_3$. In another aspect of this embodiment, $R^4$ is OH and $R^1$ is methyl. In another aspect of this embodiment, $R^4$ is OH, $R^1$ is ($C_1$-$C_8$)alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is ($C_1$-$C_8$)alkyl and $R^6$ is CN, OH, or $CH_3$ In another aspect of this embodiment, $R^4$ is OH, $R^1$ is methyl and $R^6$ is CN, OH, or $CH_3$.

In one embodiment of Formula II, $R^7$ is H, —C(=O)$R^{11}$, —C(=O)$SR^{11}$ or

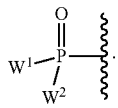

In a aspect of this embodiment, $R^7$ is H. In another aspect of this embodiment, $R^7$ is —C(=O)$R^{11}$. In another aspect of this embodiment, $R^7$ is —C(=O)$R^{11}$ wherein $R^{11}$ is ($C_1$-$C_3$) alkyl. In another aspect of this embodiment, $R^7$ is

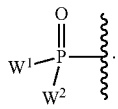

In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is ($C_1$-$C_8$)alkyl, ($C_2$-$C_8$) alkenyl or ($C_2$-$C_8$)alkynyl. In another aspect of this embodiment, $R^4$ is $OR^a$ and $R^1$ is ($C_1$-$C_8$)alkyl. In another aspect of this embodiment, $R^4$ is $OR^a$ and $R^1$ is methyl. In another aspect of this embodiment, $R^4$ is $OR^a$, $R^1$ is ($C_1$-$C_8$)alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is ($C_1$-$C_8$) alkyl and $R^6$ is CN, OH, or $CH_3$ In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is ($C_1$-$C_8$)alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is ($C_1$-$C_8$)alkyl and $R^6$ is CN, OH, or $CH_3$ In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In one embodiment of Formula II, $X^1$ is N or C—$R^{10}$. In another aspect of this embodiment, $X^1$ is N. In another aspect of this embodiment, $X^1$ is C—$R^{10}$. In another aspect of this embodiment, $X^2$ is C—H. In another aspect of this embodiment, $X^1$ is N and $X^2$ is C—H. In another aspect of this embodiment, $X^1$ is C—$R^{10}$ and $X^2$ is CH. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is ($C_1$-$C_8$)alkyl, ($C_2$-$C_8$) alkenyl or ($C_2$-$C_8$)alkynyl. In another aspect of this embodiment, $R^4$ is $OR^a$ and $R^1$ is ($C_1$-$C_8$)alkyl. In another aspect of this embodiment, $R^4$ is $OR^a$ and $R^1$ is methyl. In another aspect of this embodiment, $R^4$ is $OR^a$, $R^1$ is ($C_1$-$C_8$)alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is ($C_1$-$C_8$) alkyl and $R^6$ is CN, OH, or $CH_3$ In another aspect of this embodiment, $R^4$ is $OR^a$, $R^1$ is methyl and $R^6$ is CN, OH, or $CH_3$. In another aspect of this embodiment, $R^4$ is OH and $R^1$ is methyl. In another aspect of this embodiment, $R^4$ is OH, $R^1$ is ($C_1$-$C_8$)alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is ($C_1$-$C_8$)alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula II, each $R^8$ is independently halogen, $NR^{11}R^{12}$, $N(R^{11})OR^{11}$, $NR^{11}NR^{11}R^{12}$, $OR^{11}$ or $SR^{11}$. In another aspect of this embodiment, $R^1$ is methyl, $CH_2F$ or ethynyl. In another aspect of this embodiment, $R^1$ is methyl. In another aspect of this embodiment, $R^9$ is H, halogen, or $NR^{11}R^{12}$. In another aspect of this embodiment, $R^9$ is H, halogen, or $NR^{11}R^{12}$ and $R^1$ is methyl, $CH_2F$, or ethynyl. In another aspect of this embodiment, $R^9$ is H, halogen, or $NR^{11}R^{12}$ and $R^1$ is methyl. In another aspect of this embodiment, $R^8$ is $NH_2$ and $R^9$ is H or halogen. In another aspect of this embodiment, $R^8$ is $NH_2$ and $R^9$ is H or halogen and $R^1$ is methyl, $CH_2F$, or ethynyl. In another aspect of this embodiment, $R^8$ is $NH_2$ and $R^9$ is H or halogen and $R^1$ is methyl. In another aspect of this embodiment, $R^8$ and $R^9$ are each $NH_2$. In another aspect of this embodiment, $R^8$ and $R^9$ are each $NH_2$ and $R^1$ is methyl. In another aspect of this embodiment, $R^8$ and $R^9$ are each $NH_2$ and $R^1$ is methyl, $CH_2F$ or ethynyl. In another aspect of this embodiment, $R^8$ is OH and $R^9$ is $NH_2$. In another aspect of this embodiment, $R^8$ is OH, $R^9$ is $NH_2$ and $R^1$ is methyl. In another aspect of this embodiment, $R^8$ is OH, $R^9$ is $NH_2$ and $R^1$ is methyl, $CH_2F$, or ethynyl. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is ($C_1$-$C_8$)alkyl, ($C_2$-$C_8$) alkenyl or ($C_2$-$C_8$)alkynyl. In another aspect of this embodiment, $R^4$ is $OR^a$ and $R^1$ is ($C_1$-$C_8$)alkyl. In another aspect of this embodiment, $R^4$ is $OR^a$ and $R^1$ is methyl. In another aspect of this embodiment, $R^4$ is $OR^a$, $R^1$ is ($C_1$-$C_8$)alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is ($C_1$-$C_8$) alkyl and $R^6$ is CN, OH, or $CH_3$. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is ($C_1$-$C_8$)alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is ($C_1$-$C_8$)alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula II, each $R^{10}$ is, independently, H, halogen, CN or optionally substituted heteroaryl. In another aspect of this embodiment, $R^1$ is methyl. In another aspect of this embodiment, $R^1$ is methyl, $CH_2F$ or ethynyl. In another aspect of this embodiment, $R^9$ is H, halogen, or $NR^{11}R^{12}$. In another aspect of this embodiment, $R^9$ is H, halogen, or $NR^{11}R^{12}$ and $R^1$ is methyl. In another aspect of this embodiment, $R^9$ is H, halogen, or $NR^{11}R^{12}$ and $R^1$ is methyl, $CH_2F$, or ethynyl. In another aspect of this embodiment, $R^8$ is $NH_2$ and $R^9$ is H or halogen. In another aspect of this embodiment, $R^8$ is $NH_2$ and $R^9$ is H or halogen and $R^1$ is methyl. In another aspect of this embodiment, $R^8$ is $NH_2$ and $R^9$ is H or halogen and $R^1$ is methyl, $CH_2F$, or ethynyl. In another aspect of this embodiment, $R^8$ and $R^9$ are each $NH_2$. In another aspect of this embodiment, $R^8$ and $R^9$ are each $NH_2$ and $R^1$ is methyl. In another aspect of this embodiment, $R^8$ and $R^9$ are each $NH_2$ and $R^1$ is methyl, $CH_2F$ or ethynyl. In another aspect of this embodiment, $R^8$ is OH and $R^9$ is $NH_2$. In another aspect of this embodiment, $R^8$ is OH, $R^9$ is $NH_2$ and $R^1$ is methyl. In another aspect of this embodiment, $R^8$ is OH, $R^9$ is $NH_2$ and $R^1$ is methyl, $CH_2F$, or ethynyl. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is $(C_1-C_8)$alkyl, $(C_2-C_8)$alkenyl or $(C_2-C_8)$alkynyl. In another aspect of this embodiment, $R^4$ is $OR^a$ and $R^1$ is $(C_1-C_8)$alkyl. In another aspect of this embodiment, $R^4$ is $OR^a$ and $R^1$ is methyl. In another aspect of this embodiment, $R^4$ is $OR^a$, $R^1$ is $(C_1-C_8)$alkyl and at least one of $X^1$ or $X^2$ is N. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is $(C_1-C_8)$alkyl and $R^6$ is CN, OH, or $CH_3$. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is $(C_1-C_8)$alkyl and at least one of $X^1$ or $X^2$ is N. In another aspect of this embodiment, $R^4$ is OH, $R^1$ is methyl and at least one of $X^1$ or $X^2$ is N. In another aspect of this embodiment, $R^4$ is OH, $R^1$ is $(C_1-C_8)$alkyl and $R^6$ is CN, OH, or $CH_3$. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment, compounds of Formula I or Formula II are represented by Formula III:

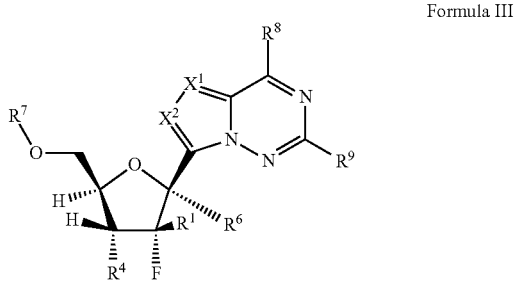

Formula III or a pharmaceutically acceptable salt, thereof;
wherein:
$R^1$ is $CH_3$, $CH_2F$, or ethynyl and all remaining variables are defined as for Formula I.

In one embodiment of Formula III, $R^4$ is H, $OR^a$, $N(R^a)_2$, $N_3$, CN, $SR^a$, halogen, $(C_1-C_8)$alkyl, $(C_2-C_8)$alkenyl or $(C_2-C_8)$alkynyl. In another aspect of this embodiment, $R^4$ is H or $OR^a$. In another aspect of this embodiment, $R^4$ is $OR^a$. In another aspect of this embodiment, $R^4$ is $OR^a$ and $R^1$ is $CH_3$, $CH_2F$, or ethynyl. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment; $R^4$ is OH, $R^1$ is methyl and at least one of $X^1$ or $X^2$ is N. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula III, $R^6$ is H, CN, $OR^a$ or $CH_3$. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is OH, $R^1$ is methyl and $R^6$ is CN, OH, or $C_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is methyl and at least one of $X^1$ or $X^2$ is N. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula III, $R^6$ is CN, $OR^a$ or $CH_3$. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is O1e, $R^1$ is methyl and $R^6$ is CN, OH, or $CH_3$. In another aspect of this embodiment, $R^4$ is OH and $R^1$ is methyl. In another aspect of this embodiment, $R^4$ is OH, $R^1$ is methyl and at least one of $X^1$ or $X^2$ is N. In another aspect of this embodiment, $R^4$ is OH, $R^1$ is methyl and $R^6$ is CN, OH, or $CH_3$.

In one embodiment of Formula III, $R^7$ is H, —C(=O)$R^{11}$, —C(=O)O$R^{11}$, —C(=O)S$R^{11}$ or

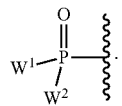

In a aspect of this embodiment, $R^7$ is H. In another aspect of this embodiment, $R^7$ is —C(=O)$R^{11}$. In another aspect of this embodiment, $R^7$ is —C(=O)$R^{11}$ wherein $R^{11}$ is $(C_1-C_8)$ alkyl. In another aspect of this embodiment, $R^7$ is

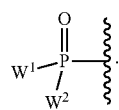

In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is methyl and $R^6$ is CN, OH, or $CH_3$. In another aspect of this embodiment, $R^4$ is $OR^E$, $R^1$ is methyl and $R^6$ is H. In another aspect of this embodiment, $R^4$ is OH and $R^1$ is methyl. In another aspect of this embodiment, $R^4$ is OH, $R^1$ is methyl and at least one of $X^1$ or $X^2$ is N. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In one embodiment of Formula III, $X^1$ is N or C—$R^{10}$. In another aspect of this embodiment, $X^1$ is N. In another aspect of this embodiment, $X^1$ is C—$R^{10}$. In another aspect of this embodiment, $X^2$ is C—H. In another aspect of this embodiment, $X^1$ is N and $X^2$ is C—H. In another aspect of this embodiment, $X^1$ is C—$R^{10}$ and $X^2$ is CH. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is methyl and $R^6$ is CN, OH, or $CH_3$. In another aspect of this embodiment, $R^4$ is OH and $R^1$ is methyl. In another aspect of this embodiment, $R^4$ is OH, $R^1$ is methyl and at least one of $X^1$ or $X^2$ is N. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In another embodiment of Formula III, each $R^8$ is independently halogen, $NR^{11}R^{12}$, $N(R^{11})OR^{11}$, $NR^{11}NR^{11}R^{12}$, $OR^{11}$ or $SR^{11}$. In another aspect of this embodiment, $R^1$ is methyl, $CH_2F$ or ethynyl. In another aspect of this embodiment, $R^1$ is methyl. In another aspect of this embodiment, $R^9$ is H, halogen, or $NR^{11}R^{12}$. In another aspect of this embodiment, $R^9$ is H, halogen, or $NR^{11}R^{12}$ and $R^1$ is methyl, $CH_2F$, or ethynyl. In another aspect of this embodiment, $R^9$ is H, halogen, or $NR^{11}R^{12}$ and $R^1$ is methyl. In another aspect of this embodiment, $R^8$ is $NH_2$ and $R^9$ is H or halogen. In another aspect of this embodiment, $R^8$ is $NH_2$ and $R^9$ is H or halogen and $R^1$ is methyl, $CH_2F$, or ethynyl. In another aspect of this embodiment, $R^8$ is $NH_2$ and $R^9$ is H or halogen and $R^1$ is methyl. In another aspect of this embodiment, $R^8$ and $R^9$ are each $NH_2$. In another aspect of this embodiment, $R^8$ and $R^9$ are each $NH_2$ and $R^1$ is methyl, $CH_2F$ or ethynyl. In another aspect of this embodiment, $R^8$ and $R^9$ are each $NH_2$ and $R^1$ is methyl. In another aspect of this embodiment, $R^8$ is OH and $R^9$ is $NH_2$. In another aspect of this embodiment, $R^8$ is OH, $R^9$ is $NH_2$ and $R^1$ is methyl, $CH_2F$, or ethynyl. In another aspect of this embodiment, $R^8$ is OH, $R^9$ is $NH_2$ and $R^1$ is methyl. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is methyl and $R^6$ is CN, OH, or $CH_3$. In another aspect of this embodiment, $R^4$ is OH and $R^1$ is methyl. In another aspect of this embodiment, $R^4$ is OH, $R^1$ is methyl and at least one of $X^1$ or $X^2$ is N. In another aspect of this embodiment, $R^4$ is OH, $R^1$ is methyl and $R^6$ is CN. OH, or $CH_3$. In another aspect of this embodiment, $R^4$ is OH, $R^1$ is methyl and $R^6$ is H.

In another embodiment of Formula III, each $R^{10}$ is, independently, H, halogen, CN or optionally substituted heteroaryl. In another aspect of this embodiment, $R^1$ is methyl. In another aspect of this embodiment, $R^9$ is H, halogen, or $NR^{11}R^{12}$. In another aspect of this embodiment, $R^9$ is H, halogen, or $NR^{11}R^{12}$ and $R^1$ is methyl. In another aspect of this embodiment, $R^8$ is $NH_2$ and $R^9$ is H or halogen. In another aspect of this embodiment, $R^8$ is $NH_2$ and $R^9$ is H or halogen and $R^1$ is methyl. In another aspect of this embodiment, $R^8$ and $R^9$ are each $NH_2$. In another aspect of this embodiment, $R^8$ and $R^9$ are each $NH_2$ and $R^1$ is methyl. In another aspect of this embodiment, $R^8$ is OH and $R^9$ is $NH_2$. In another aspect of this embodiment, $R^8$ is OH, $R^9$ is $NH_2$ and $R^1$ is methyl. In another aspect of this embodiment $R^6$ is H. In another aspect of this embodiment $R^6$ is CN. In another aspect of this embodiment $R^6$ is $OR^a$. In another aspect of this embodiment $R^6$ is OH. In another aspect of this embodiment $R^6$ is $CH_3$. In another aspect of this embodiment, $R^4$ is H or $OR^a$. In another aspect of this embodiment, $R^4$ is $OR^a$ and $R^1$ is methyl. In another aspect of this embodiment, $R^4$ is $OR^a$, $R^1$ is methyl and at least one of $X^1$ or $X^2$ is N. In another aspect of this embodiment, $R^4$ is $OR^a$, $R^1$ is methyl and $R^6$ is CN, OH, or $CH_3$. In another aspect of this embodiment, $R^4$ is $OR^a$, $R^1$ is methyl and $R^6$ is H. In another aspect of this embodiment, $R^4$ is OH and $R^1$ is methyl. In another aspect of this embodiment, $R^4$ is OH, $R^1$ is methyl and at least one of $X^1$ or $X^2$ is N. In another aspect of this embodiment, $R^4$ is OH, $R^1$ is methyl and $R^6$ is CN, OH, or $CH_3$. In another aspect of this embodiment, $R^4$ is OH, $R^1$ is methyl and $R^6$ is H.

In one embodiment of Formulas I-III, $R^{11}$ or $R^{12}$ is independently H, $(C_1$-$C_8)$alkyl, $(C_2$-$C_8)$alkenyl, $(C_2$-$C_8)$alkynyl, $(C_4$-$C_8)$carbocyclylalkyl, optionally substituted aryl, optionally substituted heteroaryl, —C(=O)($C_1$-$C_8$)alkyl, —S(O)$_n$($C_1$-$C_8$)alkyl or aryl($C_1$-$C_8$)alkyl. In another embodiment, $R^{11}$ and $R^{12}$ taken together with a nitrogen to which they are both attached, form a 3 to 7 membered heterocyclic ring wherein any one carbon atom of said heterocyclic ring can optionally be replaced with —O—, —S— or —$NR^a$—. Therefore, by way of example and not limitation, the moiety —$NR^{11}R^{12}$ can be represented by the heterocycles:

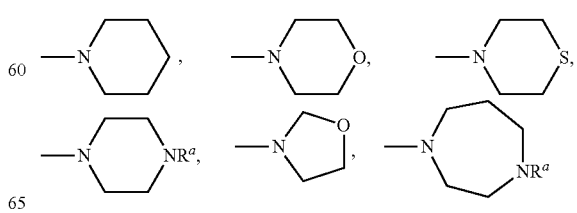

and the like.

In another embodiment of Formulas I-III, each $R^3$, $R^4$, $R^5$, $R^6$, $R^{11}$ or $R^{12}$ is, independently, $(C_1-C_8)$alkyl, $(C_2-C_8)$alkenyl, $(C_2-C_8)$alkynyl or aryl$(C_1-C_8)$alkyl, wherein said $(C_1-C_8)$alkyl, $(C_2-C_8)$alkenyl, $(C_2-C_8)$alkynyl or aryl$(C_1-C_8)$alkyl are, independently, optionally substituted with one or more halo, hydroxy, CN, $N_3$, $N(R^a)_2$ or $OR^a$. Therefore, by way of example and not limitation, $R^3$, $R^4$, $R^5$, $R^6$, $R^{11}$ or $R^{12}$ could represent moieties such as —CH(NH$_2$)CH$_3$, —CH(OH)CH2CH3, —CH(NH$_2$)CH(CH$_3$)$_2$, —CH$_2$CF$_3$, —(CH$_2$)$_2$CH(N$_3$)CH$_3$, —(CH$_2$)$_6$NH$_2$ and the like.

In another embodiment of Formula I-III, $R^3$, $R^4$, $R^5$, $R^6$, $R^{11}$ or $R^{12}$ is $(C_1-C_8)$alkyl wherein one or more of the non-terminal carbon atoms of each said $(C_1-C_8)$alkyl may be optionally replaced with —O—, —S— or —NR$^a$—. Therefore, by way of example and not limitation, $R^3$, $R^4$, $R^5$, $R^6$, $R^{11}$ or $R^{12}$ could represent moieties such as —CH$_2$OCH$_3$, —CH$_2$OCH$_2$CH$_3$, —CH$_2$OCH(CH$_3$)$_2$, —CH$_2$SCH$_3$, —(CH$_2$)$_6$OCH$_3$, —(CH$_2$)$_6$N(CH$_3$)$_2$ and the like.

In another embodiment, Formulas I-III is a compound selected from the group consisting of

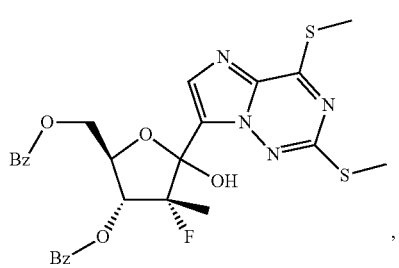

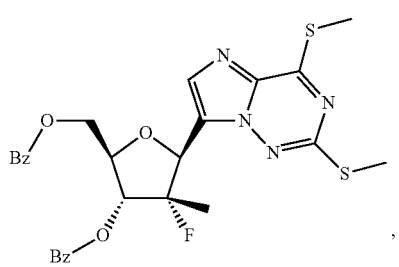

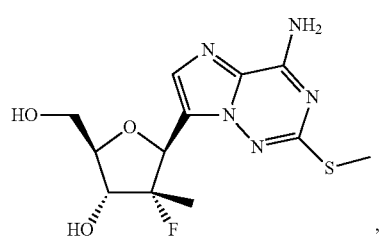

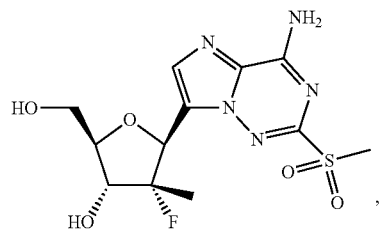

-continued

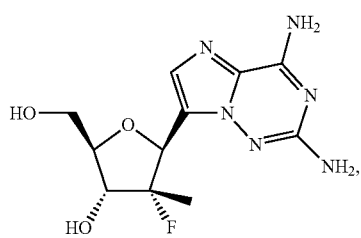

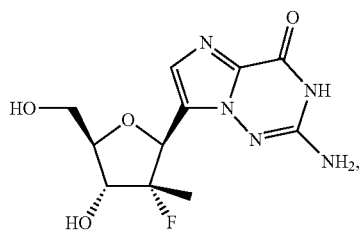

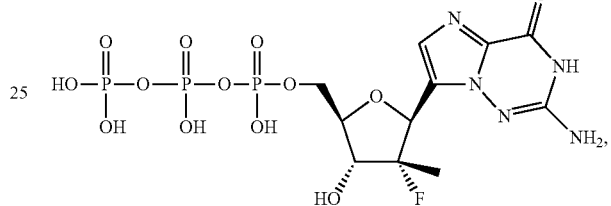

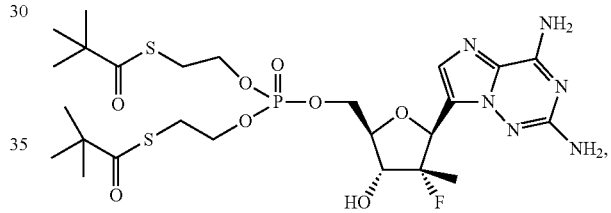

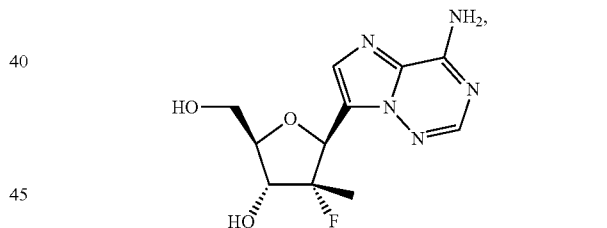

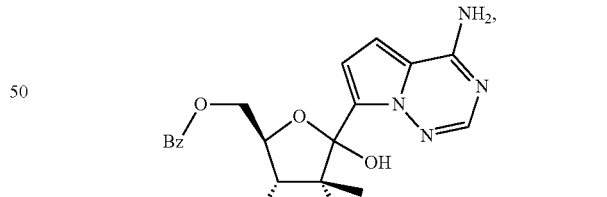

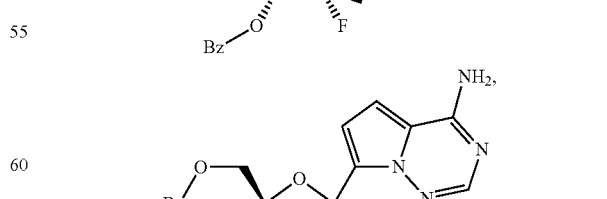

-continued
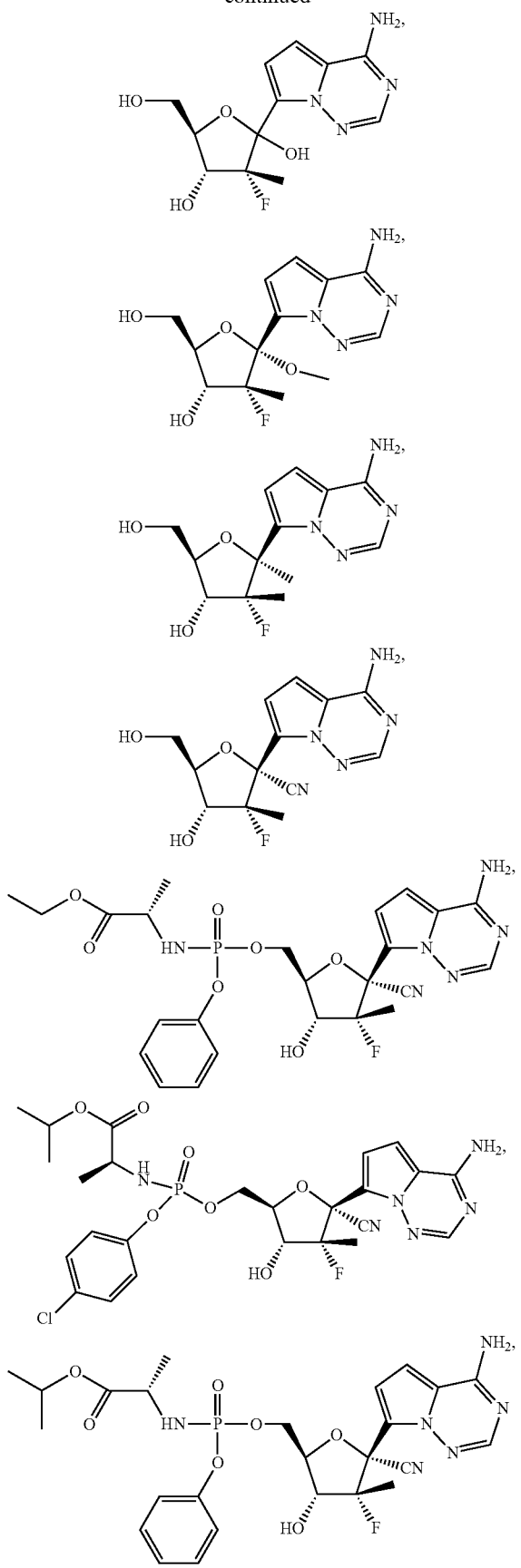
-continued
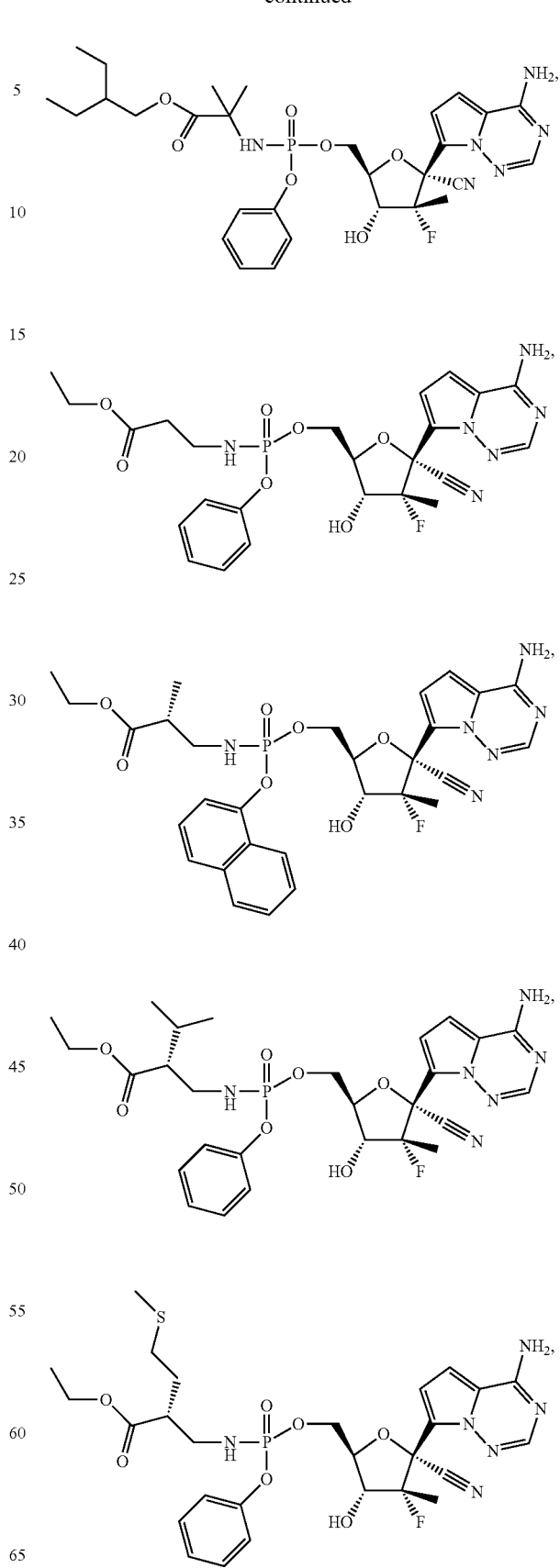

21
-continued
22
-continued
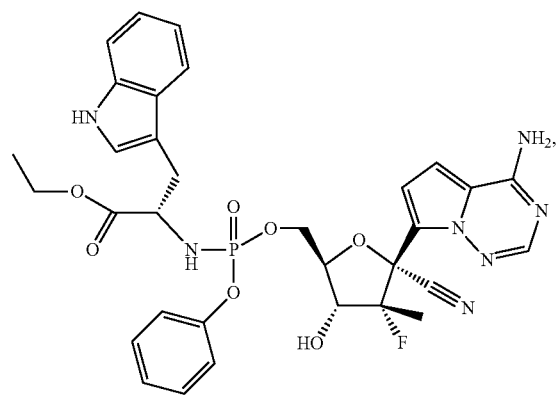
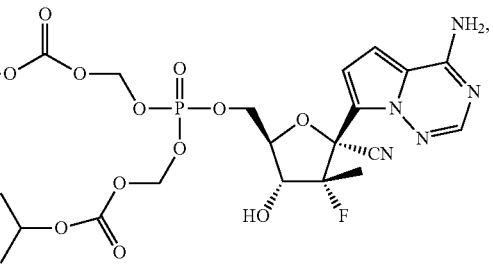
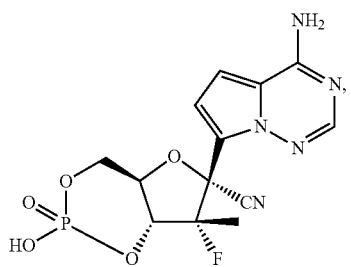
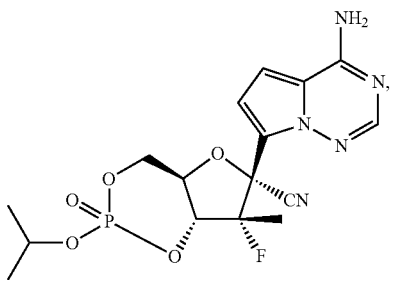
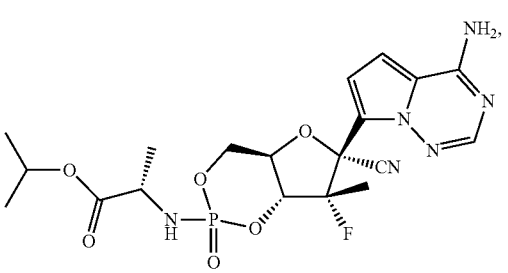
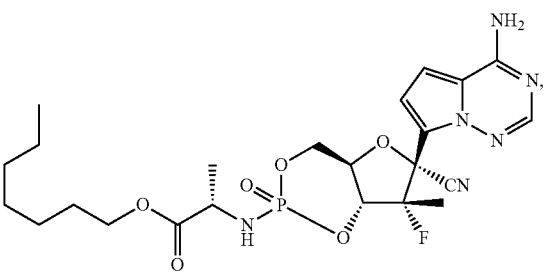
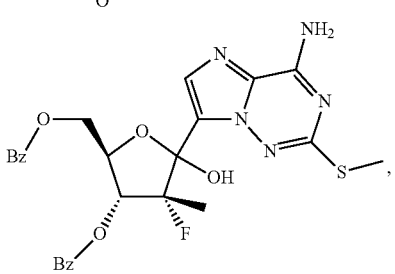

23
-continued
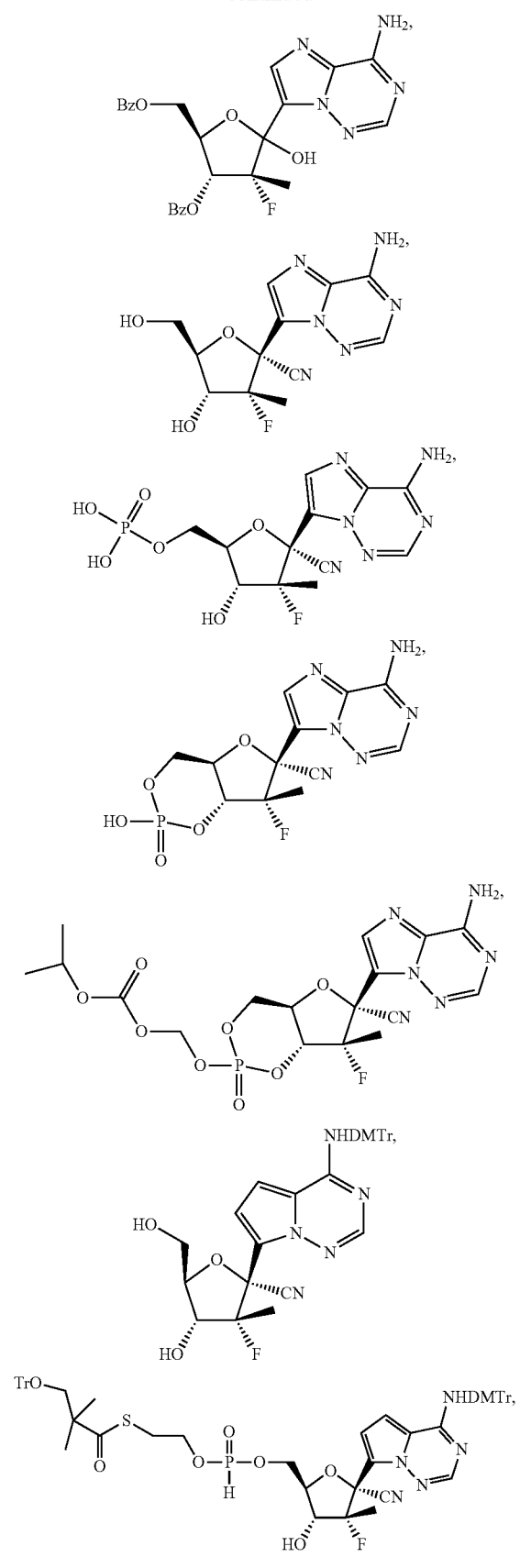
24
-continued
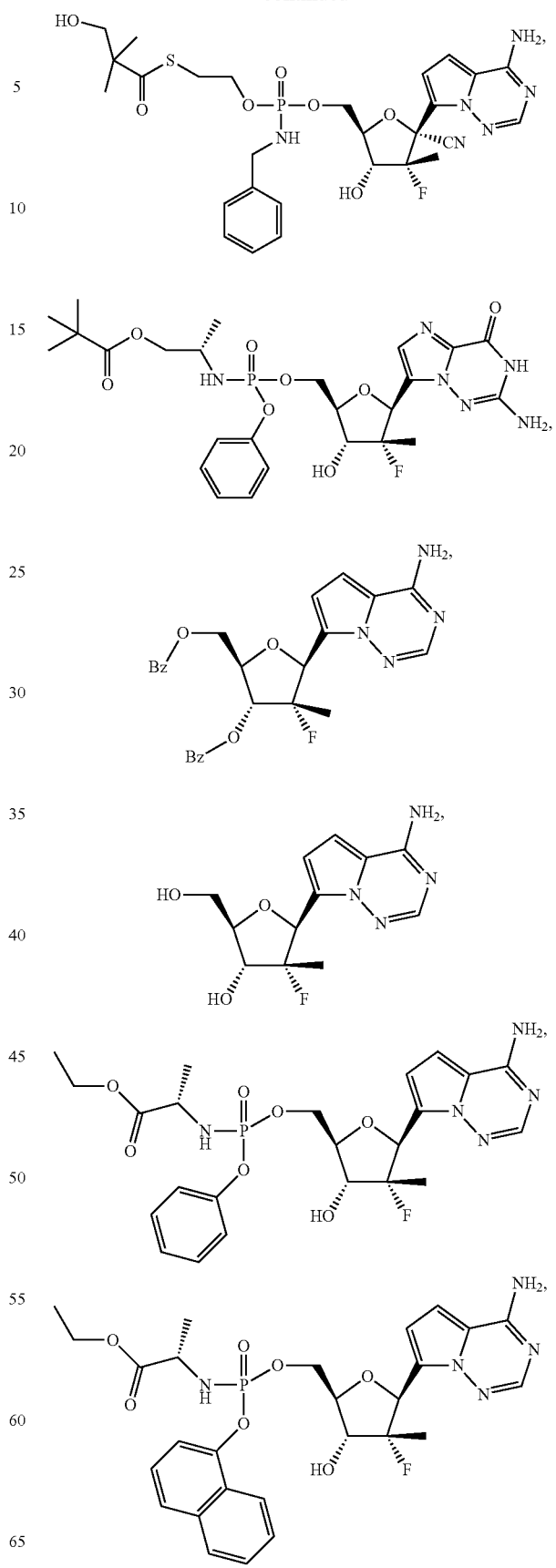

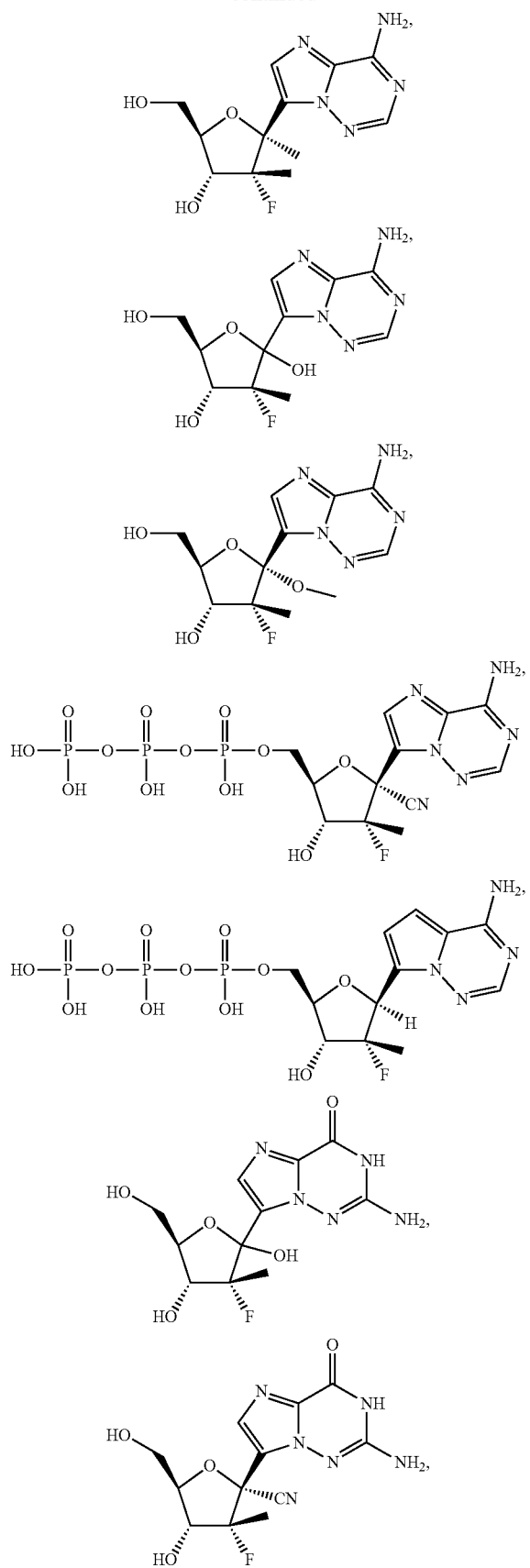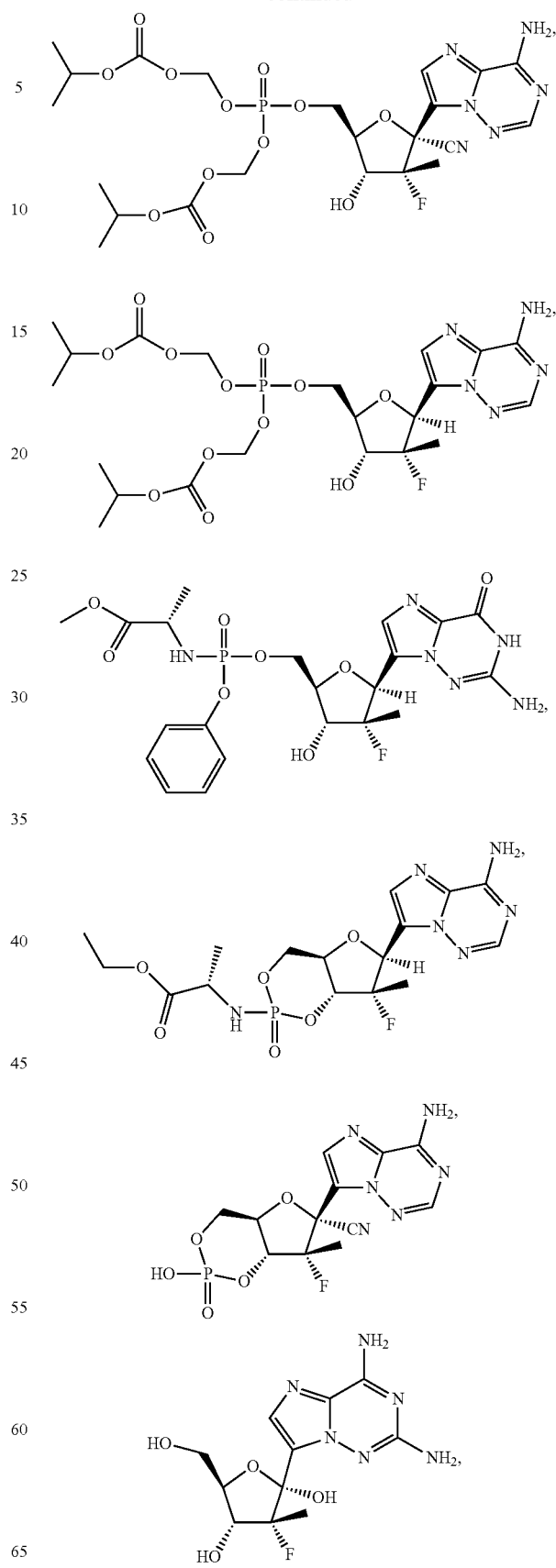

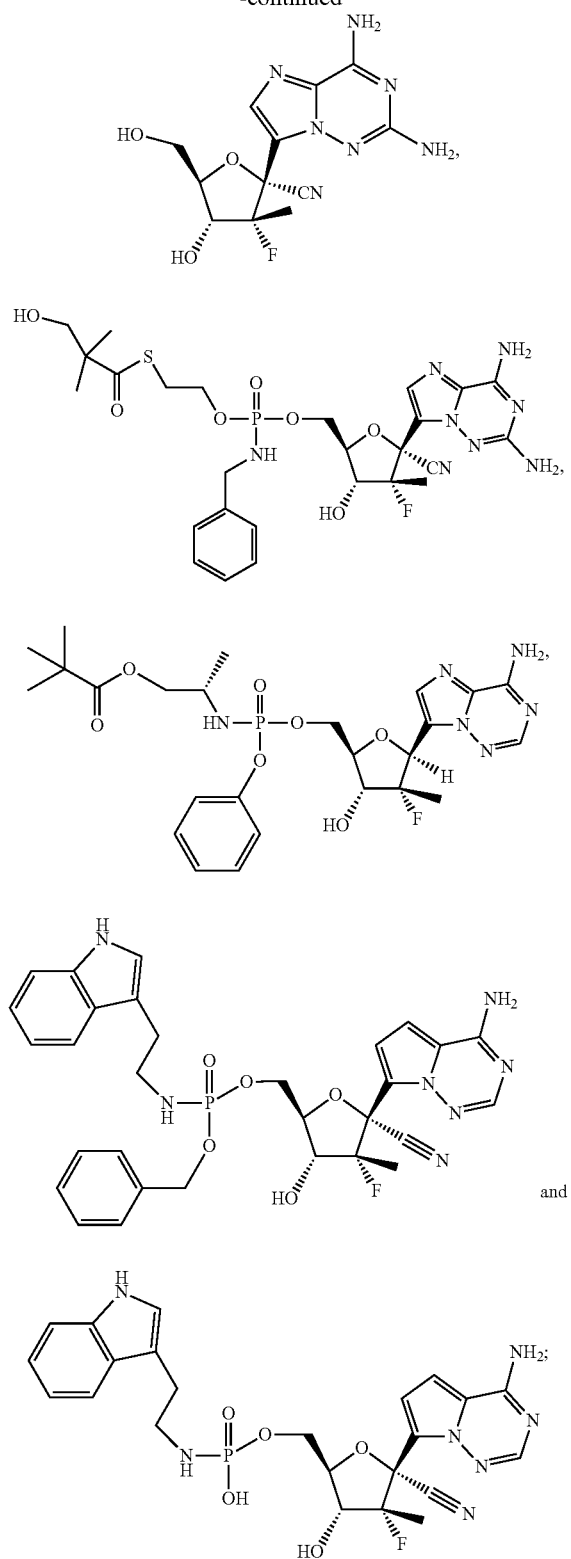
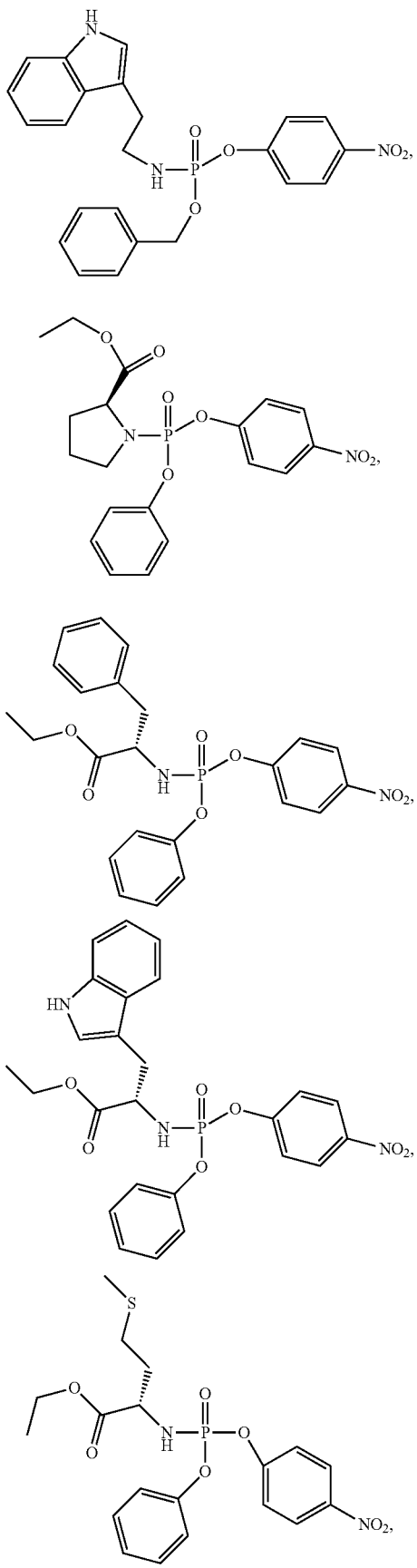
or a pharmaceutically acceptable salt or ester thereof.
In another embodiment, provided is a compound useful for the synthesis of the compounds of Formula I selected from the group consisting of

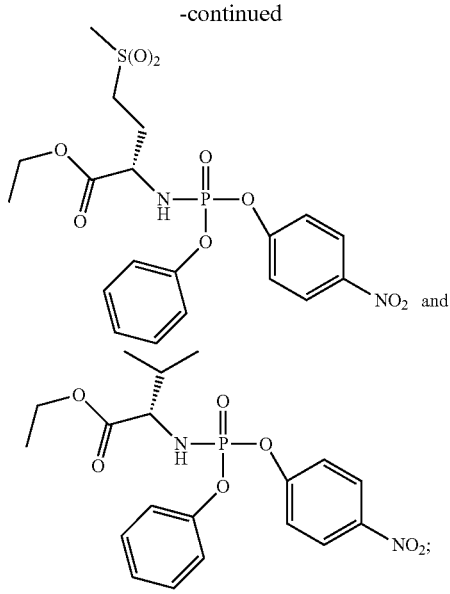

or salts or esters thereof.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_1$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—$CH_2$C≡C—), and 4-pentynyl (—$CH_2CH_2CH_2$C≡C—).

"Amino" refers generally to a nitrogen radical which can be considered a derivative of ammonia, having the formula —$N(X)_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —$N(alkyl)_2$, —NH(alkyl), —$N(carbocyclyl)_2$, NH(carbocyclyl), —$N(heterocyclyl)_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl", unless otherwise indicated, means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b{}_2$, —N$^+$R$^b{}_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b{}_2$, —S(=O)$_2$—, —S(=O)$_2$OH, —S(=O)$_2$R$^b$, —OS(=O)$_2$OR$^b$, —S(=O)$_2$NR$^b{}_2$, —S(=O)R$^b$, —OP(=O)(OR$^b$)$_2$, —P(=O)(OR$^b$)$_2$, —P(=O)(O$^-$)$_2$, —P(=O)(OH)$_2$, —P(O)(OR$^b$)(O), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b{}_2$, —C(S)NR$^b{}_2$, —C(=NR$^b$)NR$^b{}_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-III should be selected in order to provide a compound which is sufficiently stable to provide a pharmaceutically useful compound which can be formulated into an acceptably stable pharmaceutical composition. The definitions and substituents for various genus and subgenus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in. Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

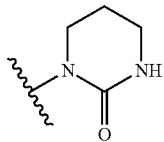

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromenyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

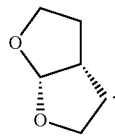

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH₂-pyridinyl, —CH₂-pyrrolyl, —CH₂-oxazolyl, —CH₂-indolyl, —CH₂-isoindolyl, —CH₂-purinyl, —CH₂-furanyl, —CH₂-benzofuranyl, —CH₂-benzothiophenyl, —CH₂-carbazolyl, —CH₂-thiazolyl, —CH₂-isoxazolyl, —CH₂-pyrazolyl, —CH₂-isothiazolyl, —CH₂-quinolyl, —CH₂-isoquinolyl, —CH₂-pyridazyl, —CH₂-pyrimidyl, —CH₂-pyrazyl, —CH(CH₃)-pyridinyl, —CH(CH₃)-pyrrolyl, —CH(CH₃)-oxazolyl, —CH(CH₃)-indolyl, —CH(CH₃)-isoindolyl, —CH(CH₃)-purinyl, —CH(CH₃)-furanyl, —CH(CH₃)-thienyl, —CH(CH₃)-benzofuranyl, —CH(CH₃)-benzothiophenyl, —CH(CH₃)-carbazolyl, —CH(CH₃)-imidazolyl, —CH(CH₃)-thiazolyl, —CH(CH₃)-isoxazolyl, —CH(CH₃)-pyrazolyl, —CH(CH₃)-isothiazolyl, —CH(CH₃)-quinolyl, —CH(CH₃)-isoquinolyl, —CH(CH₃)-pyridazyl, —CH(CH₃)-pyrimidyl, —CH(CH₃)-pyrazyl, etc.

The term "optionally substituted" in reference to a particular moiety of the compound of Formula I-III (e.g., an optionally substituted aryl group) refers to a moiety wherein all substitutes are hydrogen or wherein one or more of the hydrogens of the moiety may be replaced by substituents such as those listed under the definition of "substituted" or as otherwise indicated.

The term "optionally replaced" in reference to a particular moiety of the compound of Formula I-III (e.g., the carbon atoms of said (C₁-C₈)alkyl may be optionally replaced by —O—, —S—, or —NRᵃ—) means that one or more of the methylene groups of the (C₁-C₈)alkyl may be replaced by 0, 1, 2, or more of the groups specified (e.g., —O—, —S—, or —NRᵃ—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH₂(C*)H₂(C*)H₂CH₃ or alkylene moiety —CH₂(C*)H₂(C*)H₂CH₂— the C* atoms would be considered to be the non-terminal carbon atoms.

Certain Y and Y¹ alternatives are nitrogen oxides such as ⁺N(O)(R) or ⁺N(O)(OR). These nitrogen oxides, as shown here attached to a carbon atom, can also be represented by charge separated groups such as

respectively, and are intended to be equivalent to the aforementioned representations for the purposes of describing this invention.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked" mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

Unless otherwise specified, the carbon atoms of the compounds of Formula I-III are intended to have a valence of four. In some chemical structure representations where carbon atoms do not have a sufficient number of variables attached to produce a valence of four, the remaining carbon substitutents needed to provide a valence of four should be assumed to be hydrogen. For example,

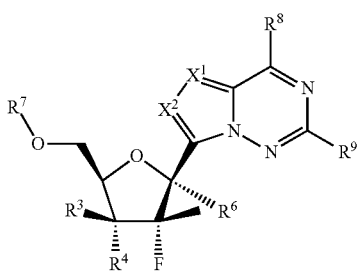

has the same meaning as

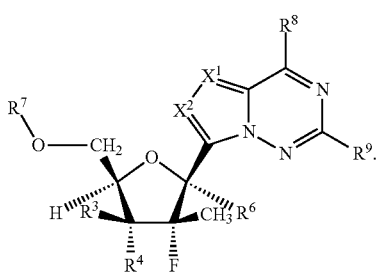

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

A prodrug moiety may include an active metabolite or drug itself.

Exemplary prodrug moieties include the hydrolytically sensitive or labile acyloxymethyl esters —$CH_2OC(=O)R^{30}$ and acyloxymethyl carbonates —$CH_2OC(=O)OR^{30}$ where $R^{30}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was used as a prodrug strategy for carboxylic acids and then applied to phosphates and phosphonates by Farquhar et al (1983) *J. Pharm. Sci.* 72: 324; also U.S. Pat. Nos. 4,816,570, 4,968,788, 5,663,159 and 5,792,756. In certain compounds of the invention, a prodrug moiety is part of a phosphate group. The acyloxyalkyl ester may be used to deliver phosphoric acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

The phosphate group may be a phosphate prodrug moiety. The prodrug moiety may be sensitive to hydrolysis, such as, but not limited to those comprising a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert et al (1.994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans.* 1 2345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al (1993) *Antiviral Res.*, 22: 155-174; Benzaria et al (1996) *J. Med. Chem.* 39: 4958). Cyclic phosphonate esters have also been described as prodrugs of phosphorus-containing compounds (Erion et al, U.S. Pat. No. 6,312,662).

It is to be noted that all enantiomers, diastereomers, and racemic mixtures, tautomers, polymorphs, pseudopolymorphs of compounds within the scope of Formula I, Formula II, or Formula III and pharmaceutically acceptable salts thereof are embraced by the present invention. All mixtures of such enantiomers and diastereomers are within the scope of the present invention.

A compound of Formula I-III and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-III and their pharmaceutically acceptable salts.

A compound of Formula I-III and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-III and their pharmaceutically acceptable salts.

Selected substituents comprising the compounds of Formula I-III are present to a recursive degree. In this context, "recursive substituent" means that a substituent may recite another instance of itself. Because of the recursive nature of such substituents, theoretically, a large number of compounds may be present in any given embodiment. For example, $R^x$ comprises a $R^y$ substituent. $R^y$ can be R. R can be $W^3$. $W^3$ can be $W^4$ and $W^4$ can be R or comprise substituents comprising $R^y$. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

By way of example and not limitation, $W^3$ and $R^y$ are recursive substituents in certain embodiments. Typically, each recursive substituent can independently occur 20, 19, 18, 17, 16, 15, 14, 13, 12, 11, 10, 9, 8, 7, 6, 5, 4, 3, 2, 1, or 0, times in a given embodiment. More typically, each recursive substituent can independently occur 12 or fewer times in a given embodiment. Even more typically, each recursive substituent can independently occur 3 or fewer times in a given embodiment. For example, $W^3$ will occur 0 to 8 times, $R^y$ will occur 0 to 6 times in a given embodiment. Even more typically, $W^3$ will occur 0 to 6 times and $R^y$ will occur 0 to 4 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

The modifier "about" used in connection with a quantity is inclusive of the stated value and has the meaning dictated by the context (e.g., includes the degree of error associated with measurement of the particular quantity).

The compounds of the Formula I-III may comprise a phosphate group as $R^7$, which may be a prodrug moiety

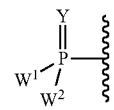

wherein each Y or $Y^1$ is, independently, O, S, NR, $^+N(O)(R)$, N(OR), $^+N(O)(OR)$, or N—NR$_2$; $W^1$ and $W^2$, when taken together, are —$Y^3(C(R^y)_7)_3Y^3$—; or one of $W^1$ or $W^2$ together with either $R^3$ or $R^4$ is —$Y^3$— and the other of $W^1$ or $W^2$ is Formula Ia; or $W^1$ and $W^2$ are each, independently, a group of Formula Ia:

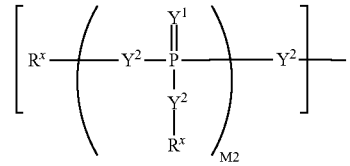

wherein:

each $Y^2$ is independently a bond, O, CR$_2$, NR, $^+N(O)(R)$, N(OR), $^+N(O)(OR)$, N—NR$_2$, S, S—S, S(O), or S(O)$_2$;

each $Y^3$ is independently O, S, or NR;

M2 is 0, 1 or 2;

each $R^y$ is independently H, F, Cl, Br, I, OH, R, —C(=$Y^1$)R, —C(=$Y^1$)OR, —C(=$Y^1$)N(R)$_2$, —N(R)$_2$, —$^+N(R)_3$, —SR, —S(O)R, —S(O)$_2$R, —S(O)(OR), —S(O)$_2$(OR), —OC(=$Y^1$)R, —OC(=$Y^1$)OR, —OC(=$Y^1$)(N(R)$_2$), —SC(=$Y^1$)R, —SC(=$Y^1$)OR, —SC(=$Y^1$)(N(R)$_2$), —N(R)C(=$Y^1$)R, —N(R)C(=$Y^1$)OR, or —N(R)C(=$Y^1$)N(R)$_2$, —SO$_2$NR$_2$, —CN, —N$_3$, —NO$_2$, —OR, a protecting group or $W^3$; or when taken together, two $R^y$ on the same carbon atom form a carbocyclic ring of 3 to 7 carbon atoms;

each $R^x$ is independently $R^y$, a protecting group, or the formula:

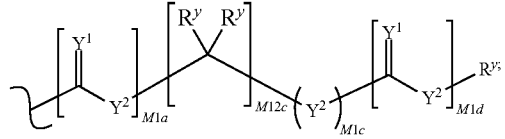

wherein:

M1a, M1e, and M1d are independently 0 or 1;

M12c is 0, 1, 2, 3, 4, 5, 6, 7, 8, 9, 10, 11 or 12;

each R is H, halogen, $(C_1-C_8)$ alkyl, $(C_1-C_8)$ substituted alkyl, $(C_2-C_8)$ alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocycle, $C_2-C_{20}$ substituted heterocyclyl, arylalkyl, substituted arylalkyl or a protecting group;

$W^3$ is $W^4$ or $W^5$; $W^4$ is R, $-C(Y^1)R^y$, $-C(Y^1)W^5$, $-SO_2R^y$, or $-SO_2W^5$; and $W^5$ is a carbocycle or a heterocycle wherein $W^5$ is independently substituted with 0 to 3 $R^y$ groups.

$W^5$ carbocycles and $W^5$ heterocycles may be independently substituted with 0 to 3 $R^y$ groups. $W^5$ may be a saturated, unsaturated or aromatic ring comprising a mono- or bicyclic carbocycle or heterocycle. $W^5$ may have 3 to 10 ring atoms, e.g., 3 to 7 ring atoms. The $W^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, (uranyl, thiofuranyl, thienyl, and pyrrolyl. $W^5$ also includes, but is not limited to, examples such as:

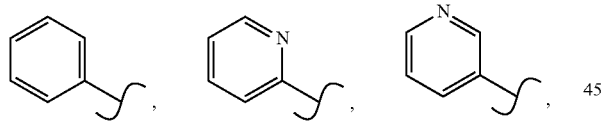

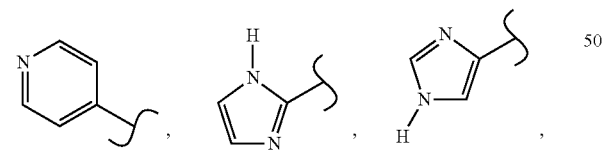

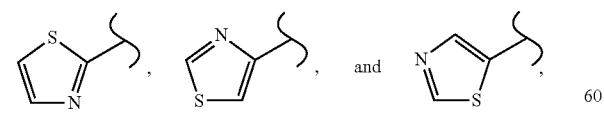

$W^5$ carbocycles and heterocycles may be independently substituted with 0 to 3 R groups, as defined above. For example, substituted $W^5$ carbocycles include:

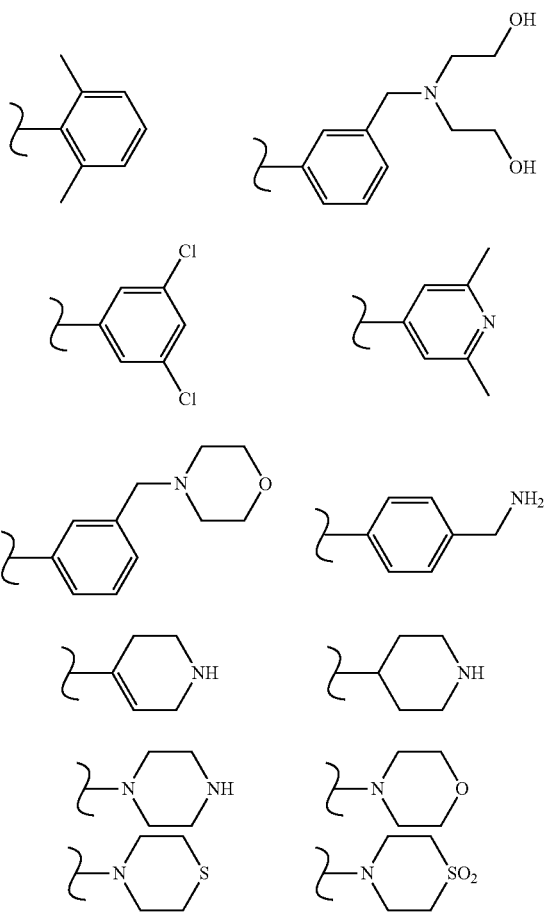

Examples of substituted phenyl carbocycles include:

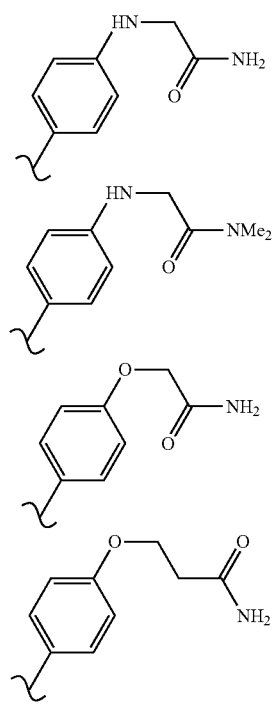

-continued

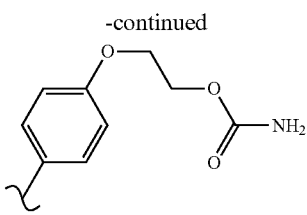

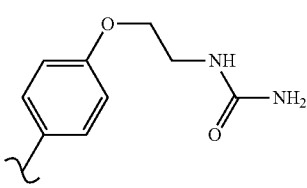

Embodiments of

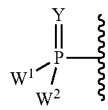

of Formula I-III compounds include substructures such as:

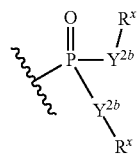

wherein each $Y^{2b}$ is, independently, O or N(R). In another aspect of this embodiment, each $Y^{2b}$ is O and each IV is independently:

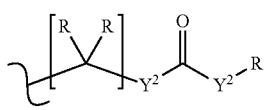
M12c wherein M12c is 1, 2 or 3 and each $Y^2$ is independently a bond, O, $CR_2$, or S. In another aspect of this embodiment, one $Y^{2b}$—$R^x$ is NH(R) and the other $Y^{2b}$—$R^x$ is O—$R^x$ wherein $R^x$ is:

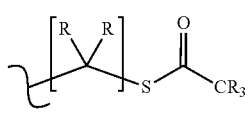
M12c wherein M12c is 2. In another aspect of this embodiment, each $Y^{2b}$ is O and each $R^x$ is independently:

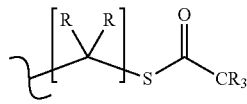
M12c wherein M12c is 2. In another aspect of this embodiment, each $Y^{2b}$ is O and each $R^x$ is independently:

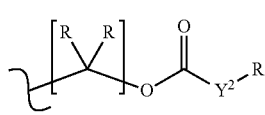
M12c wherein M12e is 1 and $Y^2$ is a bond, O, or $CR_2$.

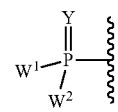

Other embodiments of Formulas I-III compounds include substructures such as:

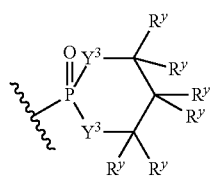

wherein each $Y^3$ is, independently, O or N(R). In another aspect of this embodiment, each $Y^3$ is O. In another aspect of this embodiment, the substructure is:

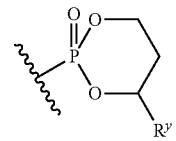

wherein $R^y$ is $W^5$ as defined herein.

Another embodiment of

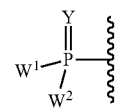

of Formula I-III includes the substructures:

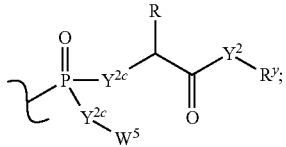

wherein each $Y^{2c}$ is, independently, O, N($R^y$) or S.

Another embodiment of

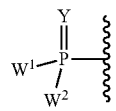

of Formula I-III compounds includes the substructures wherein one of $W^1$ or $W^2$ together with either $R^3$ or $R^4$ is —$Y^3$— and the other of $W^1$ or $W^2$ is Formula Ia. Such an embodiment is represented by a compound of Formula Ib selected from:

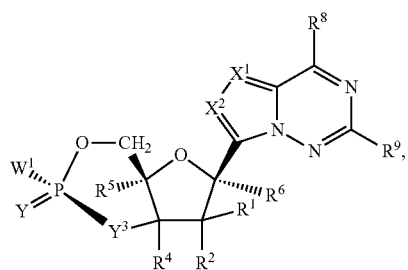

Formula Ib

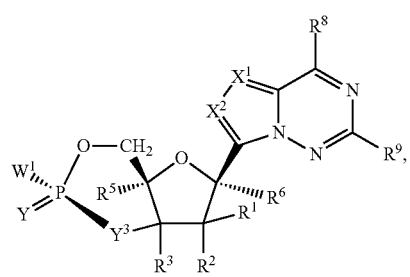

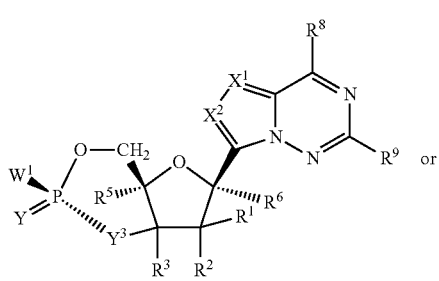

or

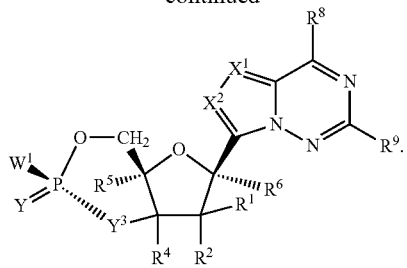

In another aspect of the embodiment of Formula Ib, each Y and $Y^3$ is O. In another aspect of the embodiment of Formula Ib, $W^1$ or $W^2$ is $Y^{2b}$—$R^x$; each Y, $Y^3$ and $Y^{2b}$ is O and $R^x$ is:

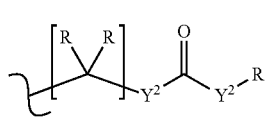

M12c wherein M12c is 1, 2 or 3 and each $Y^2$ is independently a bond, O, $CR_2$, or S. In another aspect of the embodiment of Formula Ib, $W^1$ or $W^2$ is $Y^{2b}$—$R^x$; each Y, $Y^3$ and $Y^{2b}$ is O and $R^x$ is:

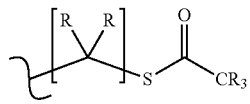

M12c wherein M12c is 2. In another aspect of the embodiment of Formula Ib, $W^1$ or $W^2$ is $Y^{2b}$—$R^x$; each Y, $Y^3$ and $Y^{2b}$ is O and $R^x$ is:

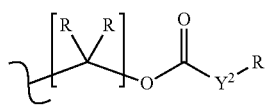

M12c wherein M12c is 1 and $Y^{20}$ is a bond, O, or $CR_2$.

Another embodiment of

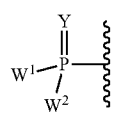

of Formula I-III compounds includes a substructure:

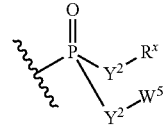

wherein $W^5$ is a carbocycle such as phenyl or substituted phenyl. In another aspect of this embodiment, the substructure is:

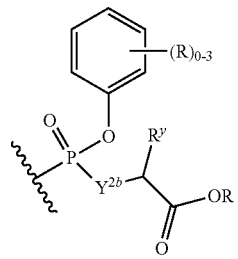

wherein $Y^{2b}$ is O or N(R) and the phenyl carbocycle is substituted with 0 to 3 R groups. In another aspect of this embodiment of the substructure, $R^x$ is:

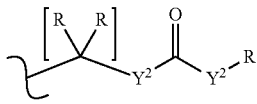

M12c wherein M12c is 1, 2 or 3 and each $Y^2$ is independently a bond, O, $CR_2$, or S.

Another embodiment of

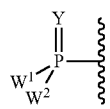

of Formula I-III includes substructure:

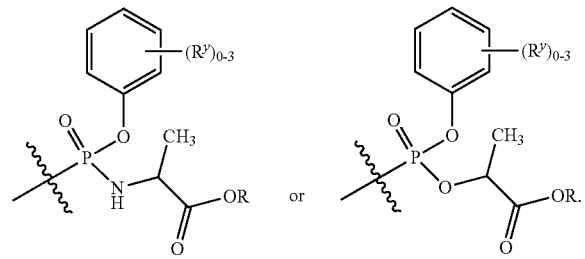

The chiral carbon of the amino acid and lactate moieties may be either the R or S configuration or the racemic mixture.

Another embodiment of

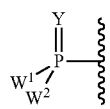

of Formula I-III is substructure

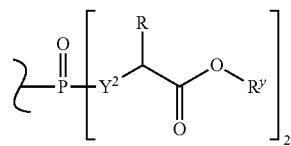

wherein each $Y^2$ is, independently, —O— or —NH—. In another aspect of this embodiment, $R^y$ is ($C_1$-$C_8$) alkyl, ($C_1$-$C_8$) substituted alkyl, ($C_2$-$C_8$) alkenyl, ($C_2$-$C_8$) substituted alkenyl, ($C_2$-$C_8$) alkynyl or ($C_2$-$C_8$) substituted alkynyl. In another aspect of this embodiment, $R^y$ is ($C_1$-$C_8$) alkyl, ($C_1$-$C_8$) substituted alkyl, ($C_2$-$C_8$) alkenyl, ($C_2$-$C_8$) substituted alkenyl, ($C_2$-$C_8$) alkynyl or ($C_2$-$C_8$) substituted alkynyl; and R is $CH_3$. In another aspect of this embodiment, $R^y$ is ($C_1$-$C_8$) alkyl, ($C_1$-$C_8$) substituted alkyl, ($C_2$-$C_8$) alkenyl, ($C_2$-$C_8$) substituted alkenyl, ($C_2$-$C_8$) alkynyl or ($C_2$-$C_8$) substituted alkynyl; R is $CH_3$; and each $Y^2$ is —NH—. In a aspect of this embodiment, $W^1$ and $W^2$ are, independently, nitrogen-linked, naturally occurring amino acids or naturally occurring amino acid esters. In another aspect of this embodiment, $W^1$ and $W^2$ are, independently, naturally-occurring 2-hydroxy carboxylic acids or naturally-occurring 2-hydroxy carboxylic acid esters wherein the acid or ester is linked to P through the 2-hydroxy group.

Another embodiment of

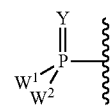

of Formula I, Formula II, or Formula III is substructure:

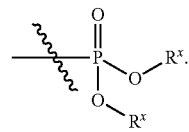

In one aspect of this embodiment, each $R^x$ is, independently, ($C_1$-$C_8$) alkyl. In another aspect of this embodiment, each $R^x$ is, independently, $C_6$-$C_{20}$ aryl or $C_6$-$C_{20}$ substituted aryl.

In a preferred embodiment,

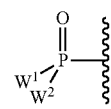

is selected from

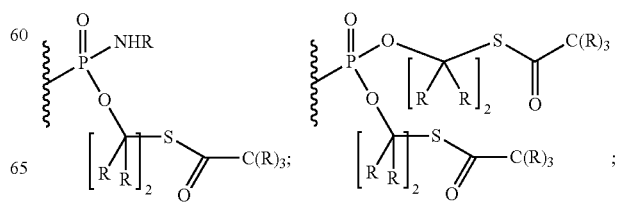

-continued

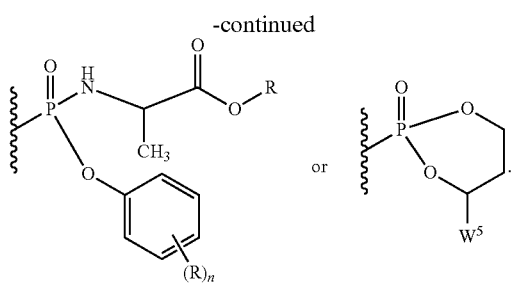

Another embodiment of

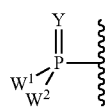

of Formulas I-III is substructure

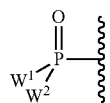

wherein $W^1$ and $W^2$ are independently selected from one of the formulas in Tables 20.1-20.37 and Table 30.1 below. The variables used in Tables 20.1-20.37 (e.g., $W^{23}$, $R^{21}$, etc.) pertain only to Tables 20.1-20.37, unless otherwise indicated.

The variables used in Tables 20.1 to 20.37 have the following definitions:

each $R^{21}$ is independently H or $(C_1-C_8)$alkyl;

each $R^{22}$ is independently H, $R^{21}$, $R^{23}$ or $R^{24}$ wherein each $R^{24}$ is independently substituted with 0 to 3 $R^{23}$;

each $R^{23}$ is independently $R^{23a}$, $R^{23b}$, $R^{23c}$ or $R^{23d}$, provided that when $R^{23}$ is bound to a heteroatom, then $R^{23}$ is $K^{23c}$ or $R^{23d}$;

each $R^{23a}$ is independently F, Cl, Br, I, —CN, $N_3$ or —$NO_2$;

each $R^{23b}$ is independently $Y^{21}$;

each $R^{23c}$ is independently —$R^{2x}$, —$N(R^{2x})(R^{2x})$, —$SR^{2x}$, —$S(O)R^{2x}$, —$S(O)_2R^{2x}$, —$S(O)(OR^{2x})$, —$S(O)_2(OR^{2x})$, —$OC(=Y^{21})R^{2x}$, —$OC(=Y^{21})OR^{2x}$, —$OC(=Y^{21})(N(R^{2x})(R^{2x}))$, —$SC(=Y^{21})R^{2x}$, —$SC(=Y^{21})OR^{2x}$, —$SC(=Y^{21})(N(R^{2x})(R^{2x}))$, —$N(R^{2x})C(=Y^{21})R^{2x}$, —$N(R^{2x})C(=Y^{21})OR^{2x}$, or —$N(R^{2x})C(=Y^{21})(N(R^{2x})(R^{2x}))$, each $R^{23d}$ is independently —$C(=Y^{21})R^{2x}$, —$C(=Y^{21})OR^{2x}$ or —$C(=Y^{21})(N(R^{2x})(R^{2x}))$;

each $R^{2X}$ is independently H, $(C_1-C_8)$alkyl, $(C_2-C_8)$alkenyl, $(C_2-C_8)$alkynyl, aryl, heteroaryl; or two $R^{2x}$ taken together with a nitrogen to which they are both attached form a 3 to 7 membered heterocyclic ring wherein any one carbon atom of said heterocyclic ring can optionally be replaced with —O—, —S— or $NR^{21}$—; and wherein one or more of the non-terminal carbon atoms of each said $(C_1-C_8)$alkyl may be optionally replaced with —O—, —S— or —$NR^{21}$—;

each $R^{24}$ is independently $(C_1-C_8)$alkyl, $(C_2-C_8)$alkenyl, or $(C_2-C_8)$alkynyl;

each $R^{25}$ is independently $R^{24}$ wherein each $R^{24}$ is substituted with 0 to 3 $R^{23}$ groups;

each $R^{25a}$ is independently $(C_1-C_8)$alkylene, $(C_2-C_8)$alkenylene, or $(C_2-C_8)$alkynylene any one of which said $(C_1-C_8)$alkylene, $(C_2-C_8)$alkenylene, or $(C_2-C_8)$alkynylene is substituted with 0-3 $R^{23}$ groups;

each $W^{23}$ is independently $W^{24}$ or $W^{25}$;

each $W^{24}$ is independently $R^{25}$, —$C(=Y^{21})R^{25}$, —$C(=Y^{21})W^{25}$, —$SO_2R^{25}$, or —$SO_2W^{25}$;

each $W^{25}$ is independently carbocycle or heterocycle wherein $W^{25}$ is independently substituted with 0 to 3 $R^{22}$ groups; and each $Y^{21}$ is independently O or S.

TABLE 20.1

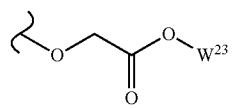

1

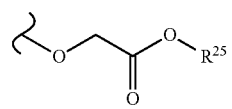

2

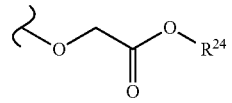

3

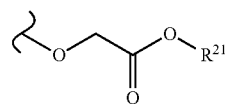

4

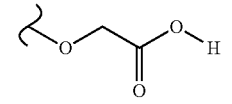

5

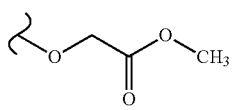

6

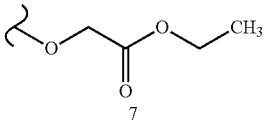

7

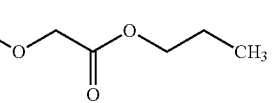

8

TABLE 20.2
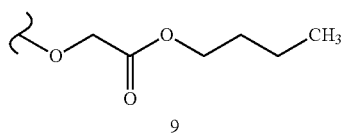
9
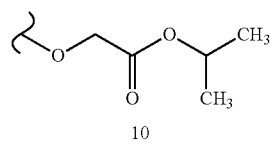
10
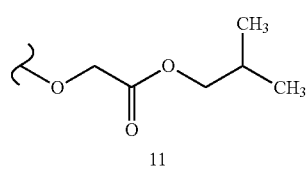
11
TABLE 20.3
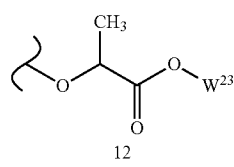
12
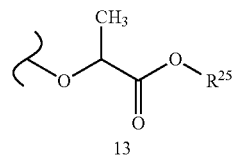
13
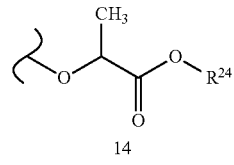
14
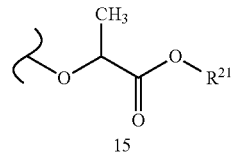
15
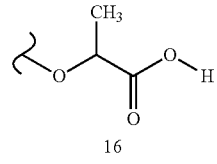
16
TABLE 20.3-continued
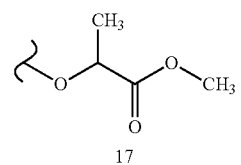
17
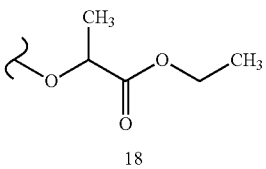
18
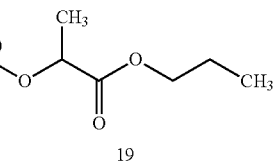
19
TABLE 20.4
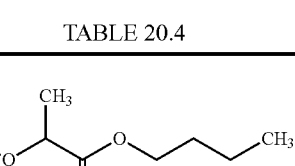
20
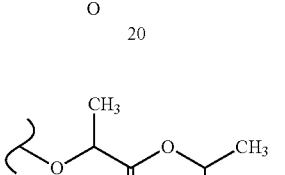
21
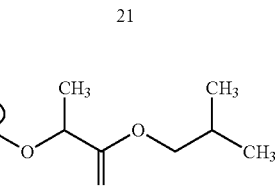
22
TABLE 20.5
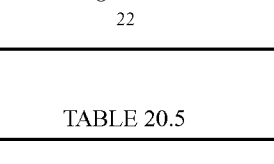
23

TABLE 20.5-continued

| No. | Structure |
|---|---|
| 24 | 2-(alkoxy)butanoate ester with $R^{25}$ |
| 25 | 2-(alkoxy)butanoate ester with $R^{24}$ |
| 26 | 2-(alkoxy)butanoate ester with $R^{21}$ |
| 27 | 2-(alkoxy)butanoic acid |
| 28 | methyl 2-(alkoxy)butanoate |
| 29 | ethyl 2-(alkoxy)butanoate |
| 30 | propyl 2-(alkoxy)butanoate |

TABLE 20.6

| No. | Structure |
|---|---|
| 31 | butyl 2-(alkoxy)butanoate |
| 32 | isopropyl 2-(alkoxy)butanoate |
| 33 | isobutyl 2-(alkoxy)butanoate |

TABLE 20.7

| No. | Structure |
|---|---|
| 34 | $W^{23}$-substituted 2-(alkoxy)acetate ester with $W^{23}$ |
| 35 | $W^{23}$-substituted 2-(alkoxy)acetate ester with $R^{25}$ |
| 36 | $W^{23}$-substituted 2-(alkoxy)acetate ester with $R^{24}$ |
| 37 | $W^{23}$-substituted 2-(alkoxy)acetate ester with $R^{21}$ |

TABLE 20.7-continued
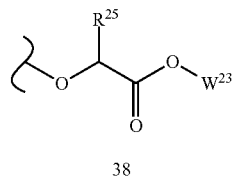
38
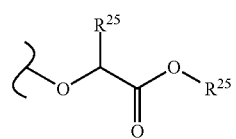
39
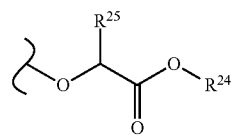
40
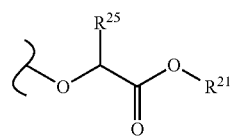
41
TABLE 20.8
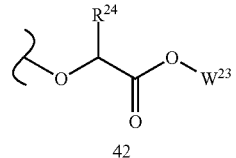
42
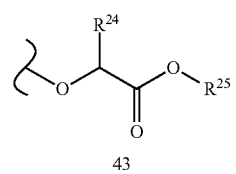
43
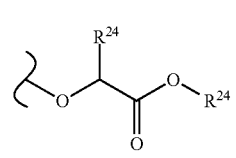
44
TABLE 20.8-continued
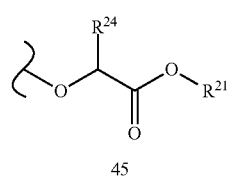
45
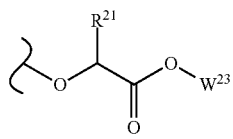
46
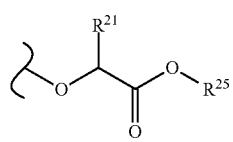
47
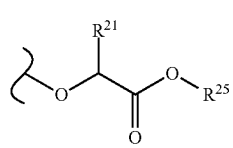
48
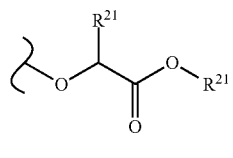
49
TABLE 20.9
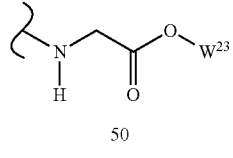
50
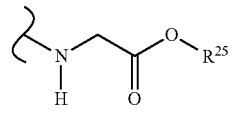
51

TABLE 20.9-continued
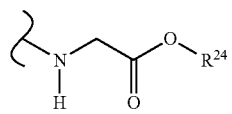
52
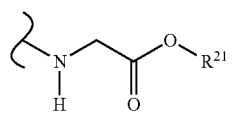
53
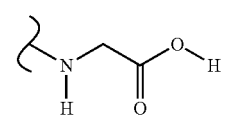
54
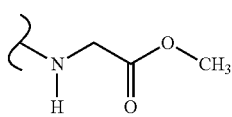
55
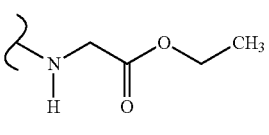
56
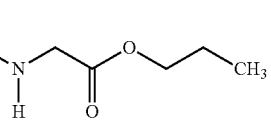
57
TABLE 20.10
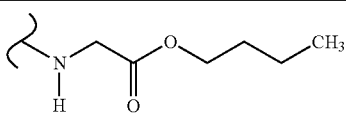
58
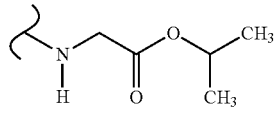
59
TABLE 20.10-continued
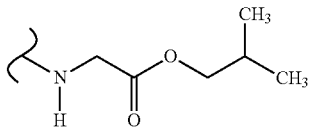
60
TABLE 20.11
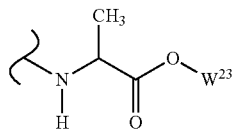
61
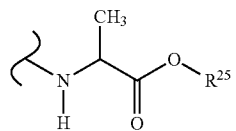
62
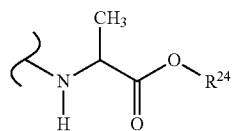
63
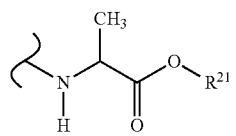
64
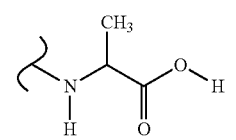
65
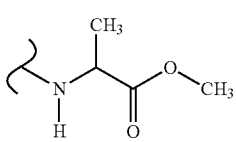
66
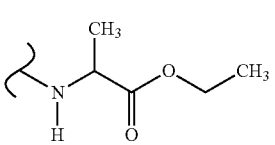
67

TABLE 20.11-continued
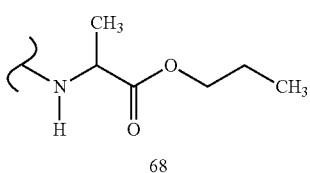
68
TABLE 20.12
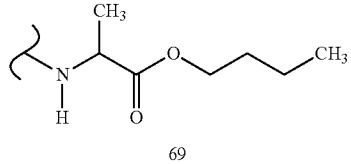
69
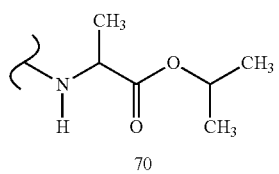
70
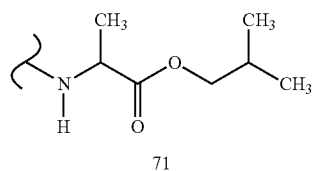
71
TABLE 20.13
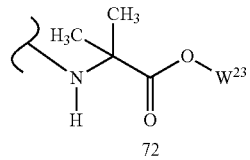
72
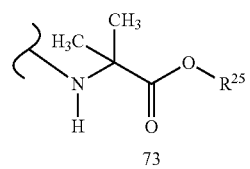
73
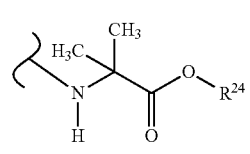
74
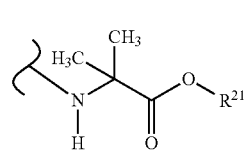
75
TABLE 20.13-continued
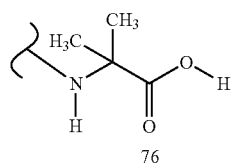
76
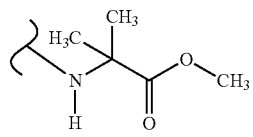
77
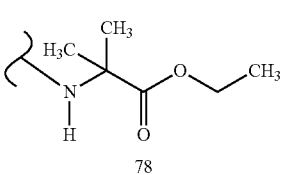
78
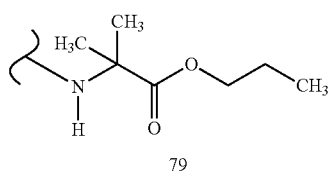
79
TABLE 20.14
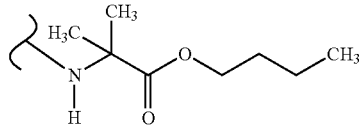
80
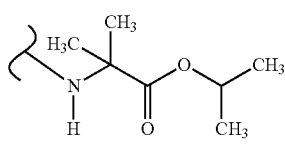
81
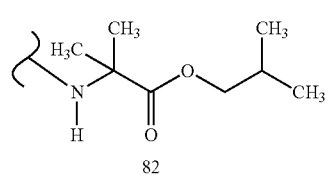
82
TABLE 20.15
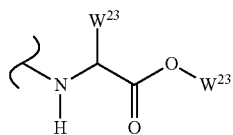
83

TABLE 20.15-continued
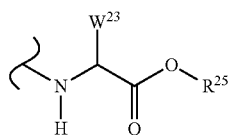
84
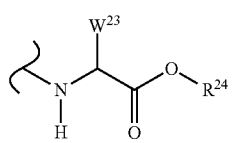
85
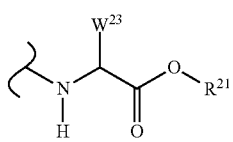
86
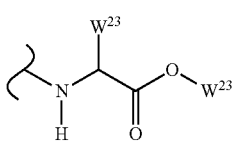
87
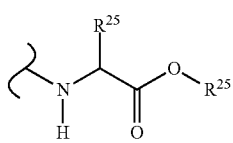
88
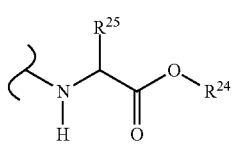
89
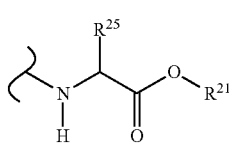
90
TABLE 20.16
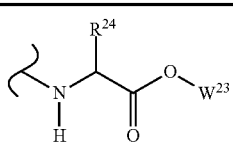
91
TABLE 20.16-continued
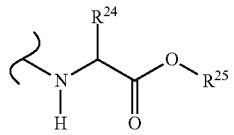
92
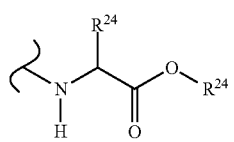
93
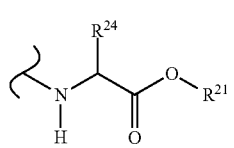
94
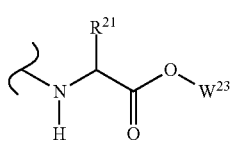
95
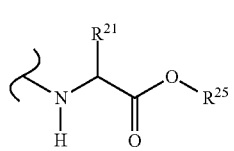
96
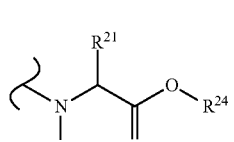
97
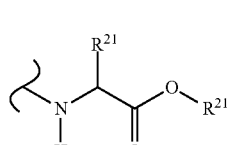
98
TABLE 20.17
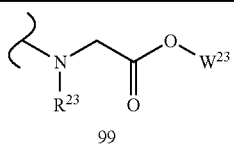
99

TABLE 20.17-continued
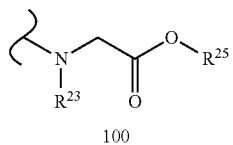
100
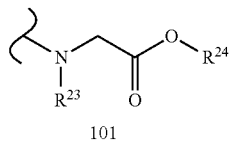
101
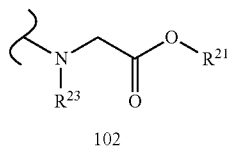
102
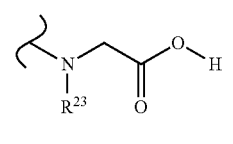
103
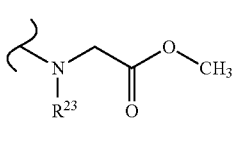
104
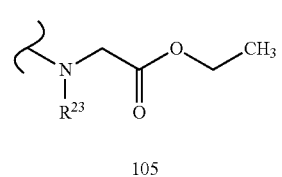
105
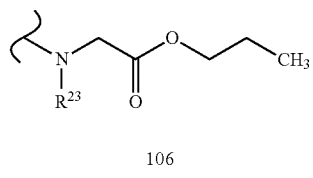
106
TABLE 20.18
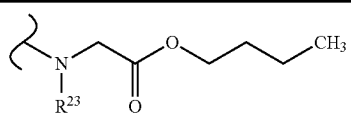
107
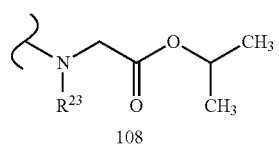
108
TABLE 20.18-continued
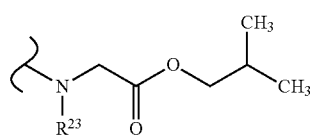
109
TABLE 20.19
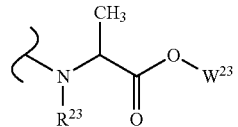
110
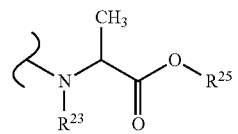
111
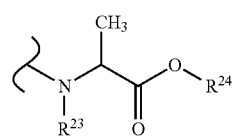
112
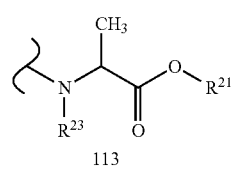
113
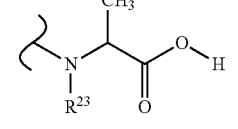
114
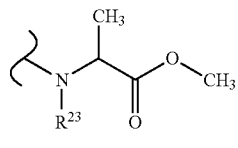
115
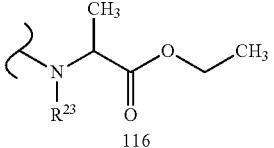
116

TABLE 20.19-continued
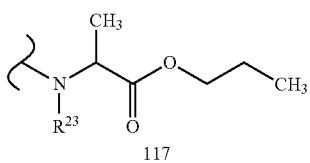
117
TABLE 20.20
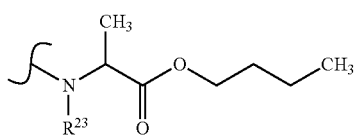
118
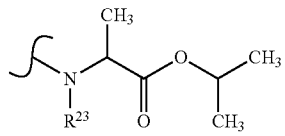
119
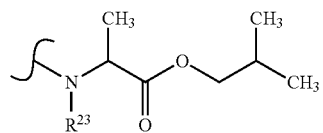
120
TABLE 20.21
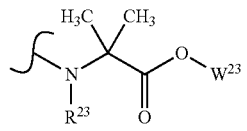
121
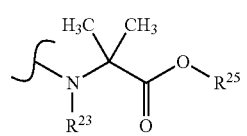
122
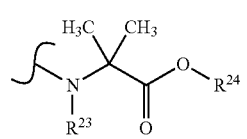
123
TABLE 20.21-continued
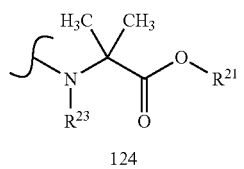
124
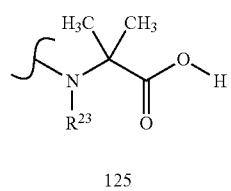
125
126
127
128
TABLE 20.22
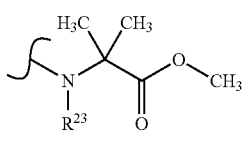
129
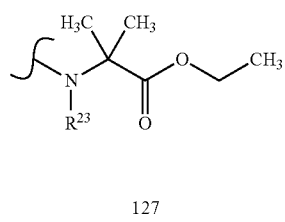
130

TABLE 20.22-continued
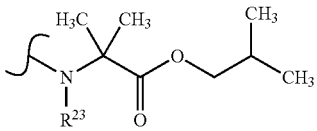
131
TABLE 20.23
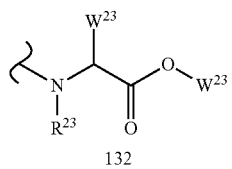
132
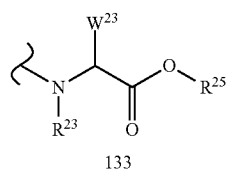
133
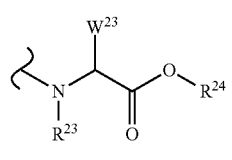
134
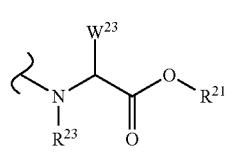
135
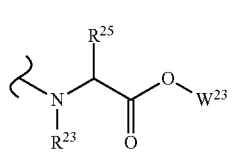
136
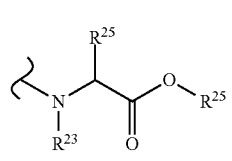
137
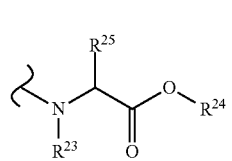
138
TABLE 20.23-continued
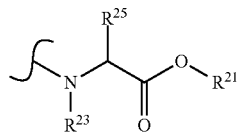
139
TABLE 20.24
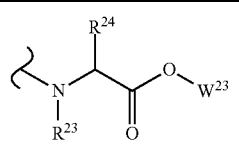
140
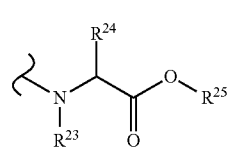
141
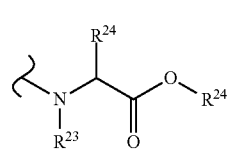
142
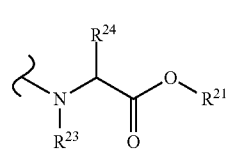
143
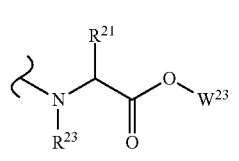
144
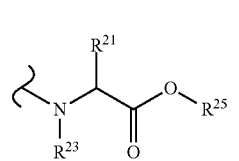
145
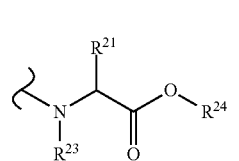
146

TABLE 20.24-continued
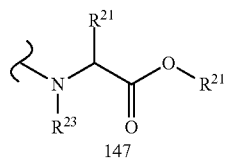
147
TABLE 20.25
148
149
150
151
152
153
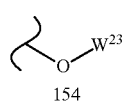
154
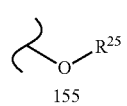
155
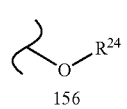
156
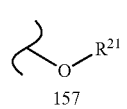
157
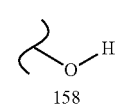
158
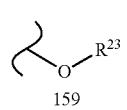
159
TABLE 20.26
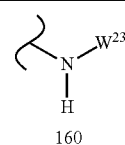
160
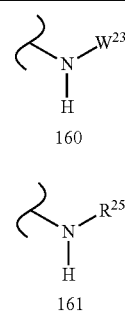
161
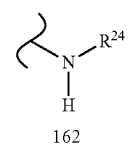
162
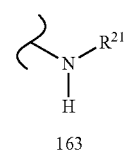
163
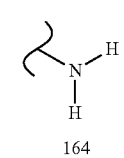
164
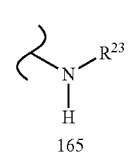
165
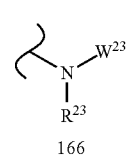
166
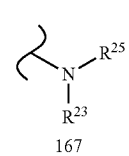
167
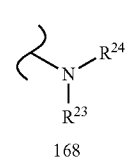
168
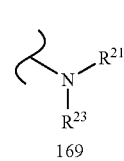
169

TABLE 20.26-continued
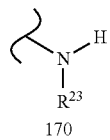
170
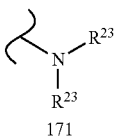
171
TABLE 20.27
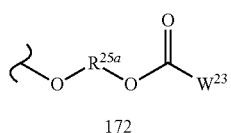
172
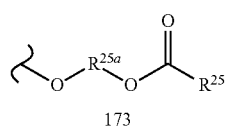
173
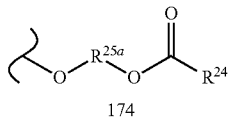
174
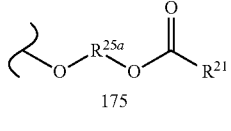
175
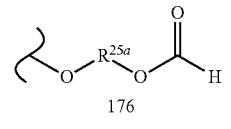
176
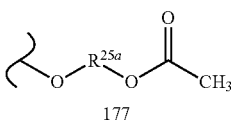
177
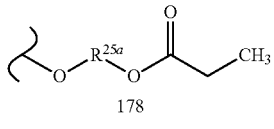
178
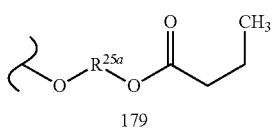
179
TABLE 20.28
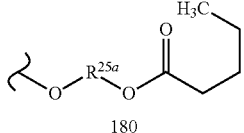
180
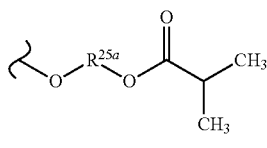
181
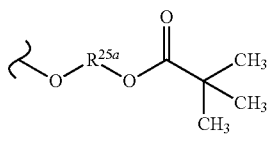
182
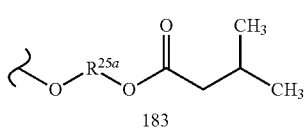
183
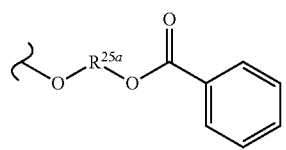
184
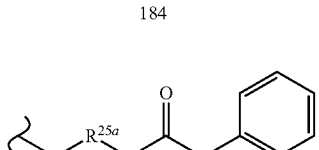
185
TABLE 20.29
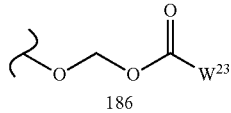
186
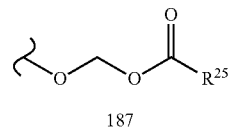
187
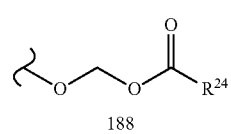
188

TABLE 20.29-continued
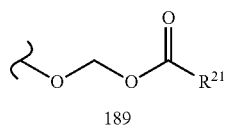
189
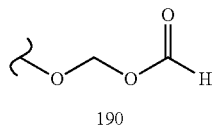
190
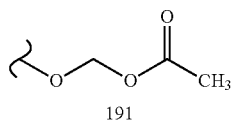
191
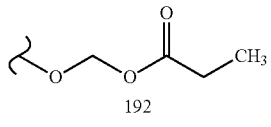
192
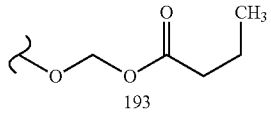
193
TABLE 20.30
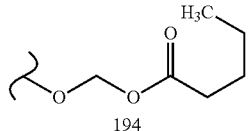
194
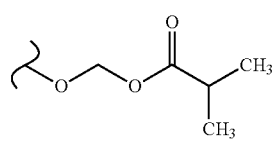
195
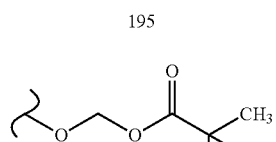
196
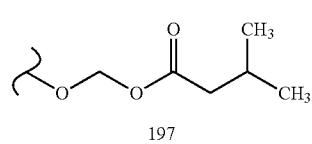
197
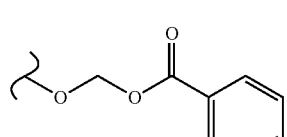
198
TABLE 20.30-continued
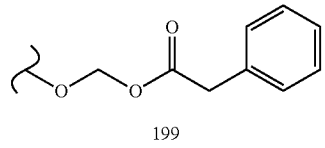
199
TABLE 20.31
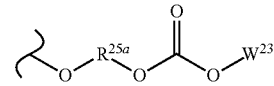
200
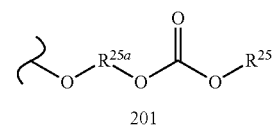
201
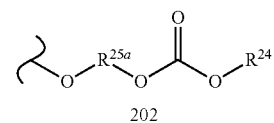
202
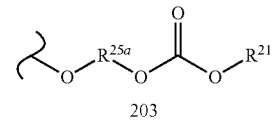
203
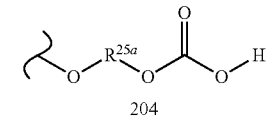
204
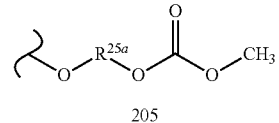
205
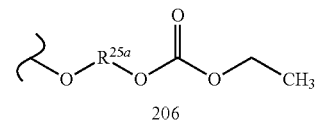
206
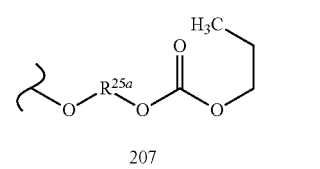
207

TABLE 20.32
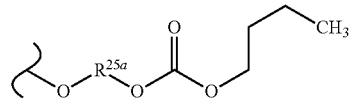
208
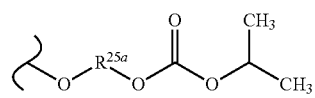
209
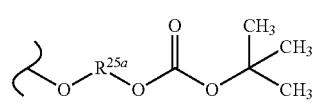
210
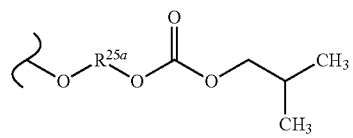
211
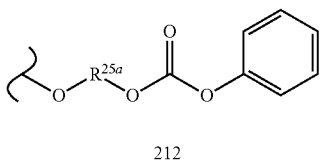
212
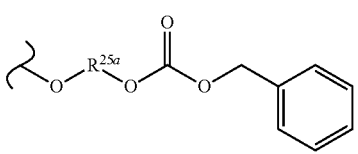
213
TABLE 20.33
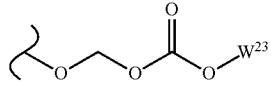
214
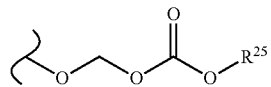
215
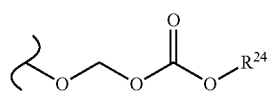
216
TABLE 20.33-continued
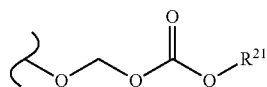
217
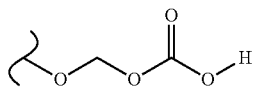
218
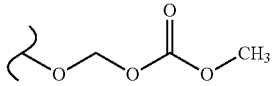
219
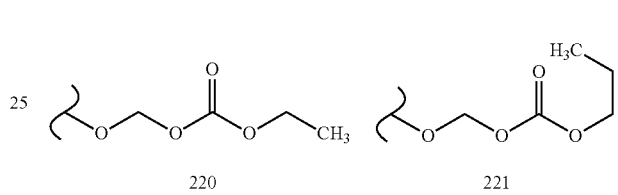
220     221
TABLE 20.34
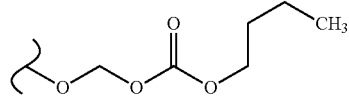
222
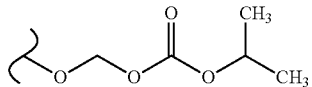
223
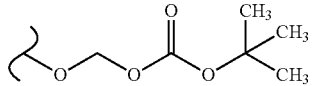
224
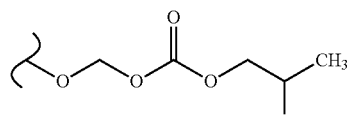
225
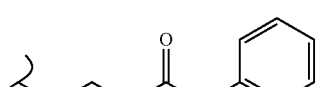
226

TABLE 20.34-continued
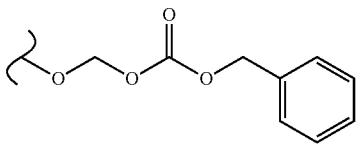
227
TABLE 20.35
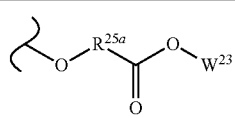
228
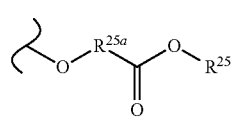
229
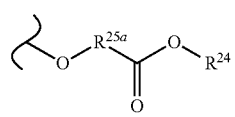
230
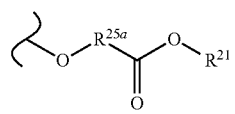
231
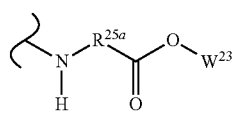
232
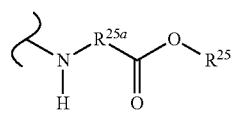
233
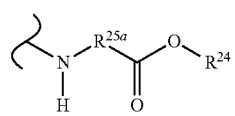
234
TABLE 20.35-continued
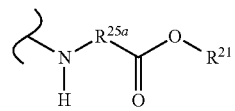
235
TABLE 20.36
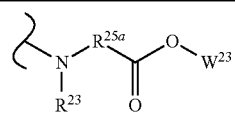
236
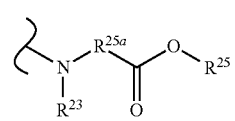
237
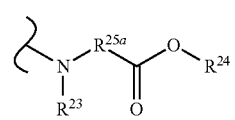
238
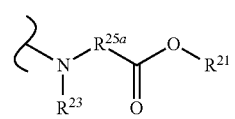
239
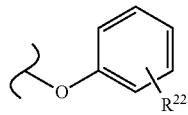
240
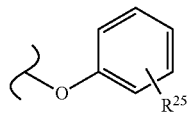
241
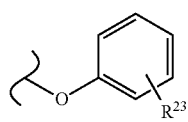
242
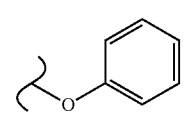
243

TABLE 20.37
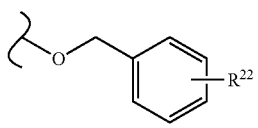
244
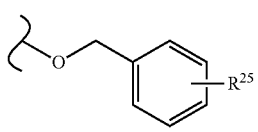
245
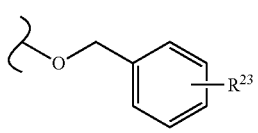
246
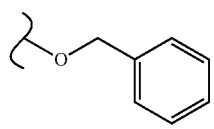
247
TABLE 30.1
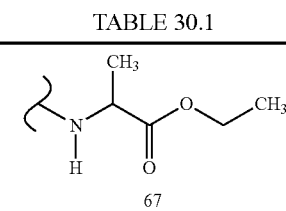
67
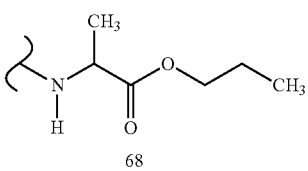
68
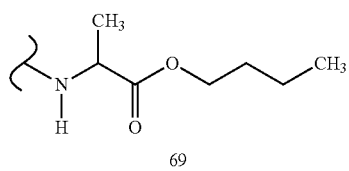
69
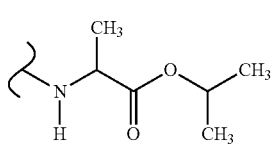
70
TABLE 30.1-continued
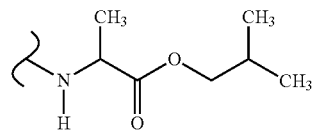
71
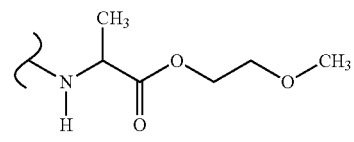
258
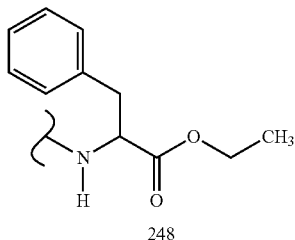
248
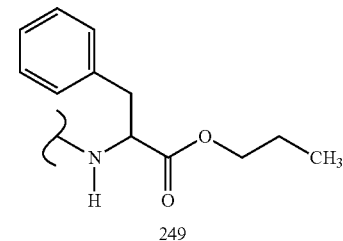
249
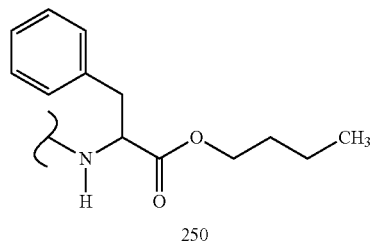
250
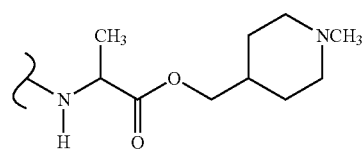
251
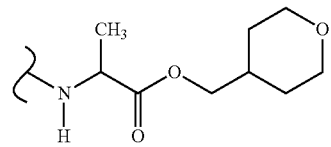
252

TABLE 30.1-continued

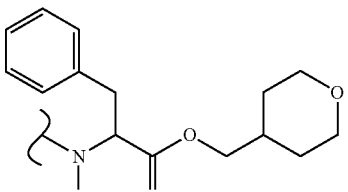

253

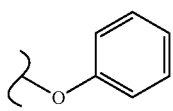

254

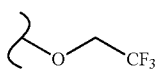

255

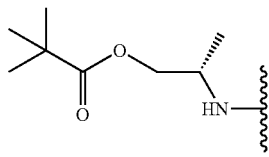

256

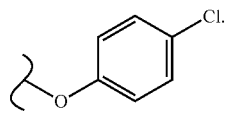

257

Embodiments of $R^x$ include esters, carbamates, carbonates, thioesters, amides, thioamides, and urea groups:

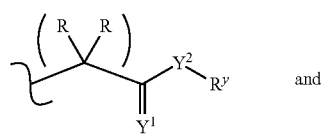 M12a and

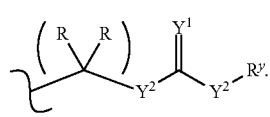 M12a

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR_4^+$.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

The compounds of the invention, exemplified by Formula I-III may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "R" or "$R^1$", then it will be understood that the groups may be the same or different, i.e., each group is independently selected. Wavy lines, ∿∿∿, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

One skilled in the art will recognize that the pyrrolo[1,2-f][1,2,4]triazine, imidazo[1,5-f][1,2,4]triazine, imidazo[1,2,4][1,2,4]triazine, and [1,2,4]triazolo[4,3-f][1,2,4]triazine nucleosides can exist in tautomeric forms. For example, but not by way of limitation, structures (a) and (b) can have equivalent tautomeric forms as shown below:

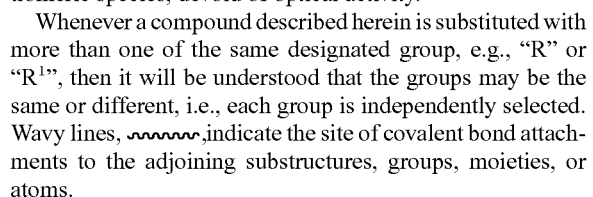

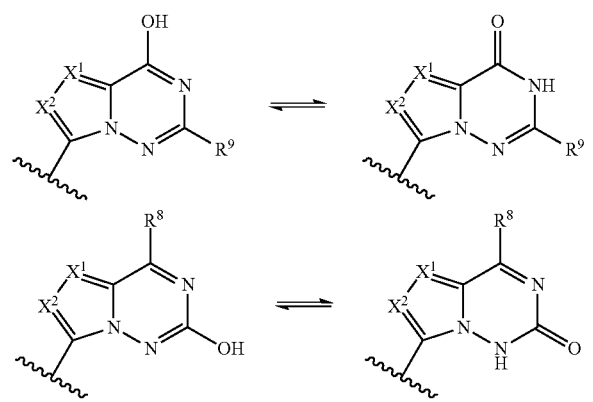

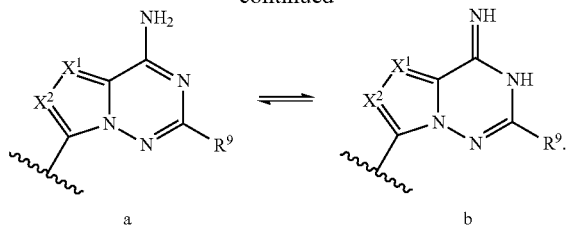

a                                                b

All possible tautomeric forms of the heterocycles in all of the embodiments disclosed herein are within the scope of the invention.

Methods of Inhibition of HCV Polymerase

Another aspect of the invention relates to methods of inhibiting the activity of HCV polymerase comprising the step of treating a sample suspected of containing HCV with a composition of the invention.

Compositions of the invention may act as inhibitors of HCV polymerase, as intermediates for such inhibitors or have other utilities as described below. The inhibitors will bind to locations on the surface or in a cavity of HCV polymerase having a geometry unique to HCV polymerase Compositions binding HCV polymerase may bind with varying degrees of reversibility. Those compounds binding substantially irreversibly are ideal candidates for use in this method of the invention. Once labeled, the substantially irreversibly binding compositions are useful as probes for the detection of HCV polymerase. Accordingly, the invention relates to methods of detecting HCV polymerase in a sample suspected of containing HCV polymerase comprising the steps of: treating a sample suspected of containing HCV polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HCV polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HCV polymerase, frequently a pathogenic organism such as HCV. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HCV polymerase after application of the composition can be observed by any method including direct and indirect methods of detecting HCV polymerase activity. Quantitative, qualitative, and semiquantitative methods of determining HCV polymerase activity are all contemplated. Typically one of the screening methods described above are applied, however, any other method such as observation of the physiological properties of a living organism are also applicable.

Organisms that contain HCV polymerase include the HCV virus. The compounds of this invention are useful in the treatment or prophylaxis of HCV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HCV polymerase Inhibitors.

Compositions of the invention are screened for inhibitory activity against HCV polymerase by any of the conventional techniques for evaluating enzyme activity. Within the context of the invention, typically compositions are first screened for inhibition of HCV polymerase in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 1.5% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-dial, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Combinations of the compounds of Formula I-III are typically selected based on the condition to be treated, cross-reactivities of ingredients and pharmaco-properties of the combination. For example, when treating an infection (e.g., HCV), the compositions of the invention are combined with other active therapeutic agents (such as those described herein).

Compositions of the invention are also used in combination with one or more other active ingredients. Preferably, the other active therapeutic ingredients or agents are interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers or other drugs for treating HCV; or mixtures thereof.

More specifically, one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Aileron), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-419-4477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib)

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or excipient.

According to the present invention, the therapeutic agent used in combination with the compound or composition of the present invention can be any agent having a therapeutic effect when used in combination with the compound of the present invention. For example, the therapeutic agent used in combination with the compound or composition of the present invention can be interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers or other drugs for treating HCV; or mixtures thereof.

More specifically, compositions of one or more compounds of the present invention may be combined with one or more compounds selected from the group consisting of 1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon). IFN alpha XL, BLX-883 (Locteron), DA-3021, glycosylated interferon alpha-2b (AVI-005), PEG-Infergen, PEGylated interferon lambda (PEGylated IL-29), and belerofon, 2) ribavirin and its analogs, e.g., ribavirin (Rebetol, Copegus), and taribavirin (Viramidine), 3) HCV NS3 protease inhibitors, e.g., boceprevir (SCH-503034, SCH-7), telaprevir (VX-950), VX-813, TMC-435 (TMC435350), ABT-450, BI-201335, BI-1230, MK-7009, SCH-900518, VBY-376, VX-500, GS-9256, GS-9451, BMS-790052, BMS-605339, PHX-1766, AS-101, YH-5258, YH5530, YH5531, and ITMN-191 (R-7227), 4) alpha-glucosidase 1 inhibitors, e.g., celgosivir (MX-3253), Miglitol, and UT-231B, 5) hepatoprotectants, e.g., emericasan (IDN-6556), ME-3738, GS-9450 (LB-84451), silibilin, and MitoQ, 6) nucleoside or nucleotide inhibitors of HCV NS5B polymerase, e.g., R1626, R7128 (R4048), IDX184, IDX-102, PSI-7851, BCX-4678, valopicitabine (NM-283), and MK-0608, 7) non-nucleoside inhibitors of HCV NS5B polymerase, e.g., filibuvir (PF-868554), ABT-333, ABT-072, BI-207127, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILK-1941, XTL-2125, and GS-9190, 8) HCV NS5A inhibitors, e.g., AZD-2836 (A-831), AZD-7295 (A-689), and BMS-790052, 9) TLR-7 agonists, e.g., imiquimod, 852A, GS-9524, ANA-773, ANA-975, AZD-8848 (DSP-3025), PF-04878691, and SM-360320, 10) cyclophillin inhibitors, e.g., DEBIO-025, SCY-635, and NIM811, 11) HCV IRES inhibitors, e.g., MCI-067, 12) pharmacokinetic enhancers, e.g., BAS-100, SPI-452, PF-419-4477, TMC-41629, GS-9350, GS-9585, and roxythromycin, 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, FK-788, and VX-497 (merimepodib)

14) mevalonate decarboxylase antagonists, e.g., statins, HMGCoA synthase inhibitors (e.g., hymeglusin), squalene synthesis inhibitors (e.g., zaragozic acid);

15) angiotensin II receptor antagonists, e.g., losartan, irbesartan, olmesartan, candesartan, valsartan, telmisartan, eprosartan;

16) angiotensin-converting enzyme inhibitors, e.g., captopril, zofenopril, enalapril, ramipril, quinapril, perindopril, lisinopril, benazepril, fosinopril;

17) other anti-fibrotic agents, e.g., amiloride and 18) endothelin antagonists, e.g. bosentan and ambrisentan.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV, and combinations thereof.

Combinations of the compounds of Formula I-III and additional active therapeutic agents may be selected to treat patients infected with HCV and other conditions such as HIV infections. Accordingly, the compounds of Formula may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5a inhibitors, alpha-glucosidase 1 inhibitors, cyclophilin inhibitors, hepatoprotectants, non-nucleoside inhibitors of HCV, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir ritonavir, nelfinavir, saquinavir, tipranavir, brecanavir, darunavir, TMC-126, TMC-114, mozenavir (DMP-450), JE-2147 (AG1776), AG1859, DG35, L-756423, R00334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), IDX184, PSI-7851, HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HCV, e.g., benzimidazole derivatives, benzo-1,2,4-thiadiazine derivatives, and phenylalanine derivatives, 19) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811, 19) pharmacokinetic enhancers, e.g., BAS-100 and SPI452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting HCV polymerase in a cell, comprising: contacting a cell infected with HCV with an effective amount of a compound of Formula I-III, or a pharmaceutically acceptable salt, solvate, and/or ester thereof, whereby HCV polymerase is inhibited.

In still yet another embodiment, the present application provides for methods of inhibiting HCV polymerase in a cell, comprising: contacting a cell infected with HCV with an effective amount of a compound of Formula I-III, or a pharmaceutically acceptable salt, solvate, and/or ester thereof, and at least one additional active therapeutic agent, whereby HCV polymerase is inhibited.

In still yet another embodiment, the present application provides for methods of inhibiting HCV polymerase in a cell, comprising: contacting a cell infected with HCV with an effective amount of a compound of Formula I-ITT, or a pharmaceutically acceptable salt, solvate, and/or ester thereof, and at least one additional active therapeutic agent selected from the group consisting of one or more interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

In still yet another embodiment, the present application provides for methods of treating HCV in a patient, comprising: administering to the patient a therapeutically effective amount of a compound of Formula I-III, or a pharmaceutically acceptable salt, solvate, and/or ester thereof.

In still yet another embodiment, the present application provides for methods of treating HCV in a patient, comprising: administering to the patient a therapeutically effective amount of a compound of Formula I-III, or a pharmaceutically acceptable salt, solvate, and/or ester thereof, and at least one additional active therapeutic agent, whereby HCV polymerase is inhibited.

In still yet another embodiment, the present application provides for methods of treating HCV in a patient, comprising: administering to the patient a therapeutically effective amount of a compound of Formula I-III, or a pharmaceutically acceptable salt, solvate, and/or ester thereof, and at least one additional active therapeutic agent selected from the group consisting of one or more interferons, ribavirin or its analogs HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, endothelin antagonists, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

In still yet another embodiment, the present application provides for the use of a compound of the present invention, or a pharmaceutically acceptable salt, solvate, and/or ester thereof, for the preparation of a medicament for treating an HCV infection in a patient.

Metabolites of the Compounds of the Invention

Also falling within the scope of this invention are the in viva metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in viva, are useful in diagnostic assays for therapeutic dosing of the compounds of the invention even if they possess no HCV polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| $Ac_2O$ | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4, 4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| $MH^+$ | mass plus 1 |
| $MH^-$ | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutylammonium fluoride |
| TMSCl | chlorotrimethylsilane |
| TM SBr | bromotrimethylsilane |
| TMSI | iodotrimethylsilane |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | tri ethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

Preparation of Compounds

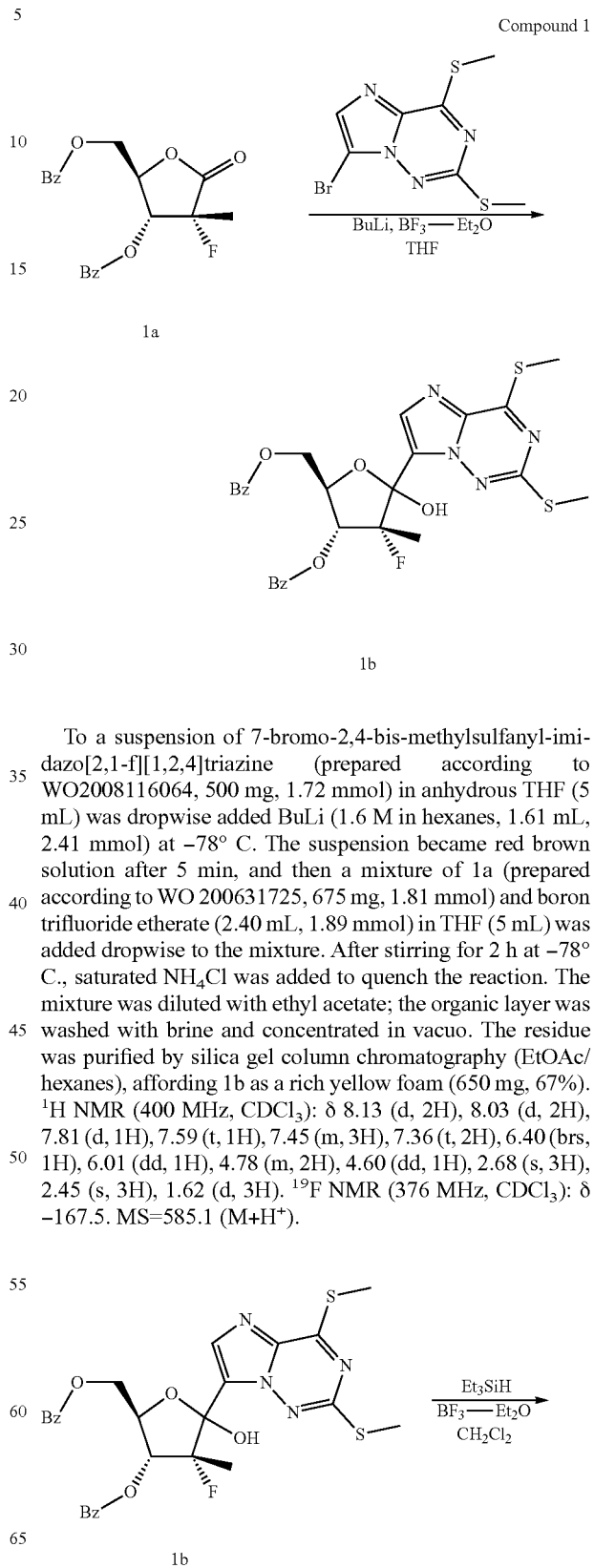

To a suspension of 7-bromo-2,4-bis-methylsulfanyl-imidazo[2,1-f][1,2,4]triazine (prepared according to WO2008116064, 500 mg, 1.72 mmol) in anhydrous THF (5 mL) was dropwise added BuLi (1.6 M in hexanes, 1.61 mL, 2.41 mmol) at −78° C. The suspension became red brown solution after 5 min, and then a mixture of 1a (prepared according to WO 200631725, 675 mg, 1.81 mmol) and boron trifluoride etherate (2.40 mL, 1.89 mmol) in THF (5 mL) was added dropwise to the mixture. After stirring for 2 h at −78° C., saturated $NH_4Cl$ was added to quench the reaction. The mixture was diluted with ethyl acetate; the organic layer was washed with brine and concentrated in vacuo. The residue was purified by silica gel column chromatography (EtOAc/hexanes), affording 1b as a rich yellow foam (650 mg, 67%). $^1H$ NMR (400 MHz, $CDCl_3$): δ 8.13 (d, 2H), 8.03 (d, 2H), 7.81 (d, 1H), 7.59 (t, 1H), 7.45 (m, 3H), 7.36 (t, 2H), 6.40 (brs, 1H), 6.01 (dd, 1H), 4.78 (m, 2H), 4.60 (dd, 1H), 2.68 (s, 3H), 2.45 (s, 3H), 1.62 (d, 3H). $^{19}F$ NMR (376 MHz, $CDCl_3$): δ −167.5. MS=585.1 ($M+H^+$).

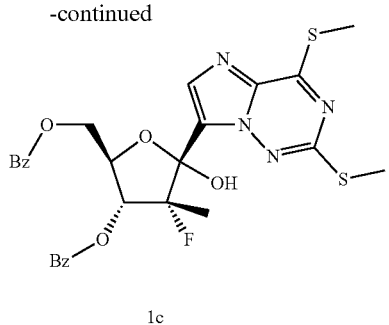

1c

To a solution of 1b (820 mg, 1.40 mmol) in dichloromethane (20 mL) were added boron trifluoride etherate (2 mL) and triethylsilane (2 mL), and stirred at room temperature for 16 h. Additional boron trifluoride etherate (1 mL) and triethylsilane (1 mL) were added, and stirred for 7 d. The mixture was diluted with dichloromethane and saturated sodium bicarbonate. The organic layer was washed sequentially with water, saturated ammonium chloride and brine, dried over magnesium sulfate, and concentrated. The residue was purified by silica gel column chromatography (EtOAc/hexanes), affording 1c (605 mg, 76%). $^1$H NMR (400 MHz, CDCl$_3$): δ 8.10 (d, J=7.2 Hz, 2H), 8.00 (d, J=7.2 Hz, 2H), 7.66 (s, 1H), 7.61 (t, J=7.2 Hz, 1H), 7.53 (t, J=7.2 Hz, 1H), 7.46 (t, J=7.2 Hz, 2H), 7.38 (t, J=7.2 Hz, 2H), 5.78 (m, 2H), 4.80 (dd, 1H), 4.68 (m, 1H), 4.60 (dd, 1H), 2.68 (s, 3H), 2.65 (s, 3H), 1.32 (d, 3H). $^{19}$F NMR (376 MHz, CDCl$_3$): δ −149.9. MS=569.1 (M+H$^+$).

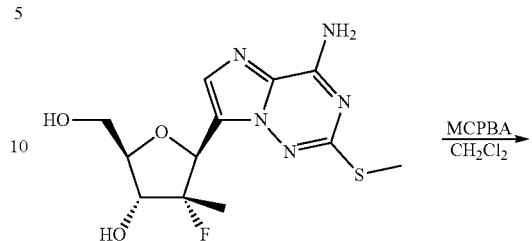

1H), 3.76 (m, 2H), 3.57 (m, 1H), 2.44 (s, 3H), 1.09 (d, 3H). $^{19}$F NMR (376 MHz, DMSO-d$_6$): δ −153.5. MS=330.1 (M H$^+$).

1d

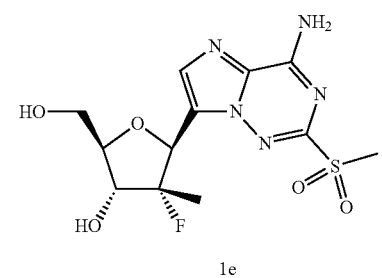

1e

To a solution of 1d (175 mg, 0.53 mmol) in dichloromethane (11 mL) was added MCPBA. (370 mg, ~1.5 mmol) and stirred at room temperature for 16 h. The mixture was concentrated, affording crude 1e which was used for the next reaction without purification. MS=362.0 (M+H$^+$).

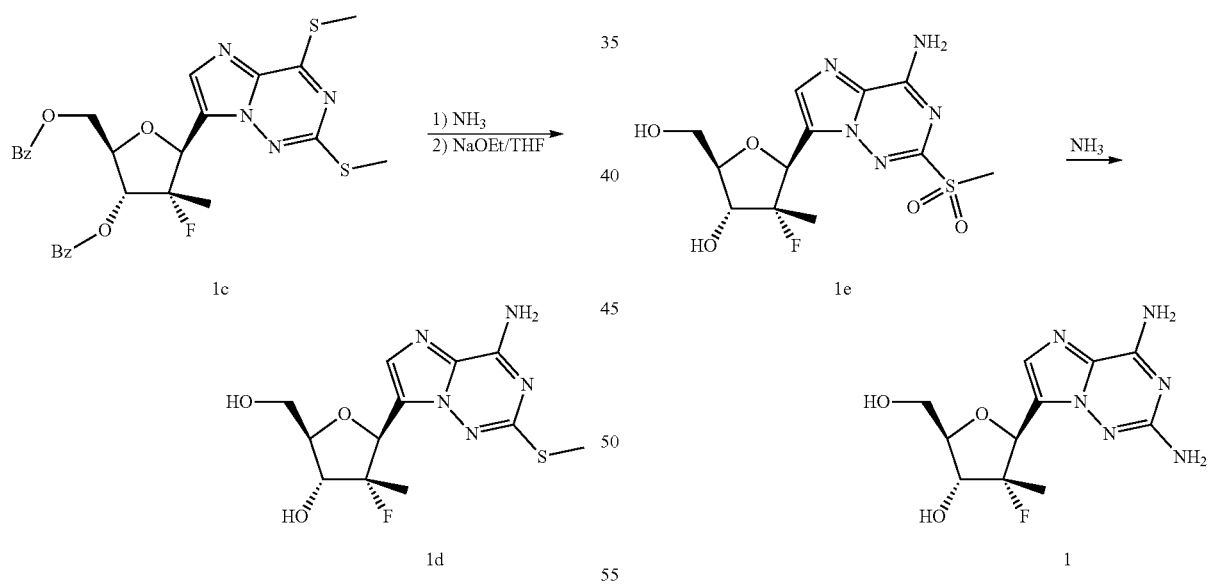

Compound 1c (635 mg, 1.12 mmol) was placed in a steel bomb reactor. Liquid ammonia (~30 mL) was charged and the bomb reactor was tightly sealed. The mixture was stirred at 50° C. for 16 h. After cooling to room temperature, ammonia was evaporated and the solid residue was dissolved in THF (10 mL) and MeOH (10 mL). Sodium ethoxide (25% wt. 0.63 mL) was added and stirred at 60° C. for 40 min. The mixture was neutralized with AcOH and concentrated. The resisue was purified by R HPLC, affording the product 1d (175 mg, 48%). $^1$H NMR (400 MHz, DMSO-d$_6$): δ 8.21 (brs, 2H), 7.60 (s, 1H), 5.45 (brs, 1H), 5.43 (d, 1H), 4.91 (t, 1H), 3.92 (m, Compound 1e (obtained from the previous reaction) was placed in a steel bomb reactor. Liquid ammonia (~30 mL) was charged, and the bomb reactor was tightly sealed. The mixture was stirred at 115 for 3 d. After cooling to room temperature, ammonia was evaporated. The solid residue was purified by RP HPLC, affording compound 1 (105 mg, 66% in two steps). $^1$H NMR (400 MHz, D$_2$O): δ 7.31 (s, 1H), 5.43 (d, J=25.2 Hz, 1H), 4.07 (dd, J=9.6, 23.2, 1H), 3.89 (m, 1H), 3.83 (dd, J=2.4, 12.8 Hz, 1H), 3.67 (dd, J=4.8, 12.8 Hz, 1H), 1.05 (d, J=22.8 Hz, 3H). $^{19}$F NMR (376 MHz, D$_2$O): δ −153.5. MS=299.2 (M H$^f$).

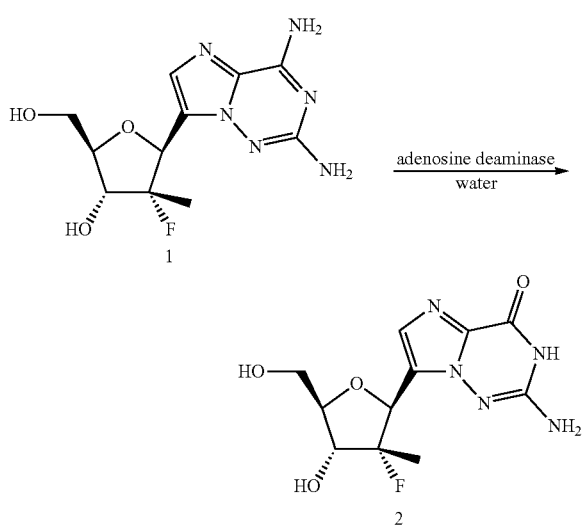

Compound 2

To a solution of compound 1 (82 mg, 0.28 mmol) in water (340 mL) was added adenosine deaminase (A5168 bovine spleen type IX from Sigma-Aldrich, 0.125 Unit per mL of water) and stirred at 37° C. for 4 h. The mixture was concentrated and purified by RP HPLC, affording compound 2 (56 mg, 68%). $^1$H NMR (400 MHz, D$_2$O): δ 7.35 (s, 1H), 5.46 (d, J=25.2 Hz, 1H), 4.08 (dd, J=9.6, 22.6, 1H), 3.93 (m, 1H), 3.87 (dd, J=2.4, 12.8 Hz, 1H), 3.71 (dd, J=4.8, 12.8 Hz, 1H), 1.12 (d, J=23.2 Hz, 3H). $^{19}$F NMR (376 MHz, D$_2$O): δ −153.4. MS=300.2 (M+H$^+$).

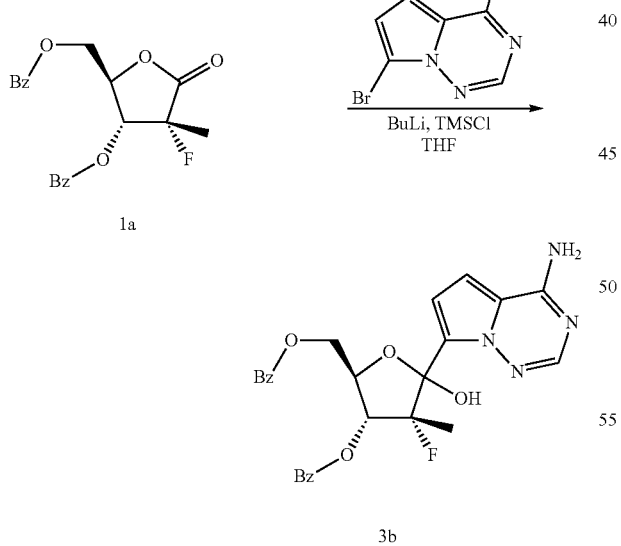

Compound 3

To a suspension of 7-bromo-pyrrolo[2,1-f][1,2,4]triazin-4-ylamine (prepared according to WO2007056170, 2.13 g, 10 mmol) in THF (20 mL) was added TMSCl (2.66 mL, 21 mmol) and stirred at room temperature for 16 h under argon. After cooling to −78° C., a solution of BuLi (1.6 M, 21 mL, 33 mmol) in hexanes was added dropwise. The mixture was stirred for 1 h at the same temperature. A solution of 1a (prepared according to WO 200631725, 4.46 g, 12 mmol) in THF (10 mL) was then added. After stirring for 2 h at −78° C., saturated ammonium chloride was added to quench the reaction. The mixture was extracted with ethyl acetate. The organic extract was concentrated in vacuo. The residue was purified by silica gel chromatography (ethyl acetate/hexanes), affording 3b as a yellow solid (1.6 g, 32%). MS=507.1 (M+H$^+$).

Alternative Procedure for Compound 3b Using 1,2-bis-[(chlorodimethyl)silanyl]ethane Instead of Chlorotrimethylsilane To a suspension of 7-bromo-pyrrolo[2,1-f][1,2,4]triazin-4-ylamine (500 mg, 2.35 mmol) in THF (6.5 mL) was added BuLi (1.6 M in hexanes, 1.6 mL) at −78° C. After 30 min., a solution of 1,2-bis-[(chlorodimethyl)silanyl]ethane (538 mg, 2.4 mmol) in THF (1.2 mL) was added. After 45 min., BuLi (1.6 mL) was added. After an additional 30 min., BuLi (1.5 mL) was added. After 30 min., a solution of 1a (610 mg, 1.64 mmol) in THF (2 mL) was then added dropwise. The resulting mixture was stirred at −78° C. for 2 h under argon. Acetic acid (0.7 mL) was added dropwise to quench the reaction, followed by addition of saturated ammonium chloride. The mixture was extracted with ethyl acetate. The organic extract was concentrated in vacuo. The residue was purified by silica gel chromatography (ethyl acetate/hexanes), affording 3b (320 mg, 40%). The starting 1a was also recovered (350 mg) from the chromatography.

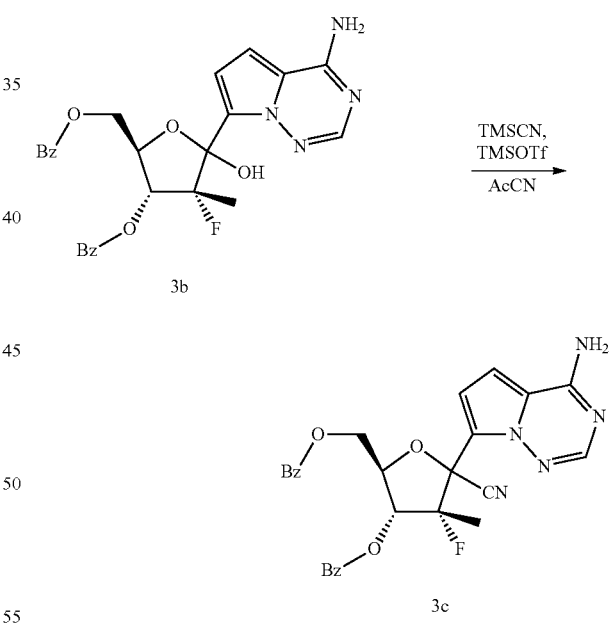

To a solution of compound 3b (50 mg, 0.1 mmol) and TMSCN (67 uL, 0.5 mmol) in acetonitrile (2.0 mL) at 0 was added TMSOTf (91 uL, 0.5 mmol). The reaction mixture was stirred at room temperature for 1 h, then at 65° C. for 3 d. The reaction was quenched with saturated NaHCO$_3$ at room temperature, and diluted with CH$_3$CO$_2$Et. The organic phase was separated, washed with brine, dried over Na$_2$SO$_4$, filtered and concentrated. The residue was purified by RP-HPLC (acetonitrile/water), to give the desired compound 3c (28 mg, 54%). MS=516.1 (M+H$^+$).

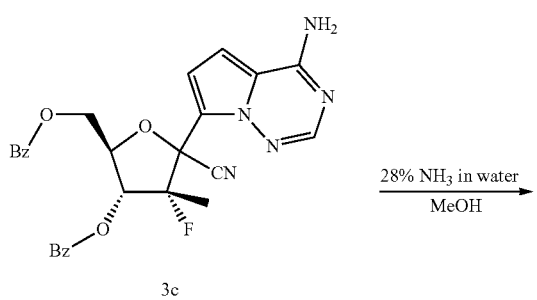

3c

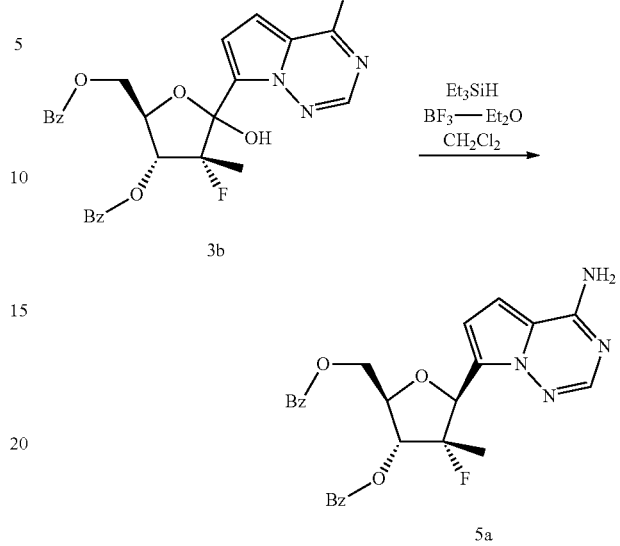

To a solution of 3c (56 mg, 0.11 mmol) in methanol (1.2 mL) was added ammonium hydroxide (28% in water, 0.8 mL) and stirred at room temperature for 16 h. The mixture was concentrated and the residue was purified by RP HPLC (water/acetonitrile), affording compound 3 (20 mg, 60%). $^1$H NMR (500 MHz, D70): δ 7.88 (s, 1H), 7.07 (d, 1H), 6.92 (d, 1H), 4.17 (m, 2H), 4.04 (dd, 1H), 3.87 (dd, 1H), 1.15 (d, 3H). MS=308.1 (M+H$^+$).

Compound 4

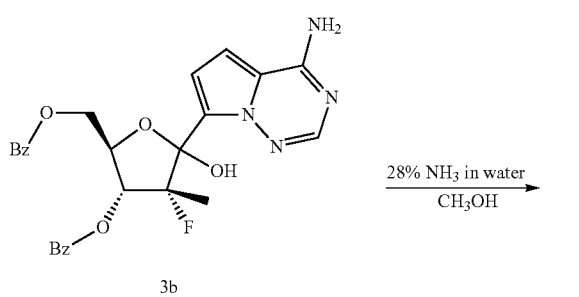

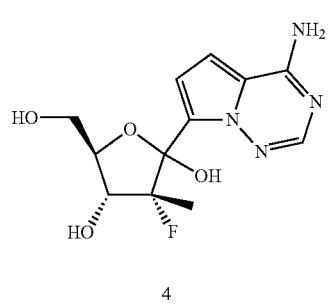

4

To a solution of compound 3b (60 mg, 0.12 mmol) in methanol (0.5 mL) was added ammonium hydroxide (28% in water, 0.5 mL) and stirred at room temperature for 16 h. The mixture was concentrated and the residue was purified by RP HPLC (water/acetonitrile), affording compound 4 (25 mg, 70%). MS=299.1 (M+H$^+$).

Compound 3b was converted to compound 5a by a procedure similar to conversion of 1b to 1c. Compound 5a was then converted to compound 5 by a procedure similar to conversion of 3c to 3. $^1$H NMR (300 MHz, D$_2$O): δ 7.68 (s, 1H), 6.75 (d, J=4.5 Hz, 1H), 6.65 (d, J=4.5 Hz, 1H), 5.65 (d, J=25.2 Hz, 1H), 3.95 (m, 3H), 3.74 (dd, 1H), 0.98 (d, J=22.8 Hz, 3H). $^{19}$F NMR (282 MHz, D$_2$O): δ −154.2. MS=283.2 (M+H$^+$).

General Procedure for Preparation of a Nucleoside Triphosphate:

To a pear-shaped flask (5-15 mL) is charged with a nucleoside (~20 mg). Trimethyl phosphate (0.5-1.0 mL) is added. The solution is cooled with ice-water bath. POCl$_3$ (40-45 mg) is added and stirred at 0° C. until the reaction is complete (1 to 4 h; the reaction progress is monitored by ion-exchange HPLC; analytical samples are prepared by taking ~3 uL of the reaction mixture and diluting it with 1.0 M Et$_3$NH$_2$,CO$_3$ (30-50 uL)). A solution of pyrophosphate-Bu$_3$N (250 mg) and Bu$_3$N (90-105 mg) in acetonitrile or DMF (1-1.5 mL) is then added. The mixture is stirred at 0° C. for 0.3 to 2.5 h, and then the reaction is quenched with 1.0 M Et$_3$NH$_2$CO$_3$ (~5 mL). The resulting mixture is stirred for additional 0.5-1 h while warming up to room temperature. The mixture is concentrated to dryness, re-dissolved in water (4 mL), and purified by ion exchange HPLC. The fractions containing the desired product is concentrated to dryness, dissolved in water (~5 mL), concentrated to dryness, and again dissolved in water (~5 mL). NaHCO$_3$ (30-50 mg) is added and concentrated to dryness. The residue is dissolved in water and concentrated to dryness again. This process is repeated 2-5 times. The residue is then subjected to C-18 HPLC purification, affording the desired product as a sodium or salt. Alternatively, the crude reaction mixture is subjected to C-18 HPLC first and then ion exchange HPLC purification to afford the desired product as a triethylammonium salt.

Compound TP-1

TP-1

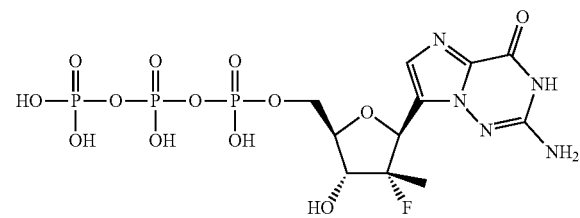

Compound TP-1 was prepared by the general method using Compound 2 as starting material. $^1$H NMR (300 MHz, D$_2$O): δ 7.44 (s, 1H), 5.45 (d, J=25.5 Hz, 1H), 4.0-4.4 (m, 4H), 3.05 (m, NCH$_2$CH$_3$), 1.10 (m, NCH$_2$CH$_3$ and 2'-C—CH$_3$). $^{31}$P NMR (121.4 MHz, D$_2$O): δ −9.5 (d, J=22.1 Hz), −11.0 (d, J=19.9 Hz), −23.2 (t, J=23.0 Hz). $^{19}$F NMR (282 MHz, D$_2$O): δ −153.9.

Compound TP-2

TP-2

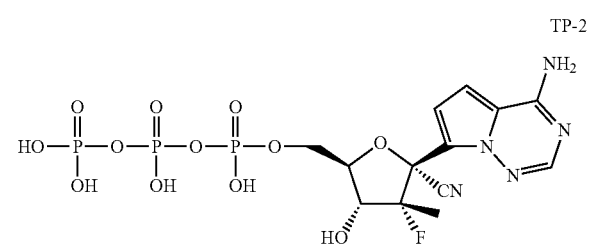

Compound TP-2 was prepared by the general method using Compound 3 as starting material. $^1$H NMR (300 MHz, D$_2$O): δ 7.82 (s, 1H), 7.03 (d, 1H), 6.90 (d, 1H), 4.1-4.4 (m, 4H), 3.05 (m, NCH$_2$CH$_3$), 1.10 (m, NCH$_2$CH$_3$ and 2'-C—CH$_3$). $^{31}$P NMR (121.4 MHz, D70): δ −10.7 (d, J=19.5 Hz), −11.3 (d, J=19.8 Hz), −23.1 (t, J=19.8 Hz).

Compound TP-3

TP-3

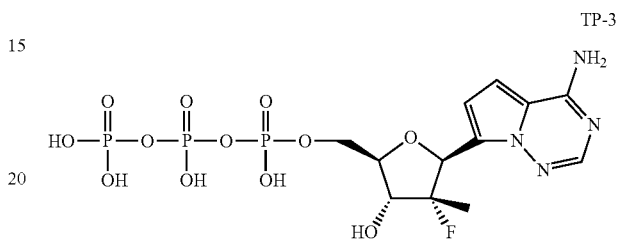

Compound TP-3 was prepared by the general method using Compound 5 as starting material. $^1$H NMR (300 MHz, D$_2$O): δ 7.73 (s, 1H), 6.87 (d, 1H), 6.82 (d, 1H), 5.71 (d, J=24.6 Hz, 1H), 4.0-4.4 (m, 4H), 3.05 (m, NCH$_2$CH$_3$), 1.14 (m, NCH$_2$CH$_3$), 1.00 (d, J=22.8 Hz, 3H, 2'-C—CH$_3$). $^{31}$P NMR (121.4 MHz, D$_2$O): δ −8.1 (d, J=22.1 Hz), −11.1 (d, J=19.9 Hz), −22.7 (t, J=23.0 Hz). $^{19}$F NMR (282 MHz, D70): δ −155.6. MS=520.9 (M−H$^+$). General procedure for preparation of a nucleoside prodrug (Method A):

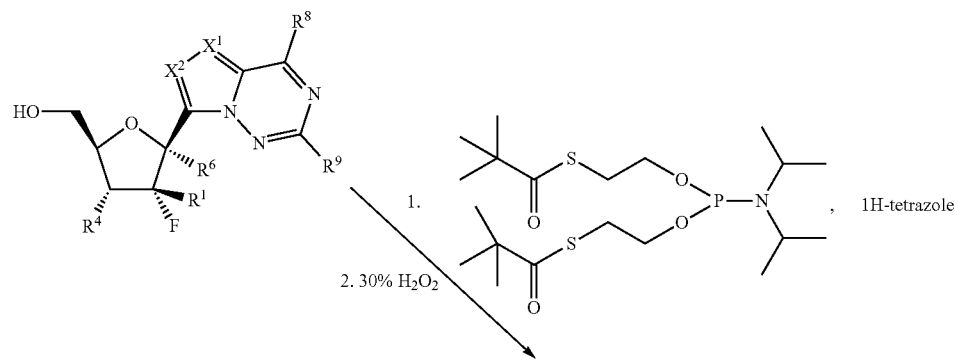

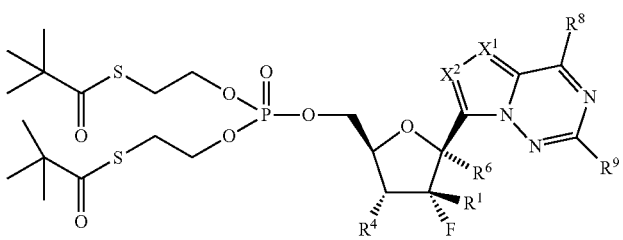

A

To a solution of a nucleoside (0.1 mmol) in trimethylphosphite (1.0 mL) are added 1H-tetrazole (42 mg, 0.6 mmol) followed by addition of 2,2-dimethyl-thiopropionic acid S-(2-{diisopropylamino-[2-(2,2-dimethyl-propionylsulfanyl)-ethoxy]-phosphanyloxy}-ethyl) ester (prepared according to *J. Med. Chem.*, 1985, 38, 3941, 90 mg, 0.2 mmol) at 0° C. After stirring for 2 h, 30% hydrogen peroxide in H$_2$O (140 μL) was added to the mixture. The mixture was then allowed to warm up to room temperature. After 30 min stirring, 1 M Na$_2$S$_2$O$_3$ in H$_2$O (5 mL) was added to quench the reaction. The organic layer was washed with saturated aqueous Na$_2$CO$_3$ (10 mL×2), brine, concentrated in vacuo. The residue was purified by RP-HPLC (MeCN—H$_2$O gradient) to afford a prodrug A.

Compound A-1

A-1

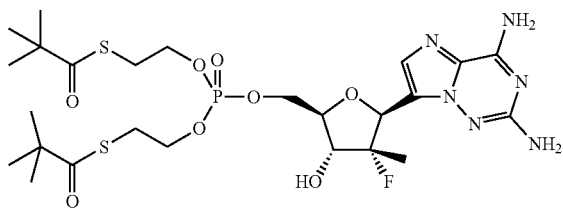

Compound A-1 was prepared by Method A using compound 1 as starting material. $^1$H NMR (400 MHz, CDCl$_3$): δ 7.42 (s, 1H), 5.47 (d, J=26.4 Hz, 1H), 4.95 (brs, 2H), 4.59 (m, 2H), 4.35 (m, 1H, 4'-H), 4.18 (m, 2H, 5'-H), 4.10 (m, 4H), 3.13 (m, 4H), 1.24 (d, 3H), 1.22 (s, 9H), 1.19 (d, 9H). $^{31}$P NMR (161.9 MHz, CDCl$_3$): δ 1.26. MS=667.1 (M+H$^+$).

General Procedure for Preparation of a Nucleoside Prodrug (Method B):

Non-limiting examples of mono-phosphoramidate prodrugs comprising the instant invention may be prepared according to general Scheme 1.

Scheme 1

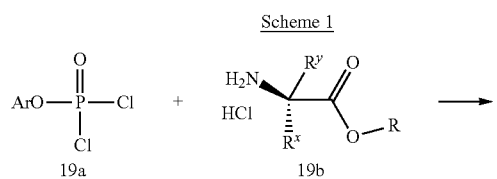

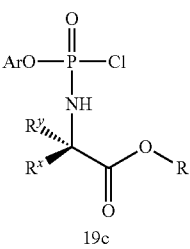

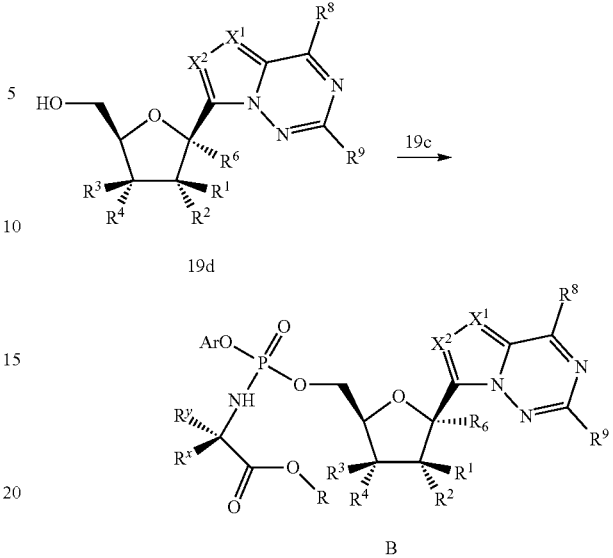

The general procedure comprises the reaction of an amino acid ester salt 19b, e.g., HCl salt, with an aryl dichlorophosphate 19a in the presence of about two to ten equivalents of a suitable base to give the phosphoramidate 19c. Suitable bases include, but are not limited to, imidazoles, pyridines such as lutidine and DMAP, tertiary amines such as triethylamine and DABCO, and substituted amidines such as DBN and DBU. Tertiary amines are particularly preferred. Preferably, the product of each step is used directly in the subsequent steps without recrystallization or chromatography. Specific, but non-limiting, examples of 19a, 19b, and 19c can be found in WO 2006/121820 that is hereby incorporated by reference in its entirety. A nucleoside base 19d reacts with the phosphoramidate 19c in the presence of a suitable base. Suitable bases include, but are not limited to, imidazoles, pyridines such as lutidine and DMAP, tertiary amines such as triethylamine and DABCO, and substituted amidines such as DBN and DBU. The product B may be isolated by recrystallization and/or chromatography.

Compound B-1

B-1

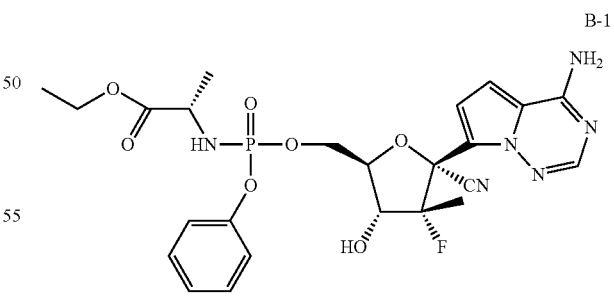

Phenyl ethoxyalaninyl phosphorochloridate (124 mg, 0.42 mmol; prepared according to McGuigan et al, *J. Med. Chem.* 1993, 36, 1048-1052) was added to a mixture of Compound 3 (20 mg, 0.065 mmol) and N-methylimidazole (42 uL, 0.52 mmol) in anhydrous trimethyl phosphate (0.8 mL). The reaction mixture is stirred for 3 h at room temperature, and then methanol was added to quench the reaction. The methanol solvent is removed under reduced pressure. The residue was purified by reverse-phase HPLC and then by silica gel column chromatography (100% ethyl acetate), affording compound B-1 (10 mg, 27%). $^{31}$P NMR (121.4 MHz, CDCl$_3$): δ −3.42, 3.77. MS=563.0 (M+H$^+$), 561.0 (M Compound B-2

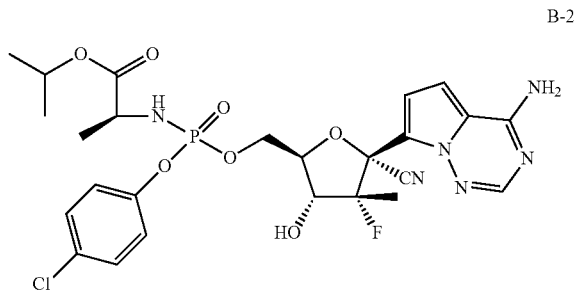

About 3.1 mmol of 4-chlorophenyl 2-propyloxyalaninyl phosphorochloridate (prepared according to McGuigan et al, J. Med. Chem. 1993, 36, 1048-1052) is added to a mixture of about 0.5 mmol of Compound 3 and about 3.8 mmol of N-methylimidazole in about 3 mL anhydrous trimethyl phosphate. The reaction mixture is stirred for about one hour to 24 hours at room temperature and methanol is added to quench the reaction. The methanol solvent is removed under reduced pressure. The residue is purified by reverse-phase HPLC to give compound B-2.

Compound B-3

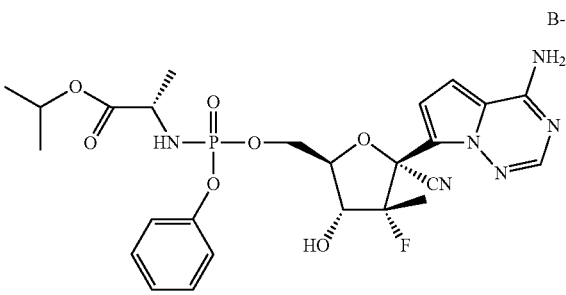

Compound B-3 was obtained by a similar procedure used for compound B-1. $^{31}$P NMR (121.4 MHz, CDCl$_3$): δ −3.50, 3.76. MS=577.2 (M+H$^+$).

Compound B-4

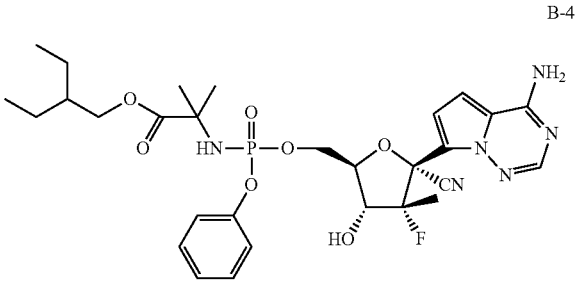

Compound B-4 was obtained by a similar procedure used for compound B-1. $^{31}$P NMR (162 MHz, CD$_3$OD): δ 2.2. MS=633.4 (M+H$^+$).

Compound B-5

B-5

Compound B-5 was obtained by a similar procedure used for compound B-1. $^{31}$P NMR (162 MHz, CDCl$_3$): δ 4.15, 4.27. MS=549.3 (M+H$^+$).

Compound B-6

B-6

Compound B-6 was obtained by a similar procedure used for compound B-1. $^{31}$P NMR (162 MHz, CDCl$_3$): δ 3.50, 4.07. MS=613.1 (M+

Compound B-7

B-7

Compound B-7 was obtained by a similar procedure used for compound B-1, using compound 5 as parent nucleoside. $^{31}$P NMR (162 MHz, CDCl$_3$): δ 3.37, 3.97. MS=538.1 (M+H$^+$).

Compound B-8

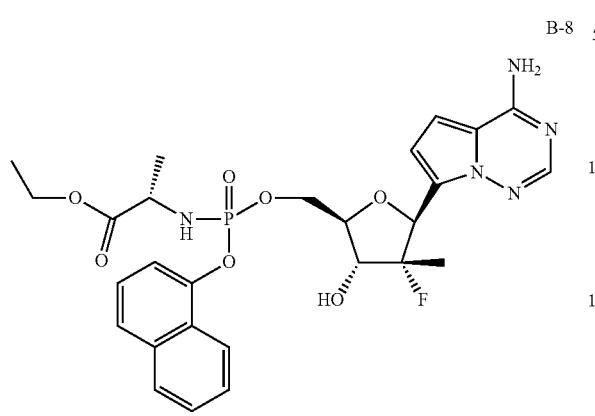

Compound B-8 was obtained by a similar procedure used for compound B-1, using compound 5 as parent nucleoside. $^{31}$P NMR (162 MHz, CDCl$_3$): δ 3.69, 4.39. MS=588.1 (M+H$^+$).

Alternative Procedure for Preparation of a Nucleoside Prodrug (Method C):

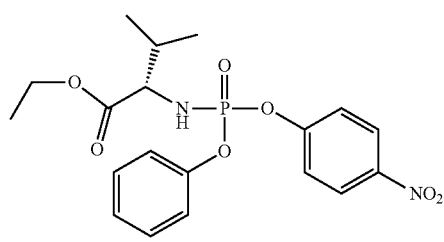

Into a flask containing ethyl L-valine hydrochloride (2.5 g, 13.8 mmoL, 1 equiv.) was added CH$_2$Cl$_2$ (46 mL, 0.3 M) and phenyl dichlorophosphate (2.1 mL, 13.8 mmoL, 1 equiv.) before being cooled to −10° C. After 10 minutes, TEA (3.8 mL, 13.8 mmoL, 1 equiv) was added slowly to the reaction mixture over five minutes. The reaction was allowed to proceed for an hour before p-nitrophenol (1.9 g, 13.8 mmoL, 1 equiv.) was added to the reaction mixture followed by addition of more TEA (3.8 mL, 13.8 mmoL, 1 equiv.) over five minutes. The reaction was allowed to warm up and proceed for another two hours. The reaction was concentrated in vacuo and taken up in diethyl ether (200 mL). The insoluble salts were filtered off and the filtrate concentrated in vacuo. Flash column chromatography was carried out using 4/1 Hex/EtOAc to furnish a clear oil as C-1a.

$^1$H NMR (400 MHz, CDCl$_3$): d 8.21 (s, 2H), 7.41-7.20 (m, 7H), 4.22-4.05 (m, 3H), 2.46 (s, 2H), 1.99 (dd, J=23.0, 20.1 Hz, 2H), 1.68 (s, 1H), 1.20-1.05 (m, 8H). $^{31}$P NMR (162 MHz, CDCl$_3$): d −2.79 (dd, J=28.0, 4.2 Hz).

LC MS m/z 422.99 [M+H$^+$].

Compound C-1

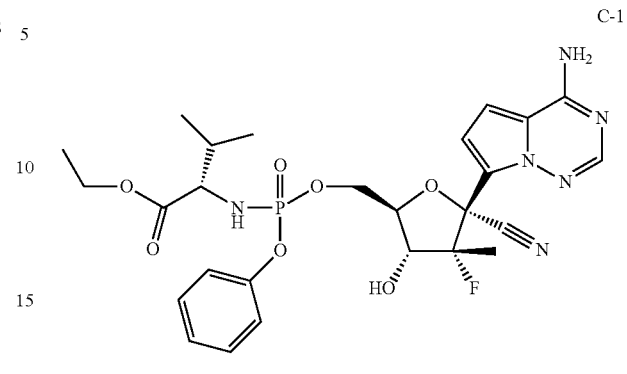

Into a flask containing compound 3 (70 mg, 0.23 mmoL, 1 equiv.) was added THF (1 mL, 0.2 M) and NMP (1 mL, 0.2 M) before cooling to 0° C. t-BuMgCl (560 μL, 2.5 equiv., 1M THF) was added slowly and allowed to stir for 5 minutes before the above phenolate C-1a (207 mg, 0.46 mmoL, 2 equiv. dissolved in 500 μL of THF) was added. The reaction mixture was warmed to 50° C. The reaction was monitored by LCMS. Once the reaction was complete, the mixture was then concentrated in vacuo, and the residue was purified by HPLC, affording Compound C-1.

$^1$H NMR (400 MHz, CDCl$_3$) d 7.87 (s, 1H). 7.24-7.10 (On, 4H), 7.03 (t, J=7.2 Hz, 1H), 6.81 (d, J=4.6 Hz, 1H), 6.52 (d, J=4.7 Hz, 1H), 5.61 (s, 2H), 4.46 (dd, J=24.0, 11.4 Hz, 2H), 4.33-4.14 (m, 2H), 4.06 (dt, J=7.2, 4.2 Hz, 2H), 3.82-3.70 (m, 1H), 3.63 (t, J=10.6 Hz, 2H), 1.98 (s, 1H), 1.17 (dd, J=14.8, 7.6 Hz, 3H), 0.82 (dd, J=22.8, 6.8 Hz, 6H).

$^{31}$P NMR (162 MHz, CDCl$_3$): d 5.11.

$^{19}$F NMR (376 MHz, CDCl$_3$): d −152.28.

LC MS m/z 591.21 [M+H$^+$]

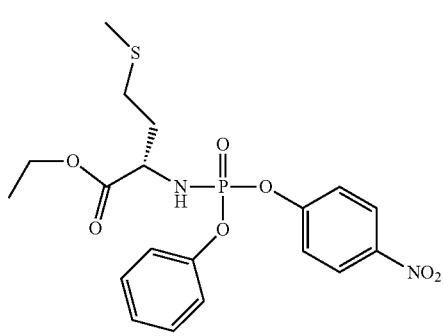

Compound C-2a was obtained in a procedure similar to that exemplified for Compound C-1a but using the methionine ester.

$^1$H NMR (400 MHz, CDCl$_3$) d 8.19 (s, 2H), 7.44-7.03 (m, 7H), 4.11 (s, 2H), 3.81 (d, J=44.5 Hz, 1H), 2.04 (s, 3H), 1.61 (s, 2H), 1.21 (d, J=6.1 Hz, 2H), 1.01-0.65 (m, 4H).

$^{31}$P NMR (162 MHz, CDCl$_3$) d −2.00 (d, J=12.9 Hz).

LC MS m/z 455.03 [M+H$^+$].

Compound C-2

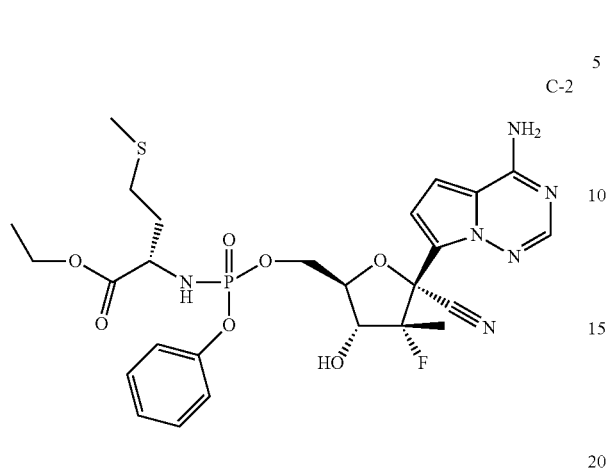

C-3

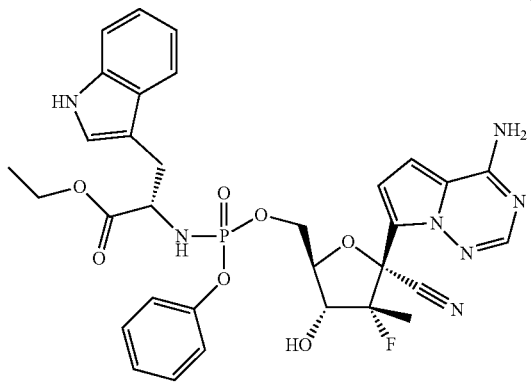

Compound C-2 was obtained in a procedure similar to that exemplified for Compound C-1 using Compound 3 and C-2a.

$^1$H NMR (400 MHz, CDCl$_3$) d 7.96 (d, J=15.8 Hz, 1H), 7.40-7.06 (m, 13H), 6.93 (d, J=6.7 Hz, 1H), 6.70 (s, 1H), 5.98 (s, 1H), 4.54 (dd, J=21.6, 11.7 Hz, 2H), 4.32 (d, J=12.0 Hz, 2H), 4.14 (dt, J=13.0, 6.4 Hz, 4H), 2.44 (d, J=7.5 Hz, 2H), 2.00 (d, J=16.2 Hz, 5H), 1.89 (s, 2H), 1.35-1.13 (m, 7H).

$^{31}$P NMR (162 MHz, CDCl$_3$) d 4.12, 3.58.

$^{19}$F NMR (376 MHz, CDCl$_3$) d −152.28 (s).

LC MS m/z 623.27 [M+H$^+$].

Compound C-3 was obtained in a procedure similar to that exemplified for Compound C-1 using Compound 3 and C-3a.

$^1$H NMR (400 MHz, CDCl$_3$) d 8.27 (s, 1H), 7.84 (s, 1H), 7.47 (s, 1H), 7.36-6.77 (m, 11H), 6.57 (s, 1H), 4.40-3.96 (m, 6H), 3.20 (s, 4H), 2.60 (s, 1H), 1.30-1.04 (m, 6H).

$^{31}$P NMR (162 MHz, CDCl$_3$) d 4.02, 3.75

$^{19}$F NMR (376 MHz, CDCl$_3$) d −152.13.

LC MS m/z 678.32 [M+H$^+$].

C-3a

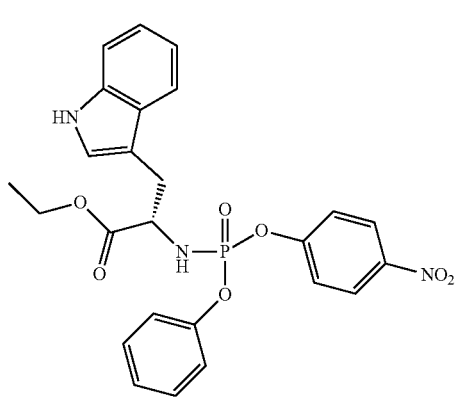

C-4a

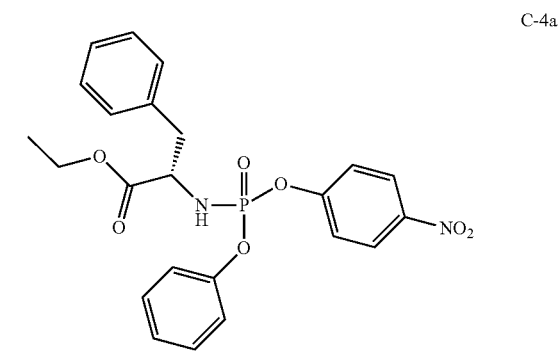

Compound C-3a was obtained in a procedure similar to that exemplified for Compound C-1a but using a tryptophan ester.

$^1$H NMR (400 MHz, CDCl$_3$) d 8.18-8.03 (m, 3H), 7.29-7.08 (m, 8H), 7.36-6.98 (m, 3H), 4.41-4.11 (m, 1H), 4.15-3.95 (m 2H), 3.68-3.80 (m, 1H), 3.33-3.04 (m, 2H), 1.06-1.17 (m, 3H).

$^{31}$P NMR (162 MHz, CDCl$_3$) d −2.87, −2.99.

LC MS m/z 510.03 [M+H$^+$].

Compound C-4a was obtained in a procedure similar to that exemplified for Compound C-1a by substituting the phenylalanine ester.

NMR (400 MHz, CDCl$_3$) d 8.15 (t, J=8.7 Hz, 2H), 7.43-7.11 (m, 10H), 7.04 (ddd, J=11.4, 6.7, 2.9 Hz, 2H), 4.32 (ddd, J=15.3, 11.3, 6.1 Hz, 4H), 4.15-3.99 (m, 7H), 3.74 (td, J=11.0, 5.0 Hz, 8H), 3.01 (d, J=5.7 Hz, 2H), 1.17 (td, J=7.1, 5.2 Hz, 2H).

$^{31}$P NMR (162 MHz, CDCl$_3$) d −2.97, −2.99.

LC MS m/z 471.03 [M+H$^+$].

Compound C-4

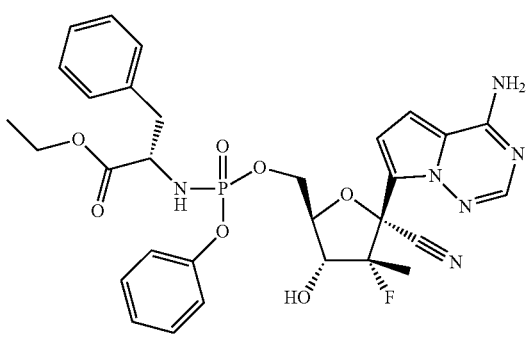

Compound C-4 was obtained in a procedure similar to that exemplified for Compound C-1 using Compound 3 and C-4a.

NMR (400 MHz, CDCl$_3$) d 7.92 (d, J=13.2 Hz, 1H), 7.46-6.97 (m, 17H), 6.91 (s, 1H), 6.75 (s, 1H), 4.10 (dd, J=29.6, 19.2 Hz, 8H), 2.97 (s, 3H), 1.32-1.05 (m, 7H).
$^{31}$P NMR (162 MHz, CDCl$_3$) d 5.11.
$^{19}$F NMR (376 MHz, CDCl$_3$) d −152.34 (s).
LC MS m/z 639.24 [M+H$^+$].

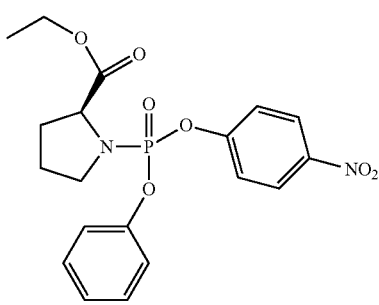

Compound C-5a was obtained in a procedure similar to that exemplified for Compound C-1a but using the proline ester.
$^1$H NMR (400 MHz, CDCl$_3$) d 8.20 (d, J=7.8 Hz, 2H), 7.45-7.08 (m, 7H), 4.37 (td, 8.0, 3.8 Hz, 2H), 4.17-3.98 (m, 2H), 3.61-3.34 (m, 2H), 2.21-1.77 (m, 3H), 1.19 (td, 7.1, 3.8 Hz, 3H).
$^{31}$P NMR (162 MHz, CDCl$_3$) d −3.92, −3.96.
LC MS m/z 420.98 [M+H$^+$].

Compound C-5

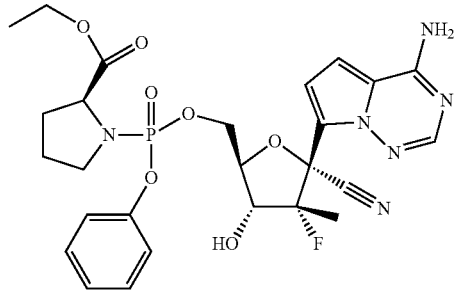

Compound C-5 was obtained in a procedure similar to that exemplified for Compound C-1 using Compound 3 and C-5a.

$^1$H NMR (400 MHz, CDCl$_3$) d 7.95 (d, J=4.5 Hz, 1H), 7.39-7.10 (m, 4H), 6.92 (dd, J=16.0, 4.6 Hz, 1H), 6.69 (s, 1H), 6.03 (bs, 2H), 4.46-4.36 (m, 1H), 4.36-3.96 (m, 4H), 3.37 (d, J=58.9 Hz, 2H), 2.26-1.66 (m, 4H), 1.39-1.12 (m, 8H).
$^{31}$P NMR (162 MHz, CDCl$_3$) d 3.47, 2.75.
$^{19}$F NMR (376 MHz, CDCl$_3$) d −152.36.
LC MS m/z 589.14 [M+H$^+$].

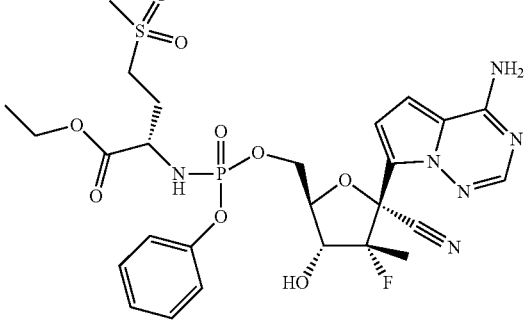

Compound C-6 was obtained in a procedure similar to that exemplified for Compound C-1 using Compound 3 and the sulphone analog of C-1a.
$^1$H NMR (400 MHz, CDCl$_3$) d 7.93 (s, 1H), 7.89 (s, 1H), 7.35-7.01 (m, 5H), 6.93 (d, J=2.8 Hz, 1H), 6.58 (d, J=2.8 Hz, 1H), 5.79 (bs, 2H), 4.30 (s, 6H), 4.11 (d, J=7.0 Hz, 6H), 3.10-2.84 (m, 3H), 2.75 (s, 3H), 2.54 (s, 6H), 1.31-1.15 (m, 6H).
$^{31}$P NMR (162 MHz, CDCl$_3$) d 3.39, 3.33.
$^{19}$F NMR (376 MHz, CDCl$_3$) d −152.40
LC MS m/z 655.24 [M+H$^+$].

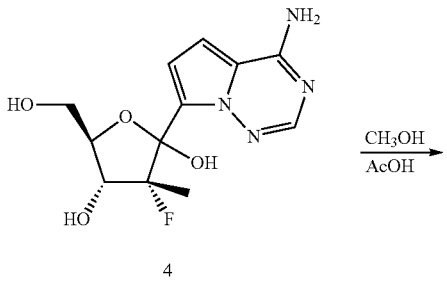

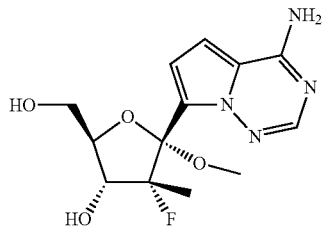

Compound 4 (about 0.04 mmol) and anhydrous MeOH (about 5 mL) is treated with acetic acid (about 5 mL) and the reaction is stirred overnight at room temperature. Saturated NaHCO$_3$ is added to neutralize the reaction mixture and the crude material is purified using a HPLC system (acetonitrile-H$_2$O) to give 6.

Compound 7

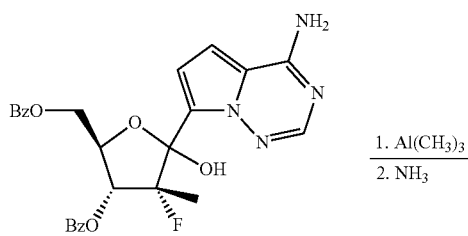
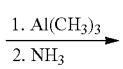

3b

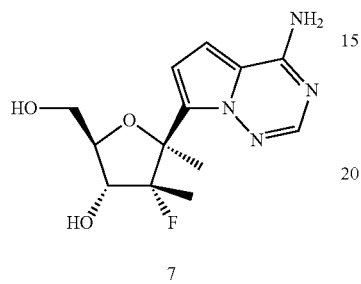

7

To a dry, argon purged round bottom flask (50 mL) is added compound 3b (about 0.39 mmol) and anhydrous dichloromethane (about 10 mL). The flask is placed into a dry ice/acetone bath (~−78° C.) and the solution is stirred for about 10 min. BF$_3$-Et$_{20}$ (about 0.10 mL) is added dropwise and the reaction is stirred for about 10 min. AlMe$_3$ (about 1.16 mmol, 2.0 M in toluene) is then added. After a few minutes, the dry ice/acetone bath is removed and the reaction mixture is stirred at room temperature to about 45° C. over about 4 h to about 4 d. A solution of pyridine (about 2 mL) in MeOH (about 10 mL) is added and the solvent is removed under reduced pressure. The crude material is purified by chromatography and is treated with ammonium hydroxide in methanol for about 16 h at about room temperature. The mixture is concentrated and the residue is purified by HPLC to give 7.

Compound 8

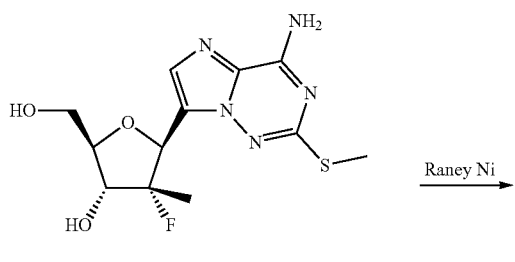

1d

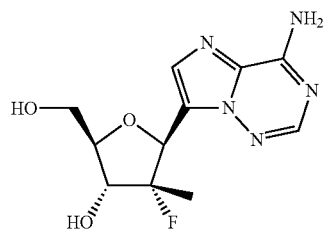

8

Raney Ni (about 500 mg) is neutralized by washing with H$_2$O, and added to a solution of 1d (about 100 mg) in ethanol (about 10 ml). The mixture is then heated to about 35 to about 80° C. until the reaction is complete. The catalyst is removed by filtration and the solution is concentrated in vacuo. The mixture is concentrated and the residue is purified by HPLC to give 8.

Compound 9

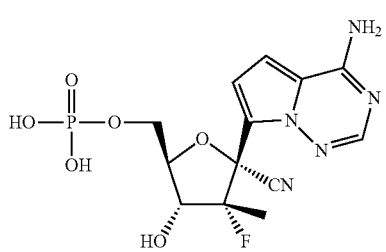

9

Into a flask containing Compound 3 (120 mg, 0.39 mmoL, 1 equiv.) was added PO(OMe)$_3$ (1.5 mL, 0.25 M) and cooled to 0° C. before adding POCl$_3$ (125 µL, ⅟$_{37}$ mmoL, 3.5 equiv.). The reaction mixture was allowed to stir for 5 hr before the reaction was quenched with water. It was directly purified by HPLC to furnish the monophosphate Compound 9.

LC MS m/z 387.95 [M+H$^+$].

Compound 10

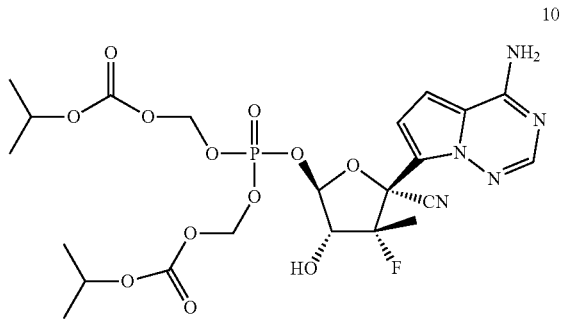

10

Into a flask containing Compound 9 (30 mg, 0.078 mmoL, 1 equiv.) was added. NMP (0.8 mL, 0.1 M) followed by addition of TEA (43 µL, 0.31 mmoL, 4 equiv.), tetrabutylammonium bromide (25 mg, 0.078 mmoL, 1 equiv.) before adding chloromethylisopropyl carbonate (60 µL, 0.38 mmoL, 5 equiv.). The reaction mixture was heated to 50° C. and allowed to stir overnight. It was purified directly by HPLC, affording Compound 10.

$^1$H NMR (400 MHz, CDCl$_3$) d 7.98 (s, 1H), 7.01 (d, J=4.7 Hz, 1H), 6.72 (d, J=4.7 Hz, 1H), 6.04 (bs, 2H), 5.74-5.61 (m, 4H), 4.91 (ddt, J=12.6, 9.4, 6.3 Hz, 2H), 4.64-4.28 (m, 4H), 1.37-1.19 (m, 15H).

31P NMR (162 MHz, CDCl$_3$) d −4.06.

$^{19}$F NMR (376 MHz, CDCl$_3$) d −76.58, −151.95 TFA salt.

LC MS m/z 620.03[M+H$^+$].

Compound 11

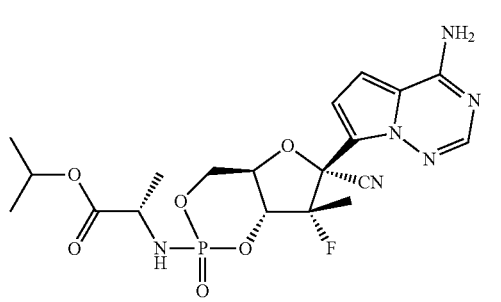

A solution of Compound B-2 in DMSO is treated with about 3 mole equivalents of potassium t-butoxide for about 15 min to 24 hours. The reaction is quenched with 1N HCl and Compound 11 is isolated by reverse-phase HPLC.

trated. The residue is purified by RP-HPLC then dissolved in methanol (about 1 mL). Ammonium hydroxide (28% in water, about 0.8 mL) is added and the mixture is stirred at about room temperature for 16 h. The mixture is concentrated and the residue is purified by RP HPLC to give 12.

Compound 13

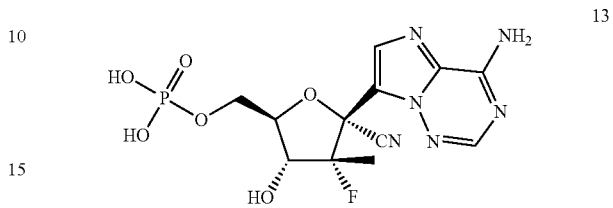

Compound 13 is prepared in the same manner as Compound 9 using Compound 12 as a starting material.

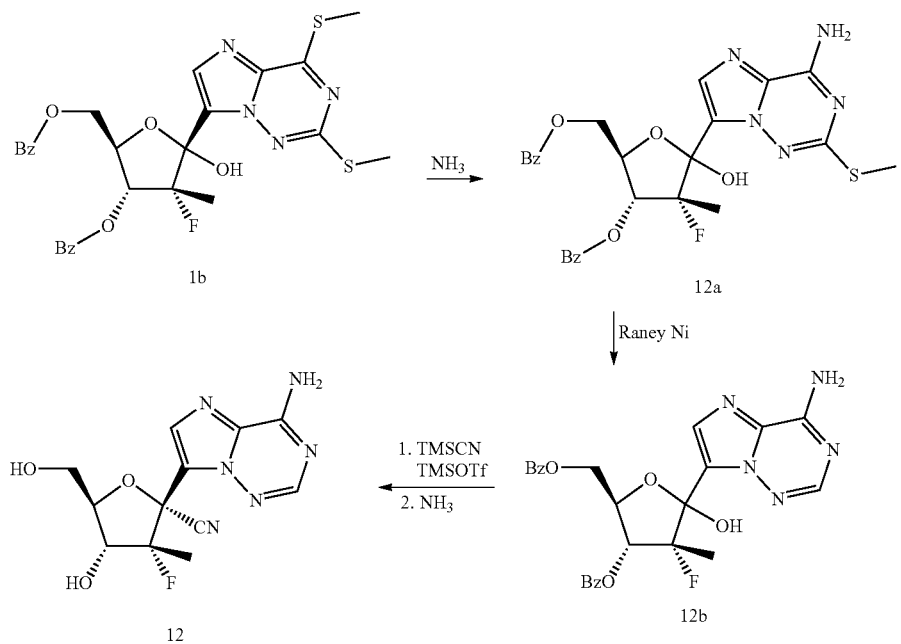

Compound 1b (about 1 mmol) is placed in a steel bomb reactor. The reactor is charged with liquid ammonia (about 30 mL) and the mixture is stirred at about 0 to 50° C. for about 16 h. The ammonia is evaporated and the residue is purified to give 12a. A solution of 12a (about 100 mg) in ethanol (about 10 ml) is treated with Raney Ni (about 500 mg) that is neutralized by washing with $H_2O$. The mixture is then heated to about 35 to about 80° C. until the reaction is complete. The catalyst is removed by filtration and the solution is concentrated in vacuo. The mixture is concentrated and the residue is purified by HPLC to give 12b. To a solution of compound 12b (about 50 mg) and TMSCN (about 0.5 mmol) in acetonitrile (about 2.0 mL) at about 0° C. is added TMSOTf (about 0.5 mmol). The reaction mixture is stirred at room temperature for about 1 h, then at 65° C. for about 3 d. The reaction is quenched with saturated $NaHCO_3$ at room temperature, and diluted with $CH_3CO_2Et$. The organic phase was separated, washed with brine, dried over $Na_2SO_4$, filtered and concen- Compound 14

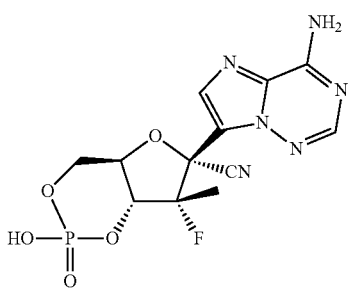

Compound 14 is prepared by treating Compound 13 with about one to about five equivalents of DCC in pyridine and heating the reaction to reflux for about one to about 24 hours. Compound 14 is isolated by conventional ion exchange and reverse-phase HPLC.

Compound 15

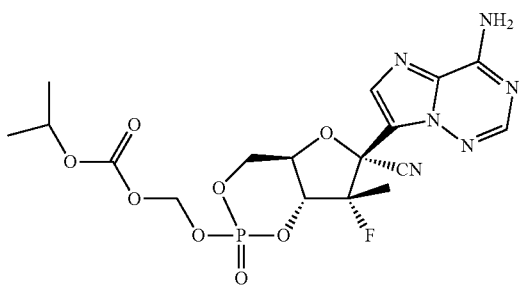

A solution of about 0.4 mmol of Compound 14 in about 10 mL of DMF is treated with about 0.8 mmol of DIPEA and about 0.8 mmol of chloromethyl isopropyl carbonate (WO2007/027248). The reaction is heated to about 25 to about 80° C. for about 15 min to about 24 hours. The solvent is removed under vacuum and the residue is purified by HPLC to give Compound 15.

Compound 16

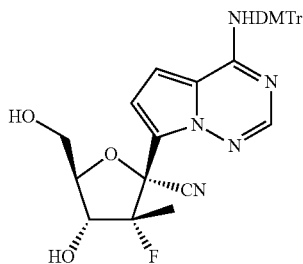

Compound 3 (about 0.22 mmol) is dissolved in anhydrous pyridine (about 2 mL) and chlorotrimethylsilane (about 0.17 mL) is added. The mixture is stirred at about 0 to about 25° C. for about one to about 24 hours. Additional chlorotrimethylsilane (about 0.1 mL) is added and the reaction is stirred for about one to about 24 hours. 4,4'-Dimethoxytrityl chloride (about 0.66 mmol) and DMAP (about 0.11 to about 0.22 mmol) is sequentially added. The mixture is stirred for about one to about 24 hours. A solution of TBAF (1.0 M, about 0.22 mL) in THF is added and the reaction is stirred for about one to about 24 hours. The mixture is partitioned between ethyl acetate and water. The ethyl acetate layer is dried and concentrated. The residue is purified chromatography to afford Compound 16.

Compound 17

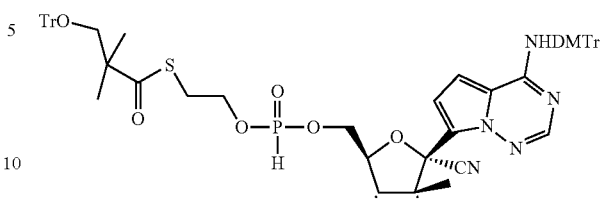

A mixture of about 1.25 mmol of Compound 16 and about 1.9 mmol of triethylammonium 2-(2,2-dimethyl-3-(trityloxy)propanoylthio)ethyl phosphinate (WO2008082601) is dissolved in anhydrous pyridine (about 19 mL). Pivaloyl chloride (about 2.5 mmol) is added dropwise at about −30 to about 0° C. and the solution is stirred at for about 30 min to about 24 hours. The reaction is diluted with methylene chloride and is neutralized with aqueous ammonium chloride (about 0.5M). The methylene chloride phase is evaporated and the residue is dried and is purified by chromatography to give Compound 17.

Compound 18

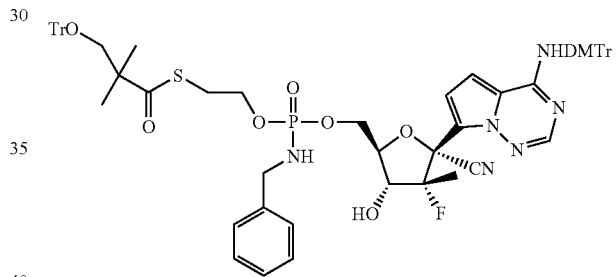

To a solution of about 0.49 mmol of Compound 17 in anhydrous carbon tetrachloride (about 5 mL) is added dropwise benzylamine (about 2.45 mmol). The reaction mixture is stirred for about one to about 24 hours. The solvent is evaporated and the residue is purified by chromatography to give Compound 18.

Compound 20

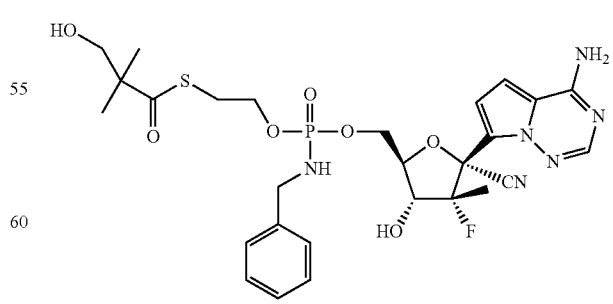

A solution of about 2 mmol of Compound 18 in methylene chloride (about 10 mL) is treated with an aqueous solution of trifluoroacetic acid (90%, about 10 mL). The reaction mixture is stirred at about 25 to about 60° C. for about one to about 24 hours. The reaction mixture is diluted with ethanol, the volatiles are evaporated and the residue is purified by chromatography to give Compound 20.

Compound 21

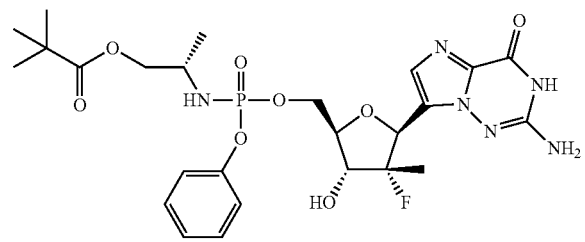

21

About 90 mM Compound 2 in THF is cooled to about −78° C. and about 2.2 to about 5 equivalents of t-butylmagneisum chloride (about 1 M in THF) is added. The mixture is warmed to about 0° C. for about 30 min and is again cooled to about −78° C. A solution of (2S)-2-{[chloro(1-phenoxy)phosphoryl]amino}propyl pivaloate (WO2008085508) (1 M in THF, about 2 equivalents) is added dropwise. The cooling is removed and the reaction is stirred for about one to about 24 hours. The reaction is quenched with water and the mixture is extracted with ethyl acetate. The extracts are dried and evaporated and the residue purified by chromatography to give Compound 21.

Compound 22

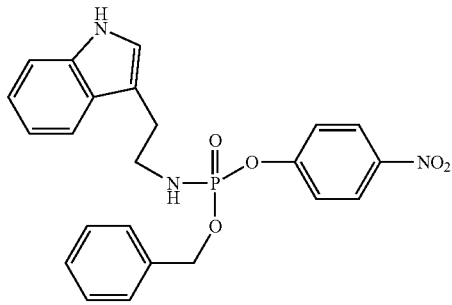

22a

Compound 22a was obtained in a procedure similar to that for preparation of C-1a.

$^1$H NMR (400 MHz, CDCl$_3$) d 8.11 (d, J=9.0 Hz, 2H), 8.02 (s, 1H), 7.48 (t, J=7.5 Hz, 2H), 7.42-7.25 (m, 4H), 7.21 (dt, J=14.9, 5.5 Hz, 2H), 7.08 (t, J=7.3 Hz, 2H), 5.17-5.03 (m, 2H), 4.99 (dd, J=16.5, 9.7 Hz, 2H), 3.44 (s, 1H), 3.35-3.21 (m, 2H), 3.19 (d, J=9.2 Hz, 1H), 3.00-2.80 (m, 2H).

$^{31}$P NMR (162 MHz, CDCl$_3$) d 4.27.

LC MS m/z 452.09 [M+H$^+$].

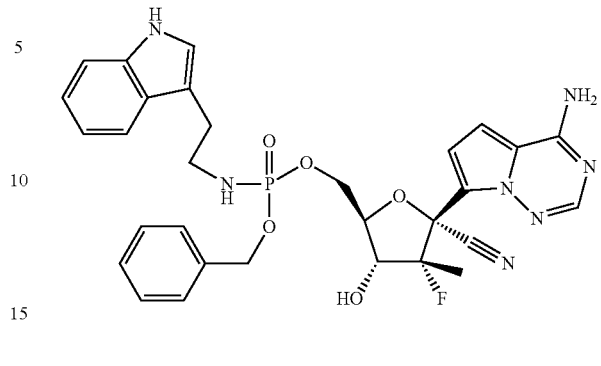

22b

Compound 22b was obtained in a procedure similar to that for preparation of C-1 using Compound 3 and 22a.

$^1$H NMR (400 MHz, CD$_3$OD) d 7.76 (d, J=6.3 Hz, 1H), 7.38 (t, J=8.2 Hz, 1H), 7.27-7.12 (m, 4H), 7.06-6.81 (m, 3H), 6.74 (dd, J=4.6, 3.5 Hz, 1H), 4.95-4.79 (m, 1H), 4.35-3.90 (m, 4H), 3.23 (dt, J=3.2, 1.6 Hz, 3H), 3.18-3.05 (m, 2H), 2.82 (dt, J=14.7, 7.3 Hz, 2H), 1.15 (d, J=22.4 Hz, 3H).

$^{31}$P NMR (162 MHz, CD$_3$OD) δ 10.76, 10.71.

LC MS m/z 620.05 [M+H$^+$].

Compound 22

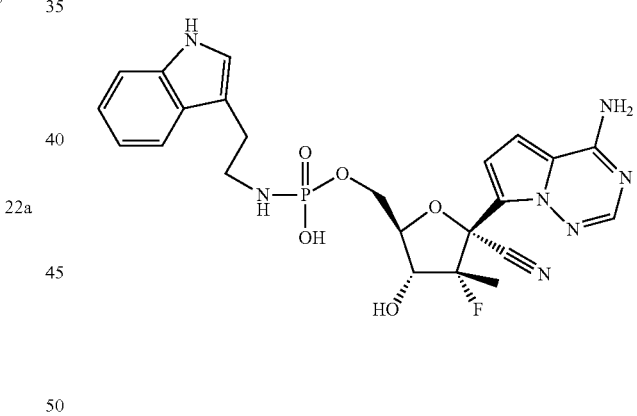

Into a flask containing the 22b (50 mg, 0.08 mmoL, 1 equiv.) was added ethanol (4 mL) followed by Pd(OH)$_2$ (56 mg, 0.08 mmoL, 1 equiv.) and ammonium formate (42 mg, 0.64 mmoL, 8 equiv.). The reaction was heated to 80° C. for about an hour. The solid was filtered off and the material purified by HPLC.

$^1$H NMR (400 MHz, DMSO-d$_6$) d 10.72 (s, 1H), 7.91 (s, 1H), 7.95-7.89 (bs, 2H), 7.41 (d, J=7.7 Hz, 1H), 7.26 (d, J=8.1 Hz, 1H), 7.19-6.66 (m, 3H), 4.20-3.75 (m, 3H), 2.99 (dd, J=16.5, 9.6 Hz, 2H), 2.89-2.70 (m, 2H), 2.48-2.58 (m, 8H), 1.10 (d, J=22.3 Hz, 3H).

$^{31}$P NMR (162 MHz, DMSO-d$_6$) d 7.49.

$^{19}$F NMR (376 MHz, DMSO-d$_6$) d −154.89.

LC MS m/z 530.21 [M+H$^+$].

Compound 23

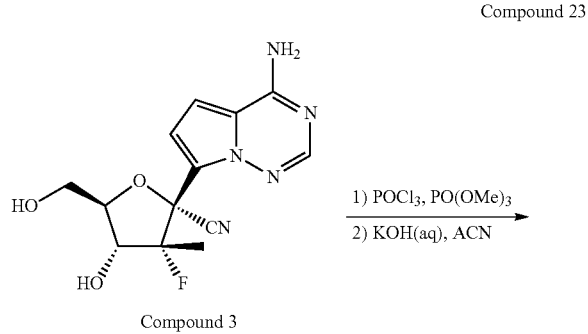

Compound 3

Compound 3 (250 mg, 0.82 mmol) was dissolved in PO(OMe)₃ (5 mL, 0.16M) and cooled to 0° C. under argon. To this stirring solution was added POCl₃ (0.32 mL, 4.1 mmol) slowly dropwise, and the reaction mixture allowed to warm to room temperature for 16 h. The resulting solution was added dropwise to a rapidly stirring solution of acetonitrile (400 mL) and 0.08M aqueous KOH (300 mL). When addition was complete, the reaction progress was checked by LCMS. When the reaction was complete, solvents were removed under reduced pressure. The resulting solid residue was dissolved in water and purified by HPLC to give 140 mg of Compound 23 (yield 47%).

$^1$H-NMR (400 MHz; CD₃OD): d 8.15 (s, 1H), 7.40 (d, 1H; J=4.8 Hz), 7.09 (d, 1H; J=4.8 Hz), 4.64 (dd, 1H; J=24 Hz, 7.2 Hz), 4.50-4.36 (m, 3H), 1.32 (d, 3H; J=22 Hz).

$^{19}$F-NMR (376 MHz; CD₃OD): d −153.11.

$^{31}$P-NMR (162 MHz; CD₃OD): d −2.20.

MS [M+H⁺]=370.2.

Compound 24

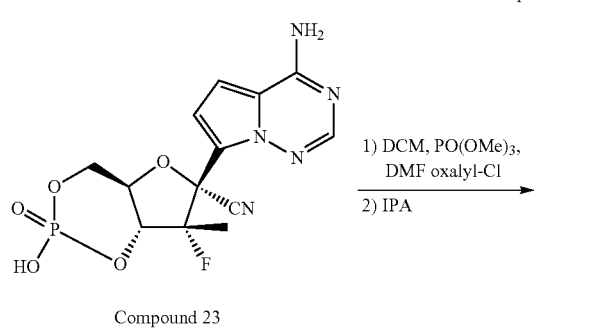

Compound 23

A solution of Compound 23 (7 mg, 0.02 mmol) in DCM (2 L) and PO(OMe)₃ (1 mL) was prepared and cooled to 0° C. To this solution was added oxalyl-Cl (10 uL) followed by DMF (2 uL). The mixture was allowed to stir for 1 min before an aliquot was taken out and quenched in MeOH and then checked by LCMS for activation. Successive amounts of oxalyl-Cl (10 uL) and DMF (2 uL) were added until activation was complete. At this point, a large volume of 2-propanol (5 mL) was added to the reaction mixture and allowed to stir and warm to room temperature. Once the reaction was complete, the solvents were removed under reduced pressure, and the resulting crude material was purified by preperative HPLC to give 5.5 mg of Compound 24 (yield 70%).

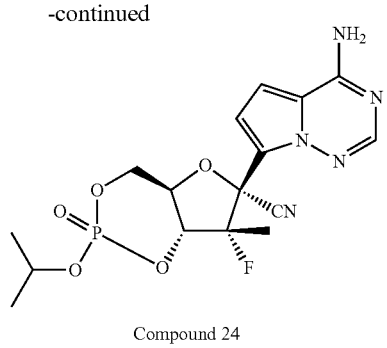

Compound 24

$^1$H-NMR (400 MHz; DMSO-d₆): d 8.26 (br, 1H), 8.15 (br, 1H), 7.97 (s, 1H), 7.00 (d, 1H; J=4.4 Hz), 6.88 (d, 1H; J=4.4 Hz), 4.59-4.51 (m, 2H), 4.37-4.25 (m, 2H), 1.23 (d, 3H; J=22.8 Hz).

$^{19}$F-NMR (376 MHz; CD₃OD) d −151.72.

$^{31}$P-NMR (162 MHz; CD₃OD): d −5.69.

MS [M+H⁺]412.0.

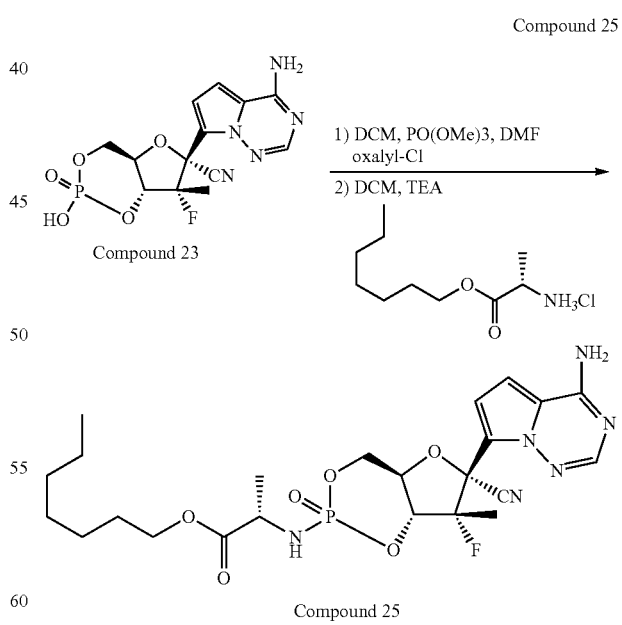

Compound 25

Compound 25 was prepared from Compound 23 in a matter similar to that of Compound 24 substituting the heptyl ester of alanine for 2-propanol (yield 5.3%).

$^1$H-NMR (400 MHz; CD₃OD): d 7.91 (s, 1H), 6.98 (d, 1H; J=4.8 Hz), 6.92 (d, 1H; J=4.8 Hz), 5.29 (dd, 1H; J=24.4 Hz, 8.8 Hz), 4.66-4.60 (an, 2H), 4.48-4.40 (m, 1H), 4.15-4.11 (m, 3H), 3.92 (dd, 1H; J=9.6 Hz, 7.2 Hz), 1.67-1.64 (m, 3H), 1.40-1.27 (m, 15H), 0.91-0.87 (m, 6H).
$^{19}$F-NMR (376 MHz; CD$_3$OD): d −151.46.
$^{31}$P-NMR (162 MHz; CD$_3$OD): d 7.36.
MS [M+H$^+$]=539.4.

Compound 26

Compound 26

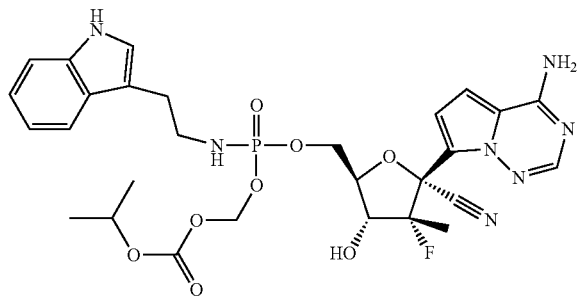

Compound 26 is prepared from compound 22 in a matter similar to that for preparation of compound 10.

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

Cell-Based Flavivirus Immunodetection Assay

BHK21 or A549 cells are trypsinized, counted and diluted to 2×10$^5$ cells/mL in Hams F-12 media (A549 cells) or RPMI-1640 media (BHK21 cells) supplemented with 2% fetal bovine serum (FBS) and 1% penicillin/streptomycin. 2×10$^4$ cells are dispensed in a clear 96-well tissue culture plates per well and placed at 37° C., 5% CO$_2$ overnight. On the next day, the cells are infected with viruses at multiplicity of infection (MOI) of 0.3 in the presence of varied concentrations of test compounds for 1 hour at 37° C. and 5% CO, for another 48 hours. The cells are washed once with PBS and fixed with cold methanol for 10 min. After washing twice with PBS, the fixed cells are blocked with PBS containing 1% FBS and 0.05% Tween-20 for 1 hour at room temperature. The primary antibody solution (4G2) is then added at a concentration of 1:20 to 1:100 in PBS containing 1% FBS and 0.05% Tween-20 for 3 hours. The cells are then washed three times with PBS followed by one hour incubation with horseradish peroxidase (HRP)-conjugated anti-mouse IgG (Sigma, 1:2000 dilution). After washing three times with PBS. 50 microliters of 3,3',5, 5'-tetramethylbenzidine (TMB) substrate solution (Sigma) is added to each well for two minutes. The reaction is stopped by addition of 0.5 M sulfuric acid. The plates are read at 450 nm absorbance for viral load quantification. After measurement, the cells are washed three times with PBS followed by incubation with propidium iodide for 5 min. The plate is read in a Tecan. Safire™ reader (excitation 537 nm, emission 617 nm) for cell number quantification. Dose response curves are plotted from the mean absorbance versus the log of the concentration of test compounds. The EC$_{50}$ is calculated by non-linear regression analysis. A positive control such as N-nonyl-deoxynojirimycin may be used.

Cell-Based Flavivirus Cytopathic Effect Assay

For testing against West Nile virus or Japanese encephalitis virus, BHK21 cells are trypsinized and diluted to a concentration of 4×10$^5$ cells/mL in RPMI-1640 media supplemented with 2% FBS and 1% penicillin/streptomycin. For testing against dengue virus, Huh7 cells are trypsinized and diluted to a concentration of 4×10$^5$ cells/mL in DMEM media supplemented with 5% FBS and 1% penicillin/streptomycin. A 50 microliter of cell suspension (2×10$^4$ cells) is dispensed per well in a 96-well optical bottom PIT polymer-based plates (Nunc). Cells are grown overnight in culture medium at 37° C., 5% CO$_2$, and then infected with West Nile virus (e.g. B956 strain) or Japanese encephalitis virus (e.g. Nakayama strain) at MOI=0.3, or with dengue virus (e.g. DEN-2 NGC strain) at MOI=1, in the presence of different concentrations of test compounds. The plates containing the virus and the compounds are further incubated at 37° C., 5% CO$_2$ for 72 hours. At the end of incubation, 100 microliters of CellTiter-Glo™ reagent is added into each well. Contents are mixed for 2 minutes on an orbital shaker to induce cell lysis. The plates are incubated at room temperature for 10 minutes to stabilize luminescent signal. Lumnescence reading is recorded using a plate reader. A positive control such as N-nonyl-deoxynojirimycin may be used.

Antiviral Activity in a Mouse Model of Dengue Infection.

Compounds are tested in vivo in a mouse model of dengue virus infection (Schul et al. J. Infectious Dis. 2007; 195:665-74). Six to ten week old AG129 mice (B&K Universal Ltd, H11, UK) are housed in individually ventilated cages. Mice are injected intraperitoneally with 0.4 mL TSV01 dengue virus 2 suspension. Blood samples are taken by retro orbital puncture under isoflurane anaesthesia. Blood samples are collected in tubes containing sodium citrate to a final concentration of 0.4%, and immediately centrifuged for 3 minutes at 6000 g to obtain plasma. Plasma (20 microliters) is diluted in 780 microliters RPMI-1640 medium and snap frozen in liquid nitrogen for plaque assay analysis. The remaining plasma is reserved for cytokine and NS1 protein level determination. Mice develop dengue viremia rising over several days, peaking on day 3 post-infection.

For testing of antiviral activity, a compound of the invention is dissolved in vehicle fluid, e.g. 10% ethanol, 30% PEG 300 and 60% D5W (5% dextrose in water; or 6N HCl (1.5 eq):1N NaOH (pH adjusted to 3.5):100 mM citrate buffer pH 3.5 (0.9% v/v:2.5% v/v:96.6% v/v). Thirty six 6-10 week old AG129 mice are divided into six groups of six mice each. All mice are infected with dengue virus as described above (day 0). Group 1 is dosed by oral gavage of 200 mL/mouse with 0.2 mg/kg of a compound of the invention twice a day (once early in the morning and once late in the afternoon) for three consecutive days starting on day 0 (first dose just before dengue infection). Groups 2, 3 and 4 are dosed the same way with 1 mg/kg, 5 mg/kg and 25 mg/kg of the compound, respectively. A positive control may be used, such as (2R,3R,4R,5R)-2-(2-amino-6-hydroxy-purin-9-yl)-5-hydroxymethyl-3-methyl-tetrahydro-furan-3,4-diol, dosed by oral gavage of 200 microliters/mouse the same way as the previous groups. A further group is treated with only vehicle fluid.

On day 3 post-infection approximately 100 microliter blood samples (anti-coagulated with sodium citrate) are taken from the mice by retro-orbital puncture under isoflurane anaesthesia. Plasma is obtained from each blood sample by centrifugation and snap frozen in liquid nitrogen for plague assay analysis. The collected plasma samples are analyzed by plague assay as described in Schul et al. Cytokines are also analysed as as described by Schul. NS1 protein levels are analysed using a Platelia™ kit (BioRad Laboratories). An anti-viral effect is indicated by a reduction in cytokine levels and/or NS1 protein levels.

Typically, reductions in viremia of about 5-100 fold, more typically 10-60 fold, most typically 20-30 fold, are obtained with 5-50 mg/kg bid dosages of the compounds of the invention.

HCV IC$_{50}$ Determination

Assay Protocol: Either wild type or S282T (Migliaccio, et al, *J. Biol. Chem.* 2003, 49164-49170; Klumpp, et al., *J. Biol. Chem.* 2006, 3793-3799) mutant polymerase enzyme was used in this assay. NS5b polymerase assay (40 μL) was assembled by adding 28 μL polymerase mixture (final concentration: 50 mM Tris-HCl at pH 7.5, 10 mM KCL, 5 mM MgCl$_2$, 1 mM DTT, 10 mM EDTA, 4 ng/μL of RNA template, and 75 nM HCV Δ21 NS5b polymerase) to assay plates followed by 4 μL of compound dilution. The polymerase and compound were pre-incubated at 35° C. for 10 minute before the addition of 8 μL of nucleotide substrate mixture (33P-α-labeled competing nucleotide at K$_M$ and 0.5 mM of the remaining three nucleotides). The assay plates were covered and incubated at 35° C. for 90 min. Reactions were then filtered through 96-well DEAE-81 filter plates via vacuum. The filter plates were then washed under vacuum with multiple volumes of 0.125 M NaHPO$_4$, water, and ethanol to remove unincorporated label. Plates were then counted on TopCount to assess the level of product synthesis over background controls. The IC50 value is determined using Prism fitting program.

Preferably, compounds described herein inhibited NS5b polymerase with an IC$_{50}$'s below 1000 μM, more preferably below 100 μM, and most preferably below 10 μM. For example, compound TP-1 has an IC$_{50}$ of 0.15 μM against both wild type HCV polymerase and the S282T mutant enzyme. Table II below shows the activity of TP-1 and TP-2 against both wild type and the S282T mutant enzyme compared to the activities obtained with the triphosphate of 2'-methyl guanidine and the triphosphate of (2R,3R,4R,5R)-2-(4-aminopyrrolo[1,2-f][1,2,4]triazin-7-yl)-3,4-S dihydroxy-5-(hydroxymethyl)-3-methyl-tetrahydrofuran-2-carbonitrile. This demonstrates that replacing the 2' OH of the pyrrolo[1,2-f][1,2,4]triazin-7-yl nucleosides with a 2' F unexpectedly confers activity against resistant S282T HCV mutant strains of virus.

TABLE II

| Triphosphate | WT IC50 (uM) | S282T IC50(uM) | Note |
|---|---|---|---|
| 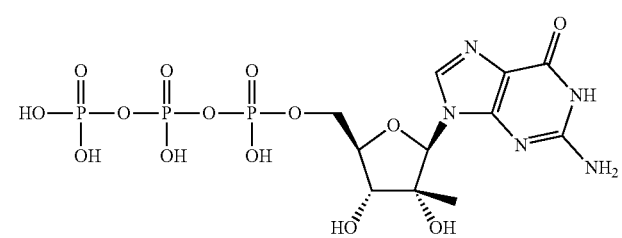<br>2'-C-MeGTP | 0.1 | 20 | from *J. Bio. Chem.*, 2003, 278, 49164 (200 fold shift) |
| 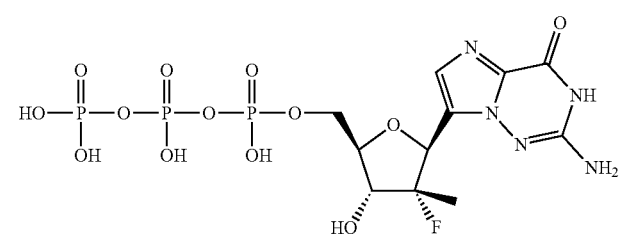<br>TP-1 | 0.15 | 0.15 | (1 fold shift) |

TABLE II-continued

| Triphosphate | WT IC50 (uM) | S282T IC50(uM) | Note |
|---|---|---|---|
| [Structure: triphosphate-ribose(CN, methyl, OH)-pyrrolotriazine-NH2] | 0.525 | 111 | WO/2009/132135 (242 fold shift) |
| [Structure TP-2: triphosphate-ribose(CN, methyl, F)-pyrrolotriazine-NH2] | 0.24 | 1.60 | (7 fold shift) |
| [Structure TP-3: triphosphate-ribose(methyl, F)-pyrrolotriazine-NH2] | 0.034 | | |

HCV EC$_{50}$ Determination

Replicon cells were seeded in 96-well plates at a density of 8×10$^3$ cells per well in 100 of culture medium, excluding Geneticin. Compound was serially diluted in 100% DMSO and then added to the cells at a 1:200 dilution, achieving a final concentration of 0.5% DMSO and a total volume of 200 µL. Plates were incubated at 37° C. for 3 days, after which culture medium was removed and cells were lysed in lysis buffer provided by Promega's luciferase assay system. Following the manufacturer's instruction, 100 µL of luciferase substrate was added to the lysed cells and luciferase activity was measured in a TopCount luminometer. Preferably, compounds described herein have EC50's below 1000 µM, more preferably below 100 ΞM, and most preferably below 10 µM. The activities of representative compounds of Formula I are shown in the Table below.

| Compound No. | EC$_{50}$, µM |
|---|---|
| A-1 | 23 |
| B-1 | 1.4-4.3 |
| B-3 | 16-28 |
| B-4 | 8.4-19 |
| B-5 | 1.93-25.5 |
| B-6 | 13.75-11.1 |
| B-7 | 63-73 |
| B-8 | 35-60 |
| C-1 | 67-70 |
| C-2 | 3.9-12 |
| C-3 | 43-84 |
| C-4 | 9.8-31 |
| C-5 | 24-28 |
| C-6 | 11 |
| 10 | 6.5-8 |
| 22 | 31-45 |
| 23 | 39.4-40.3 |
| 24 | 40.3-70.5 |
| 25 | 9.7-10 |

The cytotoxicity of a compound of the invention can be determined using the following general protocol.

Cytotoxicity Cell Culture Assay (Determination of CC50):

The assay is based on the evaluation of cytotoxic effect of tested compounds using a metabolic substrate.

Assay Protocol for Determination of CC50:
1. Maintain MT-2 cells in RPMI-1640 medium supplemented with 5% fetal bovine serum and antibiotics.
2. Distribute the cells into a 96-well plate (20,000 cell in 100 µl media per well) and add various concentrations of the tested compound in triplicate (100 µl/well). Include untreated control.
3. Incubate the cells for 5 days at 37° C.
4. Prepare XTT solution (6 ml per assay plate) in dark at a concentration of 2 mg/ml in a phosphate-buffered saline pH 7.4. Heat the solution in a water-bath at 55° C. for 5 min. Add 50 µl of N-methylphenazonium methasulfate (5 µg/ml) per 6 ml of XTT solution.

5. Remove 100 μl media from each well on the assay plate and add 100 μl of the XTT substrate solution per well. Incubate at 37° C. for 45 to 60 min in a CO$_2$ incubator.
6. Add 20 μl of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

All publications, patents, and patent documents cited herein above are incorporated by reference herein, as though individually incorporated by reference. The invention has been described with reference to various specific and preferred embodiments and techniques. However, one skilled in the art will understand that many variations and modifications may be made while remaining within the spirit and scope of the invention.

What is claimed is:

1. A compound of Formula I:

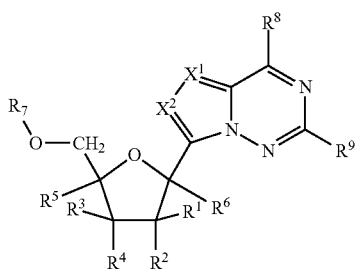

Formula I or a pharmaceutically acceptable salt, thereof;
wherein:
$R^1$ is (C$_1$-C$_8$)alkyl, (C$_4$-C$_8$)carbocyclylalkyl, (C$_1$-C$_8$)substituted alkyl, (C$_2$-C$_8$)alkenyl, (C$_2$-C$_8$)substituted alkenyl, (C$_2$-C$_8$)alkynyl, (C$_2$-C$_8$)substituted alkynyl, or aryl(C$_1$-C$_8$)alkyl;
$R^2$ is halogen;
each $R^3$, $R^4$, or $R^5$ is independently H, OR$^a$, N(R$^a$)$_2$, N$_3$, CN, NO$_2$, S(O)$_n$R$^a$, halogen, (C$_1$-C$_8$)alkyl, (C$_4$-C$_8$)carbocyclylalkyl, (C$_1$-C$_8$)substituted alkyl, (C$_2$-C$_8$)alkenyl, (C$_2$-C$_8$)substituted alkenyl, (C$_2$-C$_8$)alkynyl, (C$_2$-C$_8$)substituted alkynyl, or aryl(C$_1$-C$_8$)alkyl;
or any two of $R^3$, $R^4$ or $R^5$ on adjacent carbon atoms when taken together are —O(CO)O— or when taken together with the ring carbon atoms to which they are attached form a double bond;
$R^6$ is H, OR$^a$, N(R$^a$)$_2$, N$_3$, CN, NO$_2$, S(O)$_n$R$^a$, —C(=O)OR$^{11}$, —C(=O)NR$^{11}$R$^{12}$, —S(O)R$^{11}$, —S(O)$_2$R$^{11}$, —S(O)(OR$^{11}$), —S(O)$_2$(OR$^{11}$), —SO—NR$^{11}$R$^{12}$, halogen, (C$_1$-C$_8$)alkyl, (C$_4$-C$_8$)carbocyclylalkyl, (C$_1$-C$_8$)substituted alkyl, (C$_2$-C$_8$)alkenyl, (C$_2$-C$_8$)substituted alkenyl, (C$_2$-C$_8$)alkynyl, (C$_2$-C$_8$)substituted alkynyl, or aryl(C$_1$-C$_8$)alkyl;
each n is independently 0, 1, or 2;
each R$^a$ is independently H, (C$_1$-C$_8$)alkyl, (C$_2$-C$_8$)alkenyl, (C$_2$-C$_8$)alkynyl, aryl(C$_1$-C$_8$)alkyl, (C$_4$-C$_8$)carbocyclylalkyl, —C(=O)R$^{11}$, —C(=O)OR$^{11}$, —C(=O)NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), or —SO$_2$NR$^{11}$R$^{12}$;

$R^7$ is H, —C(=O)R$^{11}$, —C(=O)OR$^{11}$, —C(=O)NR$^{11}$R$^{12}$, —C(=O)SR$^{11}$, —S(O)R$^{11}$, —S(O)$_2$R$^{11}$, —S(O)(OR$^{11}$), —S(O)$_2$(OR$^{11}$), —SO$_2$NR$^{11}$R$^{12}$, or

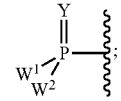

each Y or Y$^1$ is, independently, O, S, NR, $^+$N(O)(R), N(OR), $^+$N(O)(OR), or N—NR$_2$;
W$^1$ and W$^2$, when taken together, are —Y$^3$(C(R$^y$)$_2$)$_3$Y$^3$—; or one of W$^1$ or W$^2$ together with either R$^3$ or R$^4$ is —Y$^3$— and the other of W$^1$ or W$^2$ is Formula Ia; or W$^1$ and W$^2$ are each, independently, a group of the Formula Ia:

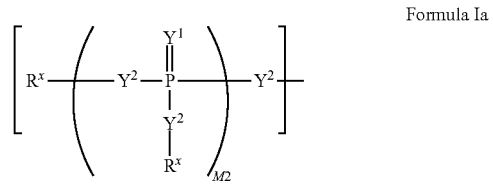

Formula Ia wherein:
each Y$^2$ is independently a bond, O, CR$_2$, NR, $^+$N(O)(R), N(OR), $^+$N(O)(OR), N—NR$_2$, S, S—S, S(O), or S(O)$_2$;
each Y$^3$ is independently O, S, or NR;
M2 is 0, 1 or 2;
each R$^x$ is independently R$^y$ or the formula:

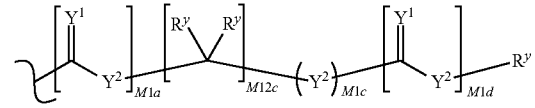

wherein:
each M1a, M1c, and M1d is independently 0 or 1;
M12c is 0, 1, 2, 3, 4, 5, 6, 7, 8, 9, 10, 11 or 12;
each R$^y$ is independently H, F, Cl, Br, I, OH, R, —C(=Y$^1$)R, —C(=Y$^1$)OR, —C(=Y$^1$)N(R)$_2$, —N(R)$_2$, $^+$N(R)$_3$, —SR, —S(O)R, —S(O)$_2$R, —S(O)(OR), —S(O)$_2$(OR), —OC(=Y$^1$)R, —OC(=Y$^1$)OR, —OC(=Y$^1$)(N(R)$_2$), —SC(=Y$^1$)R, —SC(=Y$^1$)OR, —SC(=Y$^1$)(N(R)$_2$), —N(R)C(=Y$^1$)R, —N(R)C(=Y$^1$)OR, —N(R)C(=Y$^1$)N(R)$_2$, —SO$_2$NR$_2$, —CN, —N$_3$, —NO$_2$, —OR, or W$^3$; or when taken together, two R$^y$ on the same carbon atom form a carbocyclic ring of 3 to 7 carbon atoms;
each R is independently H, (C$_1$-C$_8$) alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, C$_2$-C$_{20}$ heterocyclyl, C$_2$-C$_{20}$ substituted heterocyclyl, arylalkyl or substituted arylalkyl;

W³ is W⁴ or W⁵; W⁴ is R, —C(Y¹)R^y, —C(Y¹)W⁵, —SO₂R^y, or —SO₂W⁵; and W⁵ is a carbocycle or a heterocycle wherein W⁵ is independently substituted with 0 to 3 R^y groups;

each X¹ or X² is independently C—R¹⁰ or N;

each R⁸ is halogen, NR¹¹R¹², N(R¹¹)OR¹¹, NR¹¹NR¹¹R¹², N₃, NO, NO₂, CHO, CN, —CH(=NR¹¹), —CH=NNHR¹¹, —CH=N(OR¹¹), —CH(OR¹¹)₂, —C(=O)NR¹¹R¹², —C(=S)NR¹¹R¹², —C(=O)OR¹¹, (C₁-C₈)alkyl, (C₂-C₈)alkenyl, (C₂-C₈)alkynyl, (C₄-C₈)carbocyclylalkyl, optionally substituted aryl, optionally substituted heteroaryl, —C(=O)(C₁-C₈)alkyl, —S(O)ₙ(C₁-C₈)alkyl, aryl(C₁-C₈)alkyl, OR¹¹ or SR¹¹;

each R⁹ or R¹⁰ is independently H, halogen, NR¹¹R¹², N(R¹¹)OR¹¹, NR¹¹NR¹¹R¹², N₃, NO, NO₂, CHO, CN, —CH(=NR¹¹), —CH=NNHR¹¹, —CH=N(OR¹¹), —CH(OR¹¹)₂, —C(=O)NR¹¹R¹², —C(=S)NR¹¹R¹², —C(=O)OR¹¹, R¹¹, OR¹¹ or SR¹¹;

each R¹¹ or R¹² is independently H, (C₁-C₈)alkyl, (C₂-C₈)alkenyl, (C₂-C₈)alkynyl, (C₄-C₈)carbocyclylalkyl, optionally substituted aryl, optionally substituted heteroaryl, —C(=O)(C₁-C₈)alkyl, —S(O)ₙ(C₁-C₈)alkyl or aryl(C₁-C₈)alkyl; or R¹¹ and R¹² taken together with a nitrogen to which they are both attached form a 3 to 7 membered heterocyclic ring wherein any one carbon atom of said heterocyclic ring can optionally be replaced with —O—, —S— or —NR^a—;

wherein each (C₁-C₈)alkyl, (C₂-C₈)alkenyl, (C₂-C₈)alkynyl or aryl(C₁-C₈)alkyl of each R¹, R³, R⁴, R⁵, R⁶, R¹¹ or R¹² is, independently, optionally substituted with one or more halo, hydroxy, CN, N₃, N(R^a)₂ or OR^a; and wherein one or more of the non-terminal carbon atoms of each said (C₁-C₈)alkyl may be optionally replaced with —O—, —S— or —NR^a.

2. A compound according to claim 1 represented by Formula II

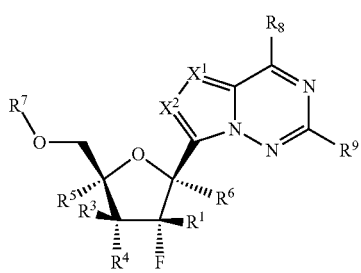

Formula II wherein each Y and Y¹ is O; X¹ is CR¹⁰ or N and X² is CH; or a pharmaceutically acceptable salt or ester thereof.

3. A compound according to claim 2 wherein R⁸ is halogen, NR¹¹R¹², N(R¹¹)OR¹¹, NR¹¹NR¹¹R¹², OR¹¹ or SR¹¹.

4. A compound according to claim 3 wherein R⁹ is H, halogen, SR¹¹ or NR¹¹R¹².

5. A compound according to claim 4 wherein R⁶ is H, OR^a, CN, methyl, ethenyl, or ethynyl.

6. A compound according to claim 5 wherein R⁶ is H.

7. A compound according to claim 5 wherein R⁶ is CN.

8. A compound according to claim 5 wherein R⁴ is OR^a.

9. A compound according to claim 8 represented by Formula III

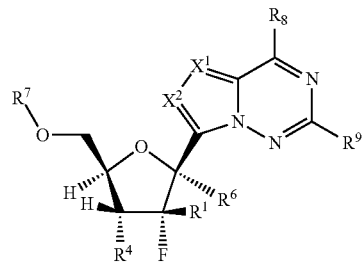

Formula III wherein R¹ is methyl or ethynyl; or a pharmaceutically acceptable salt or ester thereof.

10. A compound according to claim 8 wherein R⁷ is H or

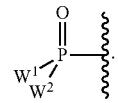

11. A compound according to claim 10 wherein R⁷ is

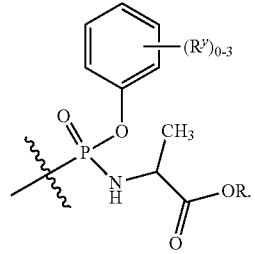

12. A compound according to claim 8 wherein R¹ is CH₃.

13. A compound that is

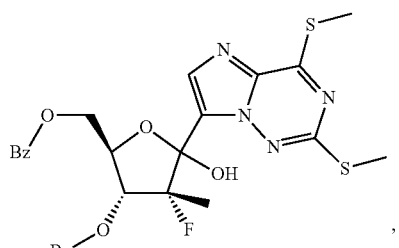

,

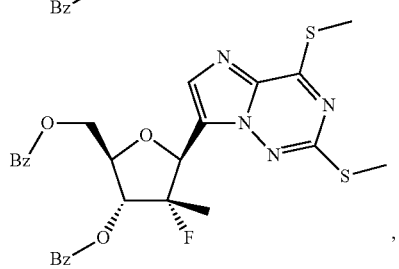

,

137
-continued
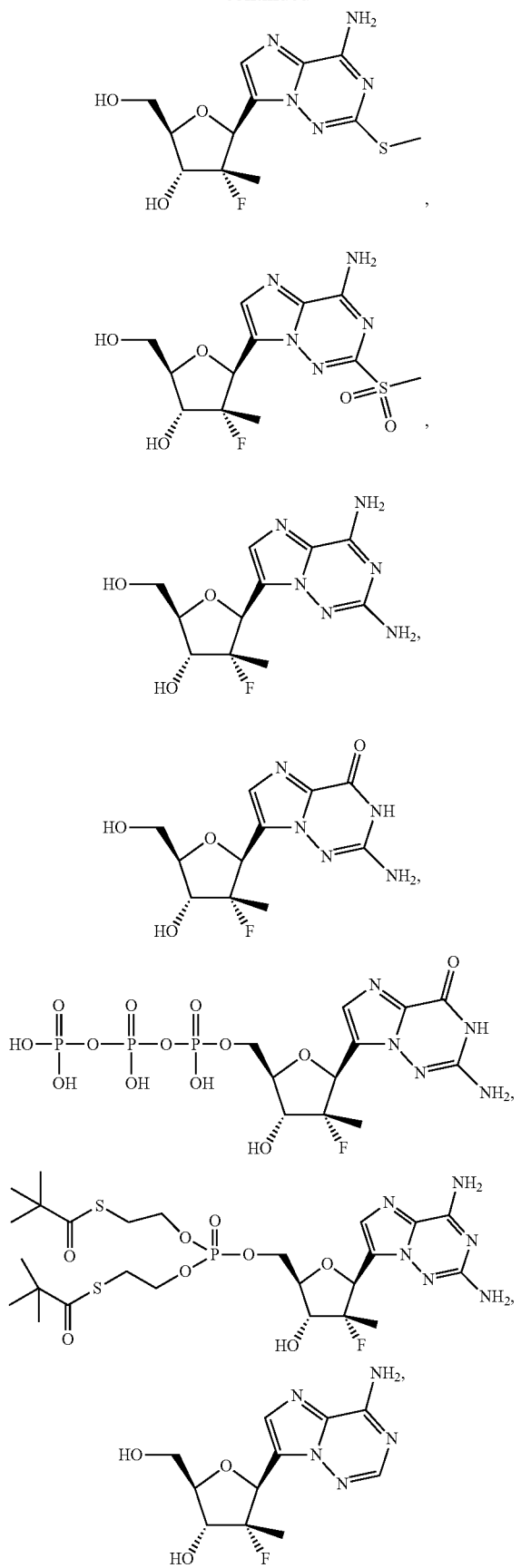
138
-continued
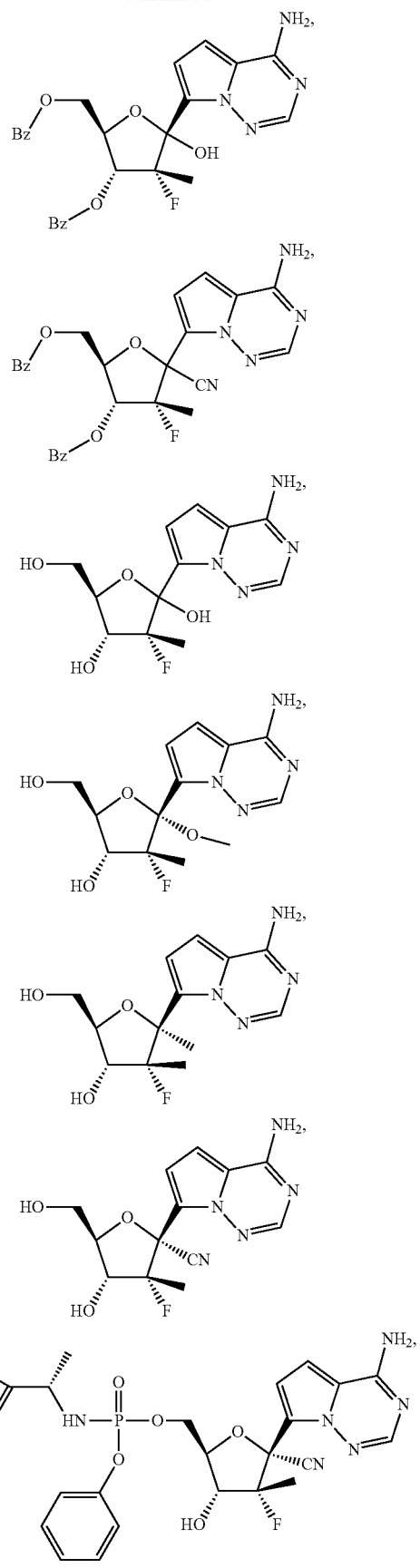

139
-continued
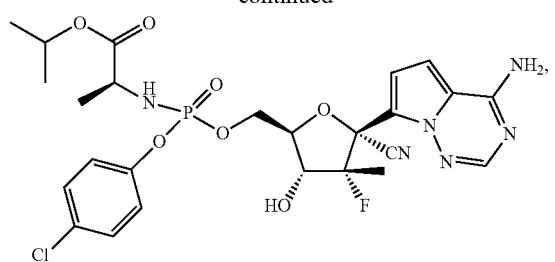
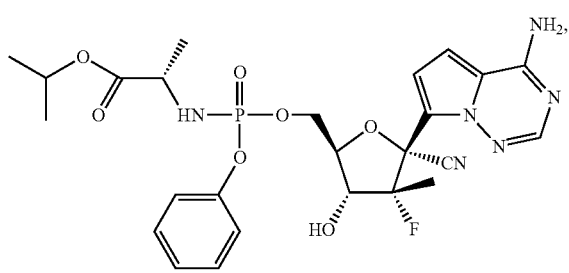
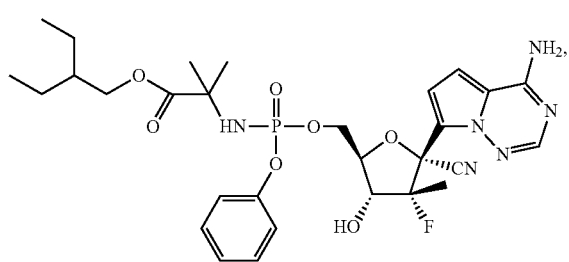
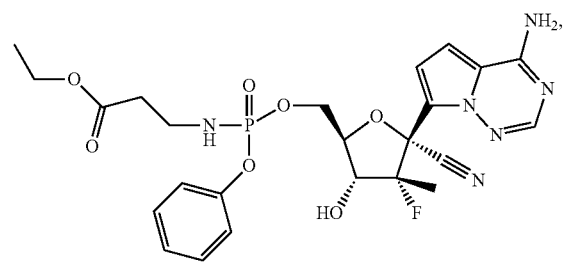
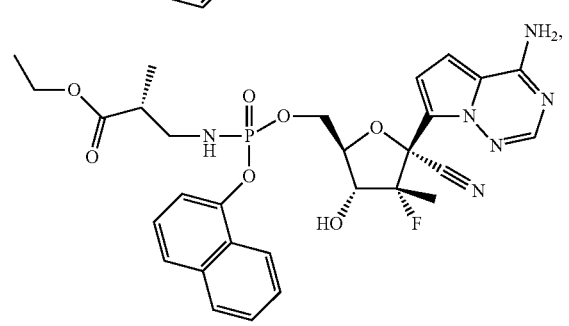
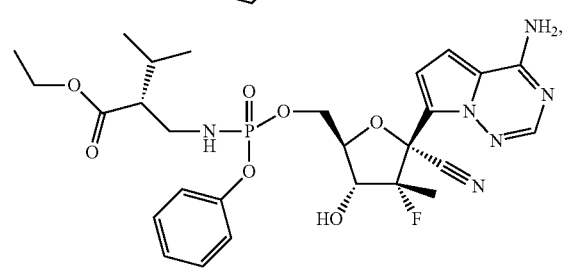
140
-continued
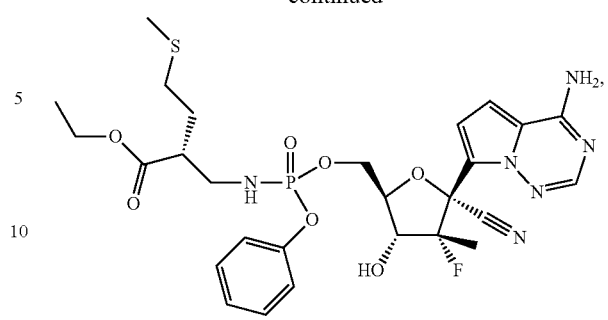
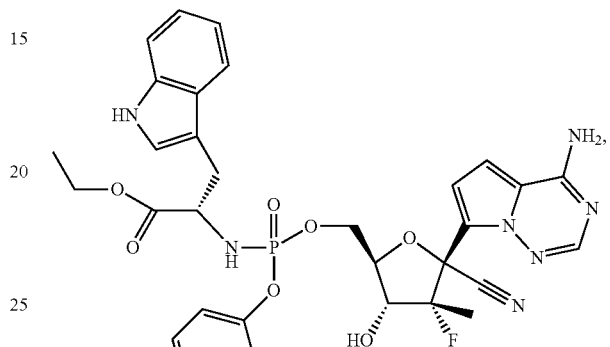
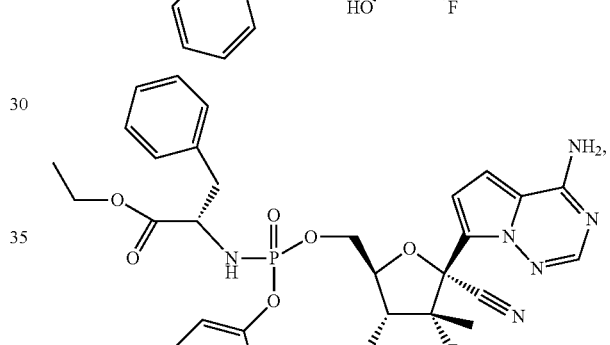
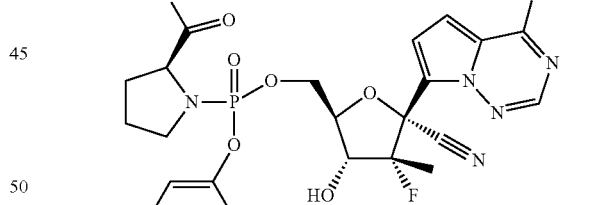
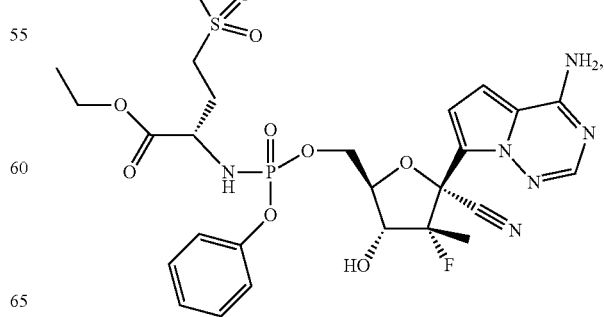

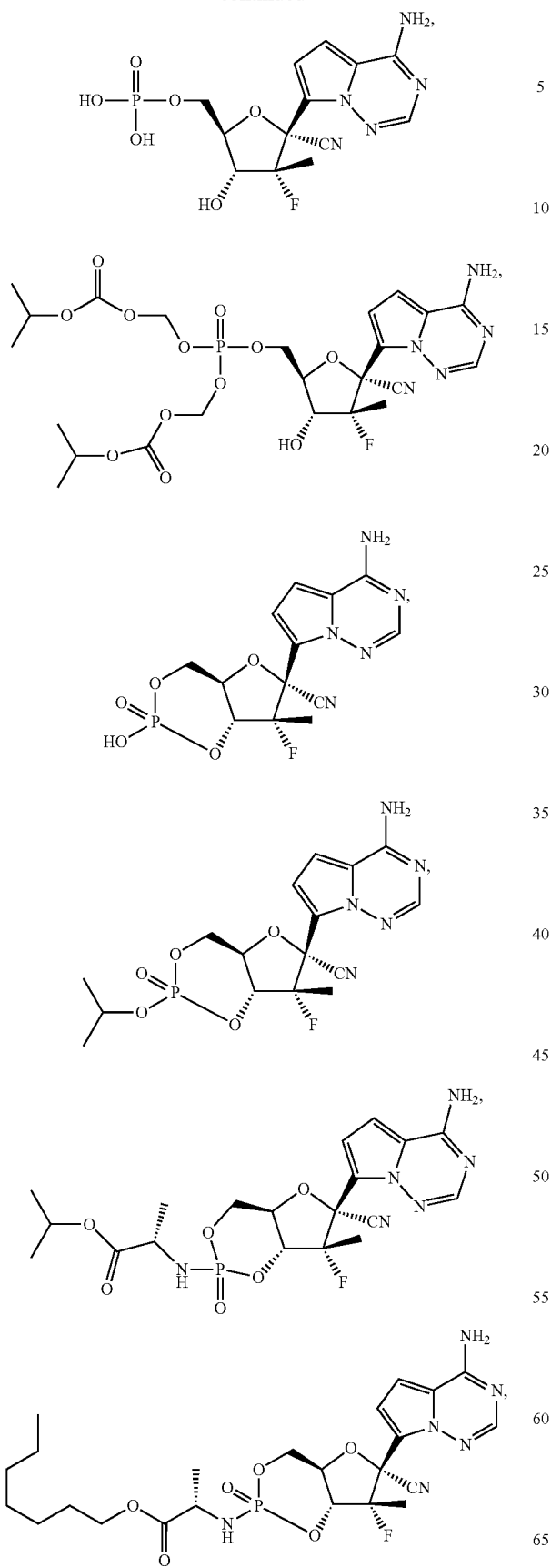
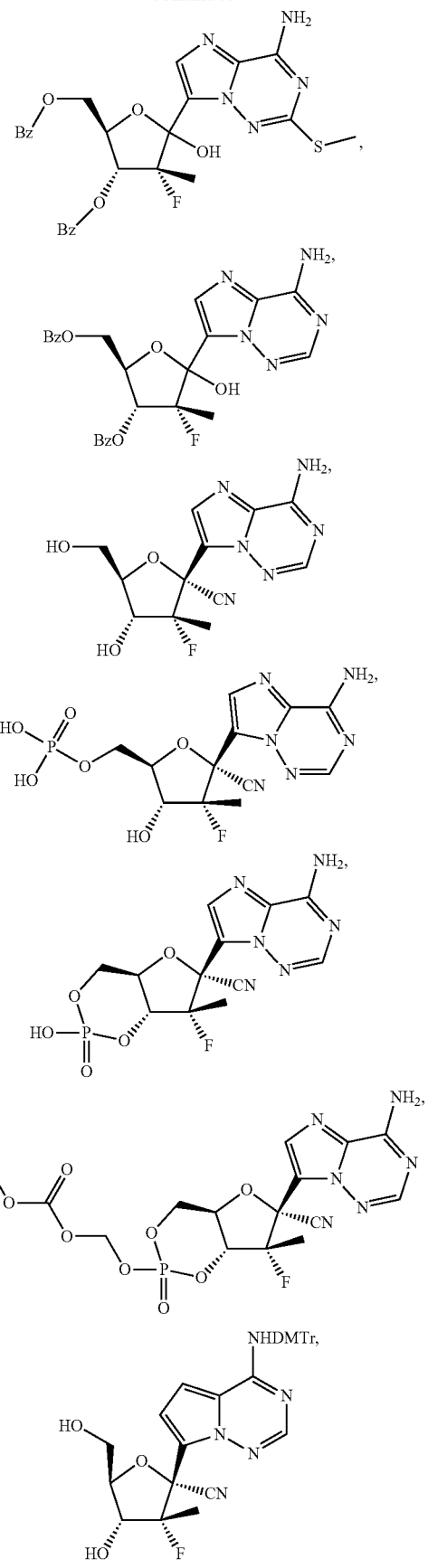

143
-continued
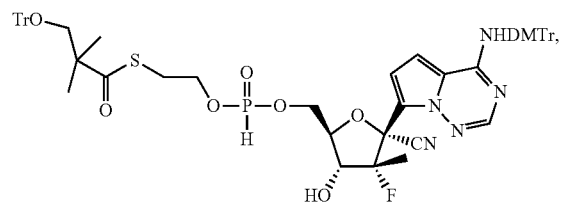
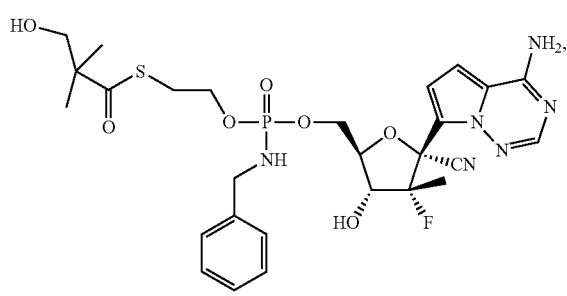
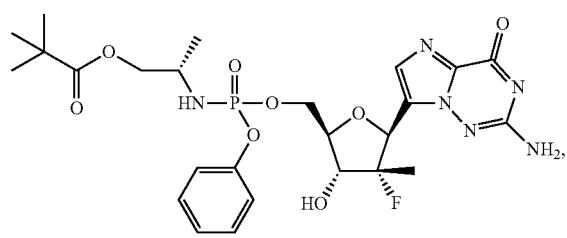
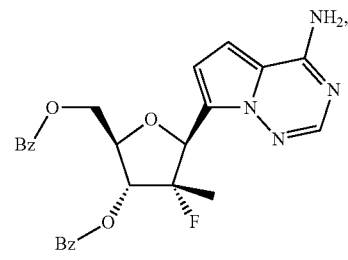
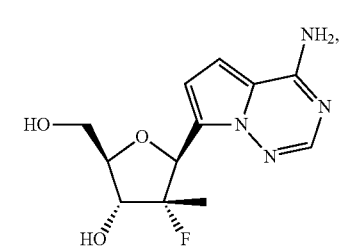
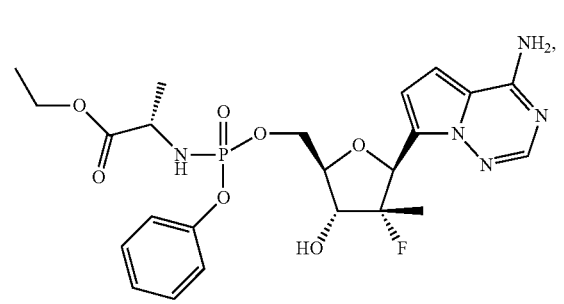
144
-continued
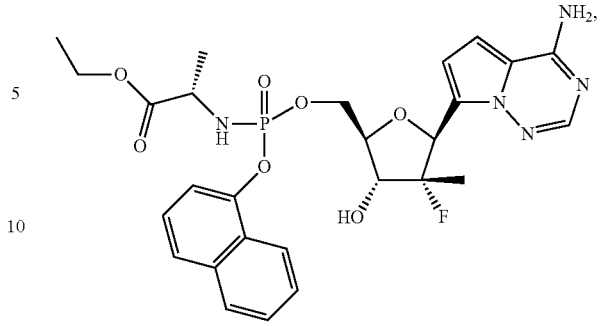
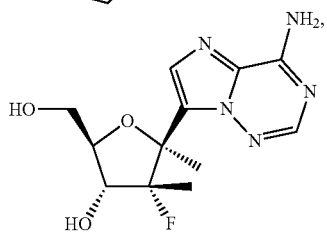
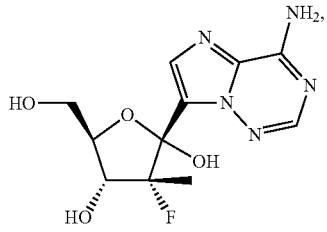
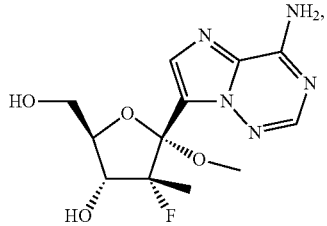
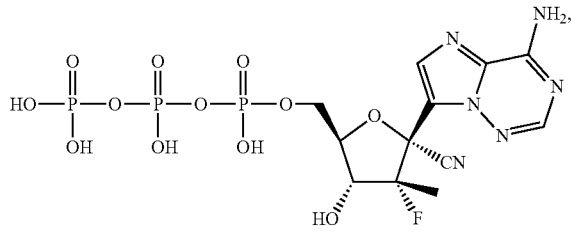
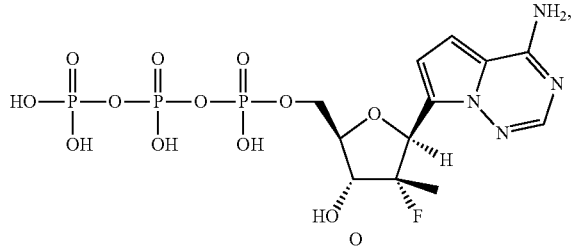
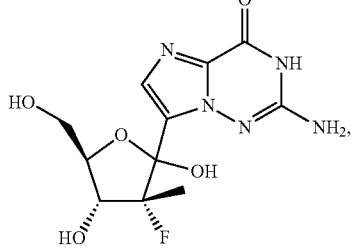

145
-continued
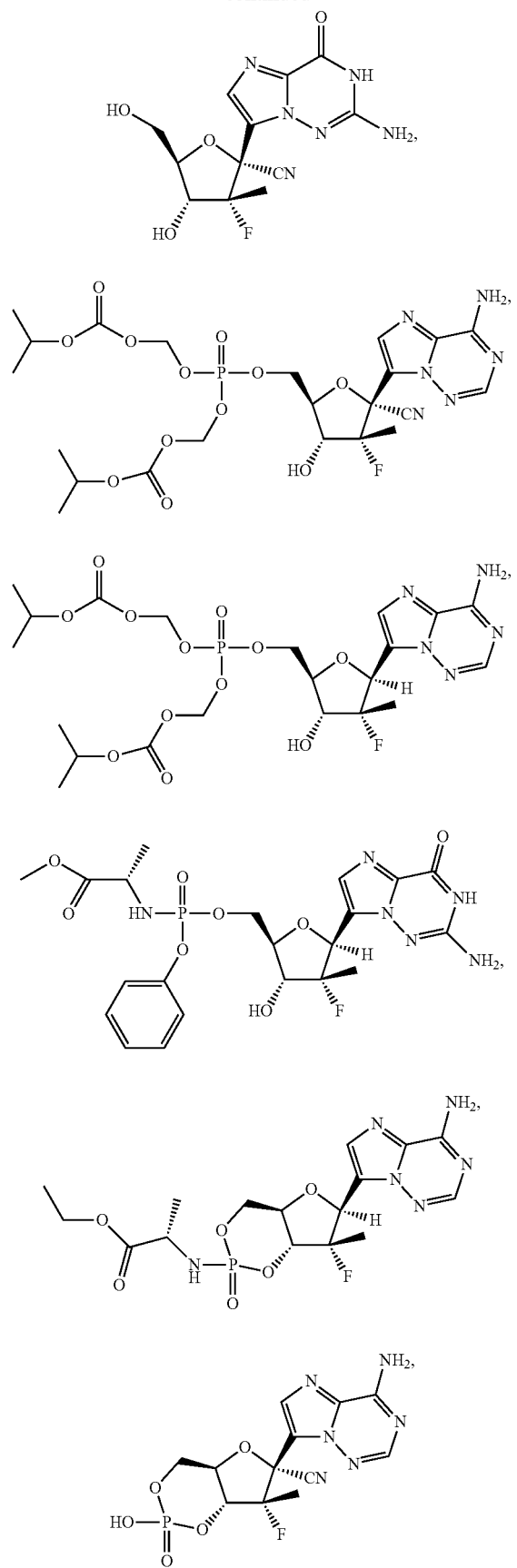
146
-continued
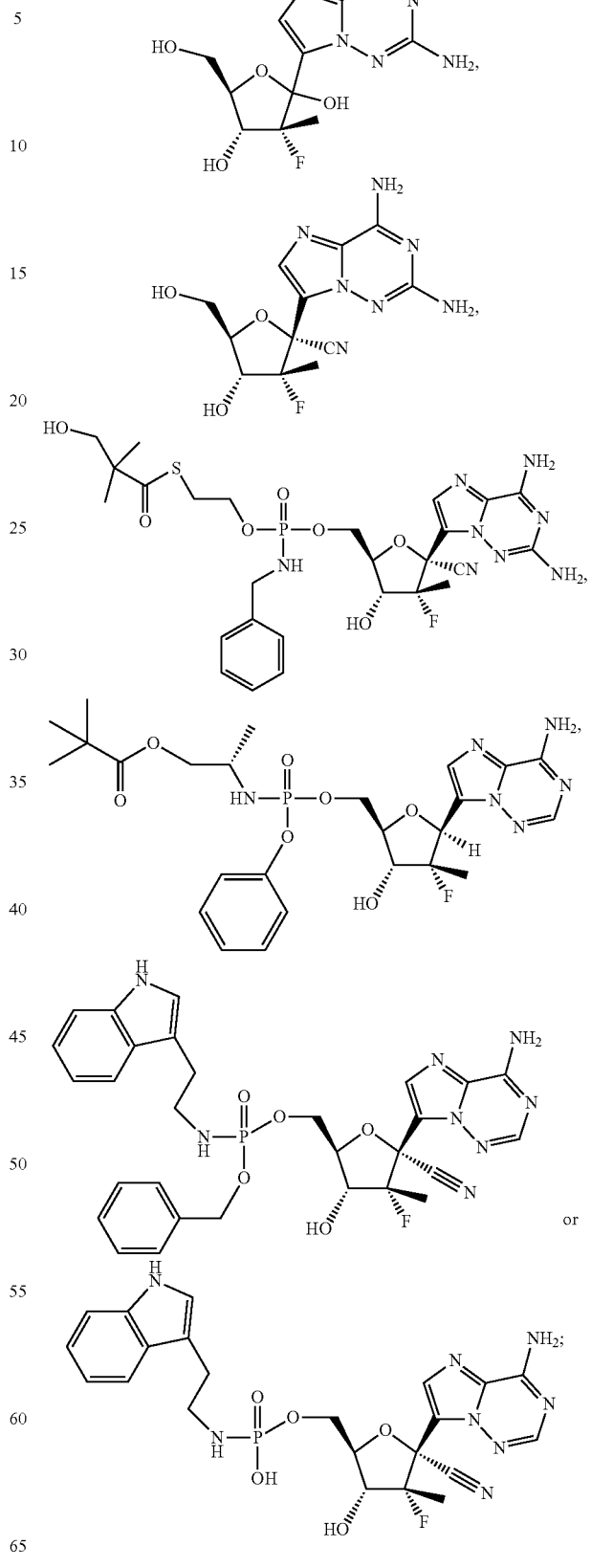
or a pharmaceutically acceptable salt or ester thereof.

14. A compound useful for the preparation of a compound of Formula I selected from the group consisting of

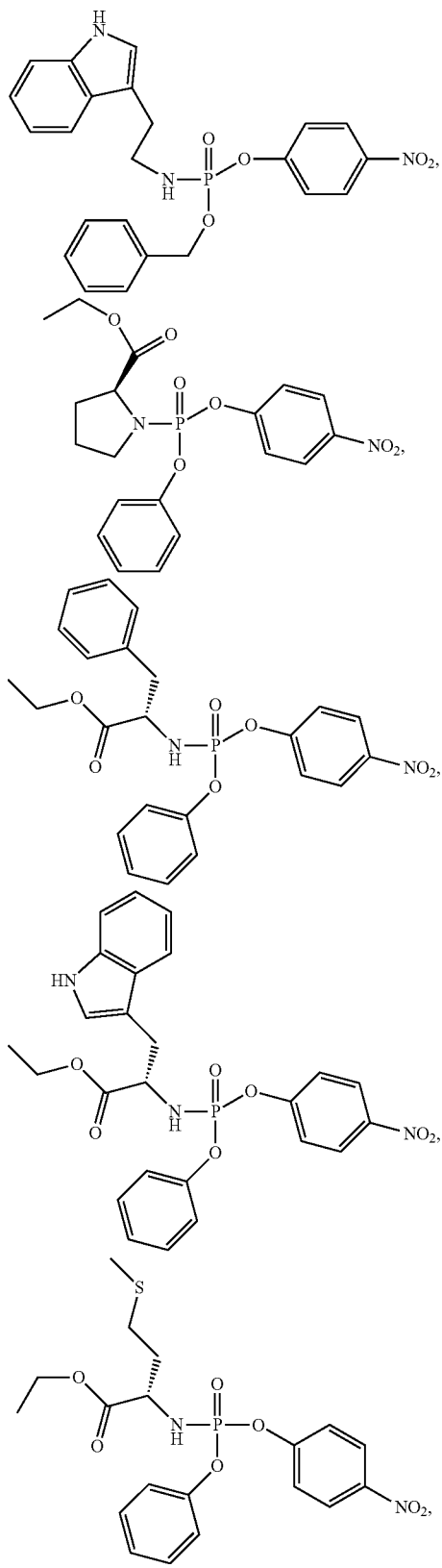

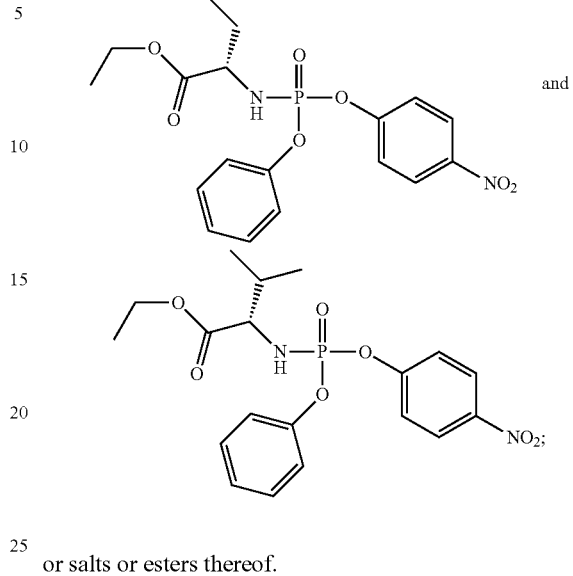

or salts or esters thereof.

15. A pharmaceutical composition comprising a therapeutically effective amount of a compound of claim 1 and a pharmaceutically acceptable carrier.

16. The pharmaceutical composition of claim 15 further comprising at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, endothelin antagonists, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

17. A method of treating a Flaviviridae virus infection comprising administering to a mammal in need thereof a therapeutically effective amount of a compound or pharmaceutical composition of claim 1.

18. The method of claim 17 wherein the viral infection is a Hepatitis C virus infection.

19. The method of claim 18 wherein the viral infection is caused by a S282T mutant of Hepatitis C virus.

20. The method of claim 17 further comprising administering at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, endothelin antagonists, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers and other drugs for treating HCV; or mixtures thereof.

* * * * *